(12) United States Patent
Pero et al.

(10) Patent No.: US 7,229,960 B2
(45) Date of Patent: Jun. 12, 2007

(54) METHODS AND COMPOSITIONS FOR INHIBITING GRB7

(75) Inventors: Stephanie C. Pero, Essex Junction, VT (US); David N. Krag, Shelburne, VT (US); Lyn Oligino, South Burlington, VT (US)

(73) Assignee: University of Vermont and State Agricultural College, Burlington, VT (US)

( * ) Notice: Subject to any disclaimer, the term of this patent is extended or adjusted under 35 U.S.C. 154(b) by 0 days.

(21) Appl. No.: 10/013,815

(22) Filed: Nov. 5, 2001
(Under 37 CFR 1.47)

(65) Prior Publication Data
US 2003/0105000 A1   Jun. 5, 2003

Related U.S. Application Data

(60) Provisional application No. 60/245,755, filed on Nov. 3, 2000.

(51) Int. Cl.
*A01N 37/18* (2006.01)
*A61K 38/00* (2006.01)
*C07K 5/00* (2006.01)
*C07K 7/00* (2006.01)

(52) U.S. Cl. .............. 514/2; 514/11; 514/13; 514/14; 514/15

(58) Field of Classification Search .............. 514/2
See application file for complete search history.

(56) References Cited

U.S. PATENT DOCUMENTS 5,710,129 A   1/1998   Lynch et al.
6,001,583 A   12/1999  Margolis

FOREIGN PATENT DOCUMENTS

WO   WO 97/08193   *   3/1997

OTHER PUBLICATIONS

Gura (Science, 1997, 278:1041-1042).*
Jain (Sci. Am., 1994, 271:58-65).*
Curti (Crit. Rev. in Oncology/Hematology, 1993, 14:29-39).*
Bowie et al (Science, 1990, 257:1306-1310).*
Burgess et al ( J of Cell Bio. 111:2129-2138, 1990).*
, Bork (Genome Research, 2000, 10:398-400).*
Gram, et al., "Identification of phosphopeptide ligands for the Src-homology 2 (SH2) domain of Grb2 by phage display," 1997, Eur. J. Biochem., vol. 246, pp. 633-637.
Müller, et al., "Rapid Identification of Phosphopeptide Ligands for SH2 Domains," 1996, The Journal of Biological Chemistry, vol. 271, No. 28, pp. 16500-16505.
Schoepfer, et al., Highly Potent Inhibitors of the Grb2-SH2 Domain, 1999, Bioorganic & Medicinal Chemistry Letters 9, pp. 221-226.

Ettmayer, et al., "Structural and Conformational Requirements for High-Affinity Binding to the SH2 Domain of Grb2," 1999, J. Med. Chem., vol. 42, pp. 971-980.
Furet, et al., "Structure-Based Design and Synthesis of High Affinity Tripeptide Ligands of the Grb2-SH2 Domain," 1998, J. Med. Chem., vol. 41, pp. 3442-3449.
Gay, et al., "Selective Grb2 SH2 Inhibitors as Anti-Ras Therapy," 1999, Int. J. Cancer, vol. 83, pp. 235-241.
Gay, et al., "Effect of Potent and Selective Inhibitors of the Grb2 SH2 Domain on Cell Motility," 1999, The Journal of Biological Chemistry, vol. 274, No. 33, pp. 23311-23315.
Raheul, et al., "Structural Basis for the High Affinity of Amino-Aromatic SH2 Phosphopeptide Ligands," 1998, J. Mol. Biol., vol. 279, pp. 1013-1022.
Schoepfer, et al., "Structure-Based Design of Peptidomimetic Ligands of the Grb2-SH2 Domain," 1998, Bioorganic & Medicinal Chemistry Letters 8, pp. 2865-2870.
Oligino, et al., "Nonphosphorylated Peptide Ligands for the Grb2 Src Homology 2 Domain," 1997, The Journal of Biological Chemistry, vol. 272, No. 46, pp. 29046-29052.
Burgess, et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," 1990, The Journal of Cell Biology, vol. 111, pp. 2129-2138.
Lazar, et al., "Transforming Growth Factor α: Mutation of Aspartic Acid 47 and Leucine 48 Results in Different Biological Activities," 1988, Molecular and Cellular Biology, pp. 1247-1252.
Tao, et al., "Studies of Aglycosylated Chimeric Mouse-Human IgG," 1989, The Journal of Immunology, vol. 143, No. 8, pp. 2595-2601.
Gillies, et al., "Antigen binding and biological activities of engineered mutant chimeric antibodies with human tumor specificities", 1990, Hum. Antibod. Hybridomas, vol. 1, No. 1, pp.47-54.
Lou, et al., "Solution Structure and Dynmaics of G1TE, a Nonphosphorylated Cyclic Peptide Inhibitor for the Grb2 SH2 Domain," 1999, Archives of Biochemistry and Biophysics, vol. 372, No. 2, pp. 309-314.
Burke, Jr., et al., "Monocarboxylic-Based Phosphotyrosyl Mimetics in the Design of GRB2 SH2 Domain Inhibitors," 1999, Bioorganic & Medicinal Chemistry Letters 9, pp. 347-352.
Long, et al., "Structural Requirements for Tyr in the Consensus Sequence Y-E-N of a Novel Nonphosphorylated Inhibitor to the Grb2-SH2 Domain," 1999, Biochemical and Biophysical Research Communications, vol. 264, pp. 902-908.
Yao, et al., "Potent Inhibition of Grb2 SH2 Domain Binding by Non-Phophate-Containing Ligands," 1999, J. Med. Chem., vol. 42, pp. 25-35.

(Continued)

*Primary Examiner*—Susan Ungar
(74) *Attorney, Agent, or Firm*—Wolf Greenfield & Sacks, PC

(57) ABSTRACT

The invention provides methods and compositions for treating subjects using Grb7 antagonists. Specifically disclosed are Grb7 antagonists that bind selectively to Grb7 and interfere with the ability of Grb7 to bind to its native ligands. These compositions are useful in the prevention and treatment of disorders characterized by abnormal interaction of Grb7 with its native ligands (e.g., ErbB2).

5 Claims, 8 Drawing Sheets

OTHER PUBLICATIONS

Ye, et al., "L-O-(2-Malonyl)tyrosine: A New Phosphotyrosyl Mimetic for the Preparation of Src Homology 2 Domain Inhibitory Peptides," 1995, J. Med. Chem., vol. 38, pp. 4270-4275.

Hart, et al., "Potent Inhibitory Ligands of the GRB2 SH2 Domain from Recombinant Peptide Libraries," 1999, Cell. Signal., vol. 11, No. 6, pp. 453-464.

Long, et al., "Significant Compensatory Role of Position Y-2 Conferring High Affinity to Non-Phosphorylated Inhibitors of GRB2 SH2 Domain," 1999, Bioorganic & Medicinal Chemistry Letters 9, pp. 2267-2272.

Long, et al., "High affinity nonphosphorylated cyclic peptide inhibitors of Grb2-SH2/growth factor receptor interactions," Book Title: "Peptides for the New Millennium," Book Author/Editor: Greg B. Field; James B. Tam and George Barany; Book Publisher: Kulwer Academic Publishers, Netherlands, pp. 567-570, 2000.

Garcia-Echeverria, et al., Mapping the X(+1) binding site of the Grb2-SH2 domain with alpha, alpha-distributed cyclic alpha-amino acids, 1999, Bioorg. Med. Chem. Lett., vol. 9, No. 20, pp. 2915-2920 Abstract.

Caravatti, et al., "Structure-based design of a non-peptide antagonist of the SH2 domain of GRB2," Bioorg. Med. Chem. Lett., vol. 9, No. 14, pp. 1973-1978 Abstract.

Furet, et al., "Discovery of 3-aminobenzyloxcarbonyl as an N-terminal group conferring high affinity to the minimal phosphopeptide sequence recognized by the Grb2-SH2 domain," 1997, J. Med. Chem., vol. 40, No. 22, pp. 3551-3556 Abstract.

Garcia-Echeverria, et al., Potent antagonists of the SH2 domain of Grb2: optimization of the X+1 position of 3-amino-Z-Tyr(PO3H2)-X+1-Asn-NH2., 1998, J. Med. Chem., vol. 41, No. 11, pp. 1741-1744 Abstract.

Pero, et al., "Identification of Novel Non-phosphorylated Ligands, Which Bind Selectively to the SH2 Domain of Grb7," The Journal of Biological Chemistry, Apr. 5, 2002, vol. 277, No. 14, pp. 11918-11926.

Janes et al., Structural determinants of the interaction between the erbB2 receptor and the Src homology 2 domain of Grb7. J Biol Chem. Mar. 28, 1997;272(13):8490-7.

Oligino et al., Nonphosphorylated peptide ligands for the Grb2 Src homology 2 domain. J Biol Chem. Nov. 14, 1997;272(46):29046-52.

Keegan et al., Use of the two hybrid system to detect the association of the protein-tyrosine-phosphatase, SHPTP2, with another SH2-containing protein, Grb7. Oncogene. Apr. 4, 1996;12(7):1537-44.

PCT/US01/47400 International Search Report; Mailing Date—Nov. 29, 2002.

PCT/US01/47400 Written Opinion; Mailing Date—Aug. 11, 2003.

PCT/US01/47400 International Preliminary Exmination Report; Mailing Date—Apr. 15, 2004.

* cited by examiner

METHODS AND COMPOSITIONS FOR INHIBITING GRB7

RELATED APPLICATIONS

This application claims benefit to U.S. Provisional Patent Application No. 60/245,755, filed Nov. 3, 2000, now abandoned. The contents of application No. 60/245,755 are incorporated by reference herein in their entirety.

FIELD OF THE INVENTION

The invention relates to specific Grb7 antagonists and their use in the prevention and treatment of disorders associated with adverse or abnormal interaction of Grb7 with its endogenous ligands.

BACKGROUND OF THE INVENTION

Signal transduction is the process by which extracellular signals are transduced into a cell, and thereby impact upon process such as cell proliferation and differentiation. Tyrosine phosphorylation is a common mechanism for transducing a signal between signaling factors. Tyrosine kinases are enzymes which are capable of phosphorylating peptides and polypeptides at tyrosine residues. A subset of tyrosine kinases is also capable of dimerizing and thereby phosphorylating itself. Phosphatases are enzymes, which can optionally be receptors as well, capable of dephosphorylating a molecule such as a signaling factor. Uncontrolled tyrosine kinase activation has been implicated in the increased proliferation of cancerous cells.

In addition to tyrosine kinases and phosphatases, signal transduction pathways also use adaptor proteins. Adaptor proteins are intracellular proteins that act as intermediary proteins. These proteins allow for the association of other, usually signaling, proteins which would not otherwise be capable of interacting with each other. Adaptor proteins commonly do not have an activity other than their "adaptor" function, although they may act as substrates for other proteins such as, for example, kinases. Many adaptor proteins share conserved protein interaction domains such as, for example, Src homology (SH) domains. SH2 domains recognize and bind to phosphorylated tyrosine residues.

Abnormal signal transduction has been associated with a variety of disorders. A number of oncogenes are mutant variants of normally occurring signaling factors, including tyrosine kinases. One strategy for preventing or treating such disorders is to interfere with the unregulated or increased signal transduction which is thought to occur in these disorders.

SUMMARY OF THE INVENTION

The invention relates to the identification and inhibition of abnormal signal transduction pathways involving Growth Factor Receptor-Bound Protein (Grb) 7. In one specific aspect, the invention relates, in part, to the identification of Grb7 antagonists. As used herein, Grb7 antagonists are compounds which bind to Grb7, preferably at the SH2 domain of Grb7, and thereby preclude or diminish binding of Grb7 to its endogenous ligands. The terms "Grb7 antagonist" and "Grb7 inhibitor" are used interchangeably herein. By inhibiting the interaction of Grb7 with its ligands, these antagonists are able to modulate signal transduction pathways involving Grb7.

The invention is based, in part, on the discovery that non-phosphorylated peptides having a conserved amino acid domain of YAN, YEN or YDN are capable of binding to Grb7 specifically. Prior to the invention, the ability of peptides with these characteristics to bind to and inhibit Grb7 had not been recognized. A non-phosphorylated peptide having a YEN motif (nested in a CELYENVGMYC (SEQ ID NO:32) sequence) had been previously reported to bind to Grb2, another SH2 domain containing protein that binds to some of the same endogenous phosphotyrosine sites as the Grb7 SH2 domain.

Thus, in one aspect, the invention provides a method for treating a subject having a disorder characterized by abnormal interaction of Grb7 and a Grb7 ligand. Preferably, the Grb7 ligand is a native ligand or is naturally endogenous to a cell type being treated. The Grb7 ligand may be selected from the group consisting of a tyrosine kinase, a phosphatase, and an adaptor protein, but is not so limited. The invention further provides a method for prophylactically treating a subject at risk of developing a disorder characterized by abnormal interaction of Grb7 with a Grb7 ligand. In embodiments of either method, the methods further comprise first selecting a subject to be treated (e.g., a subject having the disorder or a subject at risk of developing the disorder). The method comprises administering to a subject in need of such treatment a peptide comprising an YXN amino acid sequence. In important embodiments, the sequence is selected from the group consisting of SEQ ID NO:8 (YAN), SEQ ID NO:9 (YEN), and SEQ ID NO:10 (YDN), or a functional equivalent thereof. The peptide is administered in an amount effective to either prevent or inhibit the disorder, depending upon whether the method is intended for prophylactic or therapeutic use. In related aspects, the foregoing methods can also be performed by administering to the subject non-peptide small molecules that mimic the peptides of the invention.

In another aspect, the invention provides a method for inhibiting an interaction between Grb7 with a Grb7 ligand in a cell expressing Grb7 and the Grb7 ligand. The method involves contacting a cell expressing Grb7 and the Grb7 ligand with a peptide having a YXN amino acid sequence preferably selected from the group consisting of SEQ ID NO:8, SEQ ID NO:9, SEQ ID NO: 10, and functional equivalents thereof in an amount effective for inhibiting the interaction between Grb7 and the Grb7 ligand in a cell expressing Grb7 and the Grb7 ligand. The method may be performed in vivo or in vitro.

The invention further provides a method for inhibiting a metastasis (e.g., preventing tumor cell metastasis) by administering to a subject in need of such treatment one or a combination of any of the above-identified peptides in an amount effective to prevent the formation or development of a metastasis.

In preferred embodiments, the peptide is non-phosphorylated. In even more preferred embodiments, the peptides are cyclized or are capable of being cyclized. The cyclic peptide may be so formed using, for example, thio-ether linkages, peptide bonds or disulfide linkages. In a further embodiment, the functional equivalent of the peptide is a fluoride derivative. In some embodiments, the functional equivalents do not comprise a YVN motif and, in still others, they do not comprise a YIN motif.

In an important embodiment, the peptide comprises an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:34; SEQ ID NO: 60 through to SEQ ID NO: 194, inclusive, SEQ ID NO:35, SEQ ID NO:39, SEQ ID NO:40, SEQ ID NO:41, SEQ ID NO:42, SEQ ID NO:43, SEQ ID NO:44, SEQ ID NO:47, SEQ ID NO:48, SEQ ID NO:49, SEQ ID NO:50, SEQ ID NO:51, SEQ ID NO:52, and SEQ ID NO:53, or is a functionally equivalent thereof. Functional equivalents include functionally equivalent fragments of the foregoing amino acid sequences. In a related embodiment, the peptide consists of an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:34; SEQ ID NO: 60 through to SEQ ID NO: 194, inclusive, SEQ ID NO:35, SEQ ID NO:39, SEQ ID NO:40, SEQ ID NO:41, SEQ ID NO:42, SEQ ID NO:43, SEQ ID NO:44, SEQ ID NO:47, SEQ ID NO:48, SEQ ID NO:49, SEQ ID NO:50, SEQ ID NO:51, SEQ ID NO:52, and SEQ ID NO:53.

The invention also provides compositions of, and methods of use for, peptides that differ from the peptides of SEQ ID NO:1 through to SEQ ID NO:7 in the flanking amino acid regions including the amino acids between the start of the peptide and the first cysteine residue and/or the amino acids between the last cysteine residue and the end of the peptide. These peptides may include deletion of 1, 2, 3 or 4 of these flanking amino acids or substitutions of each and/or every of the amino acids or additions of additional amino acids or other group.

In one embodiment, the disorder is in a tissue selected from the group consisting of the breast, esophagus, prostate, kidney, liver, gonads, pancreas, small intestine, placenta, ovary, uterus, testes, lung, and colon. In another embodiment, the disorder is a cancer. The cancer may be a primary tumor or a metastasis. The cancer may also be selected from the group consisting of breast cancer and esophageal cancer.

In one embodiment, the Grb7 ligand is a tyrosine kinase. The tyrosine kinase may be selected from the group consisting of HER2/ErbB2, ErbB4, PDGFR, epidermal growth factor receptor (EGFR), and Ret proto-oncogene. The Grb7 ligand may also be ErbB3. In another embodiment, the Grb7 ligand is a phosphatase. According to one embodiment, the phosphatase may be Syp/SHPTP2. The Grb7 ligand may also be an adaptor protein, and in yet another embodiment, the adaptor protein is Shc or Grb10. In yet a further embodiment, the Grb7 ligand may be an Fc epsilon receptor. In other embodiments, the Grb7 ligand may be a G7BP, such as but not limited to SEQ ID NO:1 through to SEQ ID NO:7, inclusive, SEQ ID NO:34; SEQ ID NO: 60 through to SEQ ID NO: 194, inclusive, SEQ ID NO:35, SEQ ID NO:39 through to SEQ ID NO:44, inclusive, and SEQ ID NO:47 through to SEQ ID NO:53, inclusive, or a functionally equivalent fragment thereof.

In one embodiment, the peptide is conjugated to an agent. The agent may be selected from the group consisting of a toxin, a radioactive molecule, a chemotherapeutic agent, an anti-angiogenic agent, an immunomodulatory agent, and a translocation agent. The translocation agent is defined herein as an agent that promotes the translocation of the Grb7 antagonists of the invention to various cellular locations, such as, but not limited to, the cytoplasm or the nucleus. Some preferred forms of translocation agents, are membrane translocating agents, which effect the transfer of the Grb7 antagonists from the extracellular environment to the intracellular environment, and nuclear translocation agents, which effect the transfer of the Grb7 antagonists from the cytoplasm to the nucleus. The translocation agent may be selected from the group consisting of a membrane translocating sequence, a transportan sequence, an Antennapedia sequence, a cyclic integrin-binding peptide, and a Tat-mediated peptide, or modified versions thereof, but is not so limited. Membrane translocating sequences are known in the art and it is well within the realm of the ordinary artisan to determine which is most suitable depending upon the desired outcome and cell type being targeted. According to another embodiment, the Grb7 antagonist may also be conjugated to a nuclear translocation sequence in order to effect nuclear delivery of the Grb7 antagonist.

In one embodiment, the peptide is administered systemically. In another embodiment, the peptide is administered locally. In yet another embodiment, the peptide is administered in a plurality of administrations.

In another aspect, a composition is provided comprising a peptide comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:34; SEQ ID NO: 60 through to SEQ ID NO: 194, inclusive, SEQ ID NO:35, SEQ ID NO:39, SEQ ID NO:40, SEQ ID NO:41, SEQ ID NO:42, SEQ ID NO:43, SEQ ID NO:44, SEQ ID NO:47, SEQ ID NO:48, SEQ ID NO:49, SEQ ID NO:50, SEQ ID NO:51, SEQ ID NO:52, and SEQ ID NO:53, or a functional equivalent thereof, including functionally equivalent fragments. The composition may further comprise a peptide consisting of an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:34; SEQ ID NO: 60 through to SEQ ID NO: 194, inclusive, SEQ ID NO:35, SEQ ID NO:39, SEQ ID NO:40, SEQ ID NO:41, SEQ ID NO:42, SEQ ID NO:43, SEQ ID NO:44, SEQ ID NO:47, SEQ ID NO:48, SEQ ID NO:49, SEQ ID NO:50, SEQ ID NO:51, SEQ ID NO:52, and SEQ ID NO:53. In one embodiment, the peptide is non-phosphorylated. In another embodiment, the peptide is cyclized or is capable of being cyclized via, for example, a disulfide bond, a thio-ether linkage or a peptide bond. In another embodiment, the peptide is conjugated to an agent. The agent may be selected from the group consisting of a toxin, a radioactive molecule, a chemotherapeutic agent, an anti-angiogenic agent, an immunomodulatory agent and a translocating agent.

In yet another aspect, an isolated nucleic acid molecule is provided comprising (a) a nucleic acid molecule which codes for a G7BP such as those comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:35, SEQ ID NO:39, SEQ ID NO:40, SEQ ID NO:41, SEQ ID NO:42, SEQ ID NO:43, SEQ ID NO:44, SEQ ID NO:47, SEQ ID NO:48, SEQ ID NO:49, SEQ ID NO:50, SEQ ID NO:51, SEQ ID NO:52, and SEQ ID NO:53, or functionally equivalent fragments thereof; (b) degenerates of (a); and (c) complements of (a) and (b).

In some aspects, the isolated nucleic acid molecule comprises a nucleotide sequence selected from the group consisting of SEQ ID NO:11, SEQ ID NO:12, SEQ ID NO:13, SEQ ID NO:14, SEQ ID NO:15, SEQ ID NO:16, and SEQ ID NO:17, and degenerates thereof.

The invention further provides in another aspect an expression vector comprising the afore-mentioned isolated nucleic acid molecule, operably linked to a promoter, and a host cell transformed or transfected with the expression vector.

In another aspect, a pharmaceutical preparation is provided comprising one or a combination of the afore-mentioned compositions and a pharmaceutically acceptable carrier. The pharmaceutical preparation and compositions may be in a sustained release vehicle.

In a further aspect, the invention provides a composition comprising an isolated agent that selectively binds to Grb7 and interferes with the binding of Grb7 to a peptide comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:34; SEQ ID NO: 60 through to SEQ ID NO: 194, inclusive, SEQ ID NO:35, SEQ ID NO:39, SEQ ID NO:40, SEQ ID NO:41, SEQ ID NO:42, SEQ ID NO:43, SEQ ID NO:44, SEQ ID NO:47, SEQ ID NO:48, SEQ ID NO:49, SEQ ID NO:50, SEQ ID NO:51, SEQ ID NO:52, and SEQ ID NO:53, or a functionally equivalent thereof, including functionally equivalent fragments. In one embodiment, the peptide is non-phosphorylated. In another embodiment, the isolated agent is a peptide itself. In yet another embodiment, the isolated agent is an antibody, or a fragment thereof. The antibody may be a humanized antibody or a chimeric antibody. In yet a further embodiment, the isolated agent is selected from the group consisting of a phage display library member, a synthetic peptide, a combinatorial chemistry library member, and a peptidomimetic. In important embodiments, the isolated agent is a small chemical compound.

In another aspect, a method is provided for screening a molecular library to identify a compound that modulates interaction between Grb7 and a peptide comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:34; SEQ ID NO: 60 through to SEQ ID NO: 194, inclusive, SEQ ID NO:35, SEQ ID NO:39, SEQ ID NO:40, SEQ ID NO:41, SEQ ID NO:42, SEQ ID NO:43, SEQ ID NO:44, SEQ ID NO:47, SEQ ID NO:48, SEQ ID NO:49, SEQ ID NO:50, SEQ ID NO:51, SEQ ID NO:52, and SEQ ID NO:53, or a functionally equivalent fragment thereof. The method comprises (1) performing a first assay between Grb7 and the peptide to obtain a first assay result; (2) performing a second assay between Grb7 and the peptide in the presence of a molecular library member to obtain a second assay result; and (3) comparing the first and second assay results to determine whether the molecular library member modulates interaction between Grb7 and the peptide. In some important embodiments, the Grb7 molecule is a Grb7-SH2 domain such as that used in the screening assays in the Examples. The screening assay may also include a pre-screen in which the library member is also tested for its ability to bind to Grb14-SH2 or Grb2-SH2 domains or the mutant Grb7-SH2 domain described herein.

In one embodiment, the molecular library is selected from the group consisting of a peptide library, a phage display library, a peptidomimetic library, a combinatorial chemistry library, and a synthetic peptide library. The screening method may further comprise selecting a molecular library that is suspected of containing a library member that modulates the interaction of Grb7 and a Grb7 ligand. The molecular library may contain from two to $10^{15}$ molecules and any integer number therebetween. According to one embodiment, the molecular library member is a phage display library member. The phage display library member may comprise an YXN amino acid sequence preferably selected from the group consisting of SEQ ID NO:8 (YAN), SEQ ID NO:9 (YEN), and SEQ ID NO:10 (YDN). The phage display library member may be non-phosphorylated, and it may be cyclized.

In one embodiment, the assay is a binding assay which detects binding of Grb7 to the peptide. In another embodiment, the assay is a signaling assay which detects signaling events following Grb7 binding to the peptide. In yet a further embodiment, the method further involves introducing the molecular library member into an animal model of a condition characterized by an abnormal or adverse interaction of Grb7 and one or more of its ligands and determining whether the molecular library member ameliorates symptoms of the condition.

In one embodiment, the peptide may be non-phosphorylated. In another embodiment, the peptide may be cyclized. In another embodiment, Grb7 or the peptide may be immobilized onto a solid support. According to one embodiment, Grb7 is present in the context of a cell. The cell may be selected from the group consisting of breast cancer cell and an esophageal cancer cell.

In another aspect, the invention provides a phage display library comprising Grb7 antagonists having a YXN amino acid sequence. "X" generally represents any amino acid residue, however, in important embodiments, the YXN amino acid sequence is selected from the group consisting of YAN (SEQ ID NO:8), YDN (SEQ ID NO:9), and YEN (SEQ ID NO:10), or functional equivalents thereof. In one embodiment, the amino acid sequence is YAN. In another embodiment, the amino acid sequence is YDN. And in still another embodiment, the amino acid sequence is YEN. In one embodiment, the peptides are non-phosphorylated (i.e., the tyrosine residue of the XYN motif is unphosphorylated). In another embodiment, the peptides are cyclic or are capable of being cyclized (i.e., they possess at least two cysteine residues sufficiently spaced from each other to allow a disulfide bond to from between them). The phage display library preferably comprises Grb7 antagonists that are 20 amino acids (or less) and, in certain embodiments, 12 amino acids (or less) in length.

The YXN motif which may be located at either of the ends, or internally to the peptide sequence. For example, the YXN sequence may be located at or near the end of the length of the peptide such as for example, starting at the +1 or +2 position or starting at the +9 or +10 position for a 12 amino acid peptide (relative to the length of the peptide).

In certain embodiments, the Grb7 antagonist has a sequence of $X_m$-YXN-$X_n$, wherein m and n can each be 0 through to 17 inclusive provided that the sum of m and n is equal to or less than 17 (resulting in a 20 amino acid peptide), and wherein X is an amino acid and is randomly and independently selected from every other X residue in the peptide. In some important embodiments, the peptide has flanking cysteine residues and the corresponding sequence is C-$X_a$-YXN-$X_b$-C (SEQ ID NO: 34; SEQ ID NO: 60 through to SEQ ID NO: 194, inclusive) wherein a and b can each be 0 through to 15 inclusive, provided that the sum of a and b is less than or equal to 15. Exemplary sequences of Grb7 antagonists may further comprise an amino acid sequence selected from the group consisting of C-XXX-YAN-XXX-C (SEQ ID NO:23), C-XXX-YDN-XXX-C (SEQ ID NO:24), C-XXX-YEN-XXX-C (SEQ ID NO:25), C-XXXX-YAN-XXX-C (SEQ ID NO:26), C-XXXX-YDN-XXX-C (SEQ ID NO:27), C-XXXX-YEN-XXX-C (SEQ ID NO:28), C-XXX-YAN-XXXX-C (SEQ ID NO:29), C-XXX-YDN-XXXX-C (SEQ ID NO:30), and C-XXX-YEN-XXXX-C (SEQ ID NO:31), but are not so limited.

BRIEF DESCRIPTION OF THE SEQUENCE LISTING

SEQ ID NO:1 is the amino acid sequence of G7BP-1.
SEQ ID NO:2 is the amino acid sequence of G7BP-2.
SEQ ID NO:3 is the amino acid sequence of G7BP-3.
SEQ ID NO:4 is the amino acid sequence of G7BP-4.
SEQ ID NO:5 is the amino acid sequence of G7BP-5.
SEQ ID NO:6 is the amino acid sequence of G7BP-6.
SEQ ID NO:7 is the amino acid sequence of G7BP-7.
SEQ ID NO:8 is the amino acid sequence of a consensus sequence of a Grb7 antagonist (i.e., YAN).
SEQ ID NO:9 is the amino acid sequence of a consensus sequence of a Grb7 antagonist (i.e., YEN).
SEQ ID NO:10 is the amino acid sequence of a consensus sequence of a Grb7 antagonist (i.e., YDN). SEQ ID NO:11 is the nucleotide sequence of a nucleic acid molecule which encodes G7BP-1.
SEQ ID NO:12 is the nucleotide sequence of a nucleic acid molecule which encodes G7BP-2.
SEQ ID NO:13 is the nucleotide sequence of a nucleic acid molecule which encodes G7BP-3.
SEQ ID NO:14 is the nucleotide sequence of a nucleic acid molecule which encodes G7BP-4.
SEQ ID NO:15 is the nucleotide sequence of a nucleic acid molecule which encodes G7BP-5.
SEQ ID NO:16 is the nucleotide sequence of a nucleic acid molecule which encodes G7BP-6.
SEQ ID NO:17 is the nucleotide sequence of a nucleic acid molecule which encodes G7BP-7.
SEQ ID NO:18 is the amino acid sequence of transportan.
SEQ ID NO:19 is the amino acid sequence of pAntennapedia.
SEQ ID NO:20 is the amino acid sequence of a membrane translocation sequence (MTS).
SEQ ID NO:21 is the amino acid sequence of a cyclic integrin-binding peptide.
SEQ ID NO:22 is the amino acid sequence of a tat-mediated peptide.
SEQ ID NO:23 is the amino acid sequence of a Grb7 antagonist.
SEQ ID NO:24 is the amino acid sequence of a Grb7 antagonist.
SEQ ID NO:25 is the amino acid sequence of a Grb7 antagonist.
SEQ ID NO:26 is the amino acid sequence of a Grb7 antagonist.
SEQ ID NO:27 is the amino acid sequence of a Grb7 antagonist.
SEQ ID NO:28 is the amino acid sequence of a Grb7 antagonist.
SEQ ID NO:29 is the amino acid sequence of a Grb7 antagonist.
SEQ ID NO:30 is the amino acid sequence of a Grb7 antagonist.
SEQ ID NO:31 is the amino acid sequence of a Grb7 antagonist.
SEQ ID NO:32 is the amino acid sequence of the GI peptide.
SEQ ID NO:33 is the amino acid sequence of a general formula for Grb7 antagonists.
SEQ ID NO:34 is the amino acid sequence of a general formula for Grb7 antagonists.
SEQ ID NO:35 is the amino acid sequence of the G7BP-4NA peptide.
SEQ ID NO:36 is the amino acid sequence of the G7BP-4 Ser peptide.
SEQ ID NO:37 is the amino acid sequence of the G7BP-4 Val peptide.
SEQ ID NO:38 is the amino acid sequence of the G7BP-4 Ser (NA) peptide.
SEQ ID NO:39 is the amino acid sequence of the G7BP-1NA peptide.
SEQ ID NO:40 is the amino acid sequence of the G7BP-2NA peptide.
SEQ ID NO:41 is the amino acid sequence of the G7BP-3NA peptide.
SEQ ID NO:42 is the amino acid sequence of the G7BP-5NA peptide.
SEQ ID NO:43 is the amino acid sequence of the G7BP-6NA peptide.
SEQ ID NO:44 is the amino acid sequence of the G7BP-2NA peptide.
SEQ ID NO:45 is the amino acid sequence of a PI3 kinase SH2 binding peptide.
SEQ ID NO:46 is the amino acid sequence of a non-phosphorylated peptide that mimics the ErbB2 site to which Grb7 binds.
SEQ ID NO:47 is the amino acids sequence of G7BP-1NATE.
SEQ ID NO:48 is the amino acids sequence of G7BP-2NATE.
SEQ ID NO:49 is the amino acids sequence of G7BP-3NATE.
SEQ ID NO:50 is the amino acids sequence of G7BP-4NATE.
SEQ ID NO:51 is the amino acids sequence of G7BP-5NATE.
SEQ ID NO:52 is the amino acids sequence of G7BP-6NATE.
SEQ ID NO:53 is the amino acids sequence of G7BP-7NATE.
SEQ ID NO:54 is the amino acid consensus sequence derived from the G7BP described herein.
SEQ ID NO:55 is the amino acid sequence of the endogenous Grb7 binding sequence in Shc.
SEQ ID NO:56 is the amino acid sequence of the endogenous Grb7 binding sequence in SHPTP2.
SEQ ID NO:57 is the amino acid sequence of the endogenous Grb7 binding sequence in ErbB2.
SEQ ID NO:58 is the amino acid sequence of the endogenous Grb7 binding sequence in cKit/Stem Cell Factor receptor.
SEQ ID NO:59 is the amino acid sequence of the endogenous Grb7 binding sequence in FAK Tyrosine Kinase.
SEQ ID NO: 60 through to SEQ ID NO: 194 are the amino acid sequences of a class of Grb7 antagonists.

Figure 1:
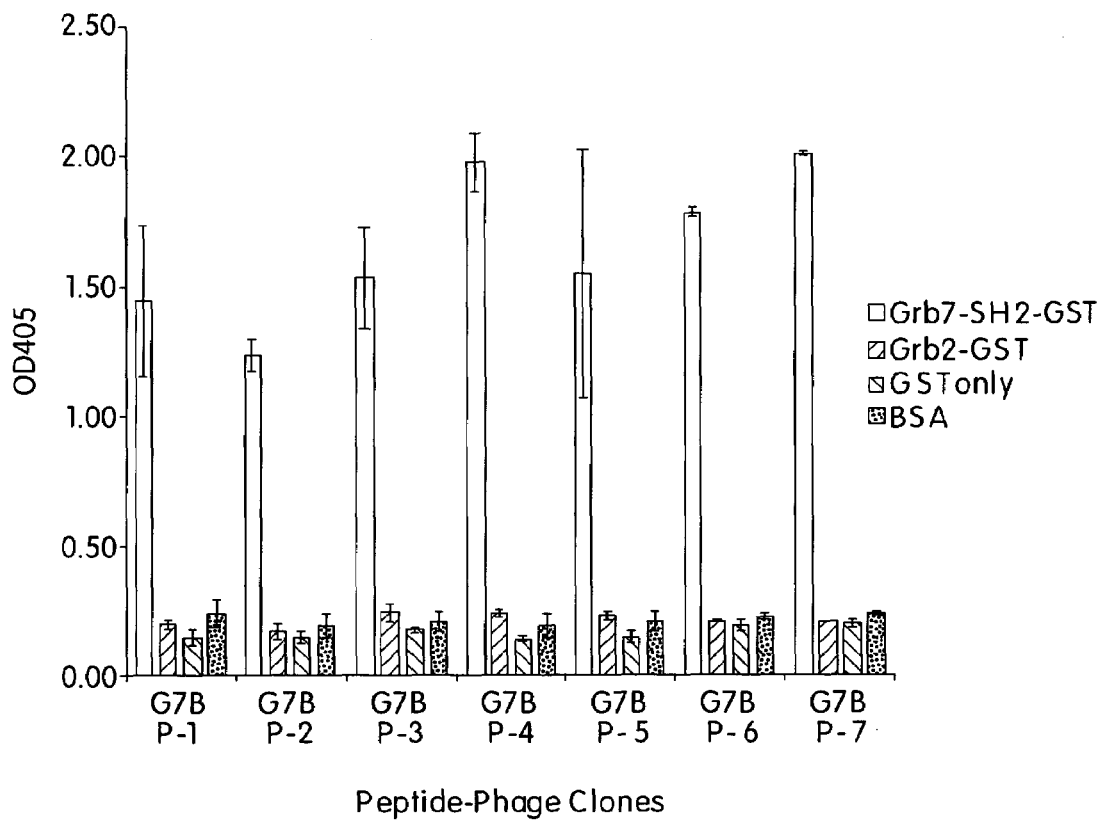
FIG. 1 is a histogram showing the binding of Grb7 binding peptides (G7BP) to the SH2 domain of human Grb7 by ELISA.

It is to be understood that the drawings are not required for enablement of the claimed invention.

DETAILED DESCRIPTION OF THE INVENTION

The invention relates in part to the identification and use of Grb7 antagonists which bind specifically to Grb7, preferably in the SH2 domain, and thereby prevent Grb7 from binding to its native ligands. More specifically, the invention provides, in part, peptides called Grb7 Binding Peptides (G7BP), (e.g., G7BP-1, G7BP-2, G7BP-3, G7BP-4, G7BP-5, G7BP-6, G7BP-7), and functional equivalents thereof, which bind to the Src-Homology Domain 2 (SH2) of Grb7 and, in doing so, inhibit the binding of Grb7 to one or more of its ligands. The invention embraces a variety of Grb7 binding peptides which may range in size from 4 to 30 amino acids. These peptides may be cyclic and may additionally be phosphorylated, but are not so limited. In preferred embodiments of the invention, the peptides are non-phosphorylated.

One particular category of Grb7 binding peptides is small cyclic molecules approximately 2 kilodaltons in size, containing 20 amino acids which are preferably non-phosphorylated. Examples include peptides having an amino acid sequence of SEQ ID NO:1 through to SEQ ID NO:7, inclusive. Another category of Grb7 binding peptides is modeled after the sequence of G7BP-4 peptide. These latter peptides are 12 amino acids in length, and they maintain the terminal cysteine residues of G7BP-4 peptide and demonstrate similar binding affinity as G7BP-4 in an ELISA binding assay. Examples include peptides having an amino acid sequence of SEQ ID NO:35, and SEQ ID NO:39 through to SEQ ID NO:44, inclusive. As discussed in the Examples, G7BP-1 through to G7BP-7 bind specifically to Grb7 and not to Grb2, nor to Grb 14, both of which are similar SH2 containing adaptor proteins.

Yet another category of peptides are those which retain the amino acid sequence between the terminal cysteines, yet lack either or both of the terminal cysteines. In some preferred embodiments, the C-terminal cysteines are present and contribute to the thioether bond, while the N-terminal cysteine is replaced with a different functional group to make the thioether bond. FIG. 9 illustrates the structure of one example of a thioether containing peptide of the invention (e.g., G7BP-4NATE), as well as examples of other thioether linkages that can be used to link the N and C termini of the peptides described herein (albeit in the context of another unrelated peptide (G1TE)). The thioether bond can also be created in peptides that retain the N-terminal cysteine and replace the C-terminal cysteine with a functional group. Those of ordinary skill will appreciate that these and other variations of thioether linkages can be used to create cyclic peptides comprising the amino acid sequences of SEQ ID NO:47 through to SEQ ID NO:53, inclusive.

Inhibition of the SH2 domain function of Grb7 has been attempted previously using phosphotyrosine-containing peptides. (Janes et al 1997, *J. Biol Chem* 272: 8490-8497.) The peptides disclosed herein possess several advantages over such previously described signal transduction inhibitors, including their relatively small size and their non-phosphorylated state. Their small size facilitates tissue and tumor targeting and penetration. Non-phosphorylated peptides are more stable than their phosphorylated counterparts in vivo, since they are not susceptible to endogenous phosphatase activity that targets residues such as phosphorylated tyrosines. The Grb7 binding peptides of the invention also offer improved cell penetration as they do not contain a charged residue on the tyrosine. Moreover, cyclic peptides can be more structurally stable than linear peptides.

Grb7 is an adapter protein which is involved in signal transduction within a cell. Adaptor proteins function in part by transmitting a signal from a phosphorylated compound, such as for example, a phosphorylated receptor tyrosine kinase, to a compound downstream in the signaling pathway. The majority of recognized native Grb7 ligands are signaling factors such as tyrosine kinases, phosphatases, and other adapter proteins. Grb7 binds to intracellular signaling factors or to the intracellular domains of some transmembrane signaling factors. Grb7 has several conserved domains including a proline rich domain, a Pleckstrin homology domain, and an SH2 domain. The SH2 domain of Grb7 is primarily responsible for recognizing and binding to phosphotyrosine residues of Grb7 ligands. Grb7 has been shown to bind to endogenous sites containing phosphotyrosine (pY) residues having the following amino acid sequences: pYVNV (in Shc) (SEQ ID NO:55), pYENV (in SHPTP2) (SEQ ID NO:56), pYVNQ (in erbB2) (SEQ ID NO:57), pYSNL (in cKit/Stem Cell Factor receptor) (SEQ ID NO:58) (Thommes et. al. Biochem J. 341:211-216 (1999)), and pYAEI (in FAK Tyrosine Kinase) (SEQ ID NO:59) (Han and Guan, J. Biol. Chem. 274:24425-24430 (1999)). It has not been recognized previously, however, that Grb7 can bind to non-phosphorylated sites.

Grb7 is normally expressed, at varying levels, in a number of normal tissues such as pancreas, placenta, kidney, small intestine, gonad tissues such as ovary, uterus, testes, and prostate, liver, lung, and colon. Grb7 is also overexpressed in several malignant tumors and cell lines, including those of breast and esophagus. In several breast cancer cells, Grb7 and erbB2, which are located near each other on chromosome 17q, are often co-amplified, thereby explaining the overexpression of Grb7 in these cells. ErbB2 overexpression is found in the tumors of 30% of breast cancer patients and this increase in expression correlates with poor patient prognosis. The combined overexpression of Grb7 and ErbB2 proteins in such tumors is likely to up-regulate a signaling pathway which plays an important role in their pathogenesis. (Janes et al., 1997, J Biol Chem 272: 8490-8497; Tanaka et al., 1997 Cancer Research 57:28-31) Grb7 is also found to be overexpressed along with EGFR in some tumors and cell lines, including esophageal tumor lines. (Stein et al., EMBO J., 13:1331-1340, 1994; Kishi et al., Biochem Biophys Res Commun 232:5-9, 1997; Tanaka et al., Cancer Research, 57:28-31 1997)

The invention involves, in various related and interconnected aspects, isolated G7BPs, functional equivalents and modifications and variants of the foregoing, unique fragments of the foregoing, nucleic acid molecules encoding the foregoing, as well as diagnostics and therapeutics relating thereto.

In one aspect, the invention provides isolated peptides having an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:34; SEQ ID NO: 60 through to SEQ ID NO: 194, inclusive, SEQ ID NO:35, SEQ ID NO:39, SEQ ID NO:40, SEQ ID NO:41, SEQ ID NO:42, SEQ ID NO:43, SEQ ID NO:44, SEQ ID NO:47, SEQ ID NO:48, SEQ ID NO:49, SEQ ID NO:50, SEQ ID NO:51, SEQ ID NO:52, and SEQ ID NO:53, as well as functionally equivalent fragments thereof. Inhibiting the function of Grb7 using anti-sense DNA constructs has been shown to inhibit invasion of cancer cells in vitro (Tanaka et al. 1997. Cancer Research 57:28-31). By binding to the SH2 domain of Grb7, these peptides can inhibit the function of Grb7 by, at a minimum, preventing the association of Grb7 with its naturally occurring ligands, such as for example ErbB2 and ErbB3. Specific inhibitors of Grb7 are useful in elucidating the complete function and exact role of Grb7 in cancer progression, as well as in the development of cancer therapeutics which target Grb7. Using the peptide-phage display technology described herein, peptides can be more rapidly produced with less cost than other specific tumor targeting agents such as antibodies. Accordingly, the discovery of the lead compounds described herein was significantly faster and less expensive than traditional methods of lead discovery.

In important embodiments, the Grb7 antagonists are non-phosphorylated peptides. A non-phosphorylated peptide is a peptide which is not phosphorylated at least at the tyrosine residue of the XYN (e.g., the YAN, YDN or YEN) amino acid motif. A non-phosphorylated peptide also generally does not possess a phosphorus group on one or more of its serine, threonine or tyrosine residues.

In other important embodiments, the peptides are cyclic or are capable of being cyclized. This can be achieved by the presence of at least two cysteine residues in the peptides, thereby forming a disulfide linkage between the cysteine residues, but it is not so limited. The peptide can also be made cyclic by the placement of at least one cysteine residue on the N-terminal arm of the peptide and at least one other cysteine on the C-terminal arm of the peptide. It is not necessary that the cysteine residues be located at the ends of the peptides (i.e., at the first and last amino acid positions). However, preferably the cysteines are located on opposite sides of the YXN motif. As an example, the cysteine residues are positioned on opposite sides of the YAN, YDN or YEN motif, and are spaced far enough apart from each other to allow for a disulfide bond to be formed (e.g., with 4, 5, 6, 7, 8, 9, 10, 11, 12, 13, 14, 15, 16, 17, 18, 19, 20 or more residues in between the two cysteine residues). The peptides having amino acid sequences of SEQ ID NO:1 through to SEQ ID NO:7 are examples of peptides in which the disulfide bonded cysteines are located internally, with 4 amino acids separating each of the cysteines from the end of the peptide. In some instances, it may be preferable to substitute thioether linkages for the disulfide bond produced between cysteine residues. Such a modification is described in PCT patent application WO 98/02176 (PCT/US97/12501), and in Oligino et al., 1997, J Mol Chem 272:29046-29052 and Lou et al., 1999, Arch Biochem Biophys, 372: 309-314. In still other embodiments, the linkage may be a peptide linkage between the two arms of the peptide. In all these embodiments, preferably the YXN sequence is located within the loop created by the linkage. Other linkages that are useful include linkage between homocysteine residues located on both the N-terminal and the C-terminal arms.

It is to be understood that the invention embraces other varieties of linkages known in the art for the purpose of producing a cyclic peptide. Examples of other suitable linking molecules which can be used include bifunctional crosslinker molecules. The crosslinker molecules may be homobifunctional or heterobifunctional, depending upon the nature of the molecules to be conjugated. Homobifunctional cross-linkers have two identical reactive groups. Heterobifunctional cross-linkers are defined as having two different reactive groups that allow for sequential conjugation reaction. Various types of commercially available crosslinkers are reactive with one or more of the following groups: primary amines, secondary amines, sulphydryls, carboxyls, carbonyls and carbohydrates. Examples of amine-specific cross-linkers are bis(sulfosuccinimidyl) suberate, bis[2-(succinimidooxycarbonyloxy)ethyl] sulfone, disuccinimidyl suberate, disuccinimidyl tartarate, dimethyl adipimate.2 HCl, dimethyl pimelimidate.2 HCl, dimethyl suberimidate.2 HCl, and ethylene glycolbis-[succinimidyl-[succinate]]. Cross-linkers reactive with sulfhydryl groups include bis-maleimidohexane, 1,4-di-[3'-(2'-pyridyldithio)-propionamido)]butane, 1-[p-azidosalicylamido]-4-[iodoacetamido] butane, and N-[4-(p-azidosalicylamido) butyl]-3'-[2'-pyridyldithio]propionamide. Crosslinkers preferentially reactive with carbohydrates include azidobenzoyl hydrazine. Crosslinkers preferentially reactive with carboxyl groups include 4-[p-azidosalicylamido]butylamine. Heterobifunctional cross-linkers that react with amines and sulfhydryls include N-succinimidyl-3-[2-pyridyldithio]propionate, succinimidyl[4-iodoacetyl]aminobenzoate, succinimidyl 4-[N-maleimidomethyl] cyclohexane-1-carboxylate, m-maleimidobenzoyl-N-hydroxysuccinimide ester, sulfosuccinimidyl 6-[3-[2-pyridyldithio]propionamido]hexanoate, and sulfosuccinimidyl 4-[N-maleimidomethyl]cyclohexane-1-carboxylate. Heterobifunctional cross-linkers that react with carboxyl and amine groups include 1-ethyl-3-[[3-dimethylaminopropyl] carbodiimide hydrochloride. Heterobifunctional cross-linkers that react with carbohydrates and sulfhydryls include 4-[N-maleimidomethyl]-cyclohexane-1-carboxylhydrazide.2 HCl, 4-(4-N-maleimidophenyl)-butyric acid hydrazide.2 HCl, and 3-[2-pyridyldithio]propionyl hydrazide. The cross-linkers are bis-[β-4-azidosalicylamido)ethyl]disulfide and glutaraldehyde. Amine or thiol groups may be added at any nucleotide of a synthetic nucleic acid so as to provide a point of attachment for a bifunctional crosslinker molecule. The nucleic acid may be synthesized incorporating conjugation-competent reagents such as Uni-Link AminoModifier, 3'-DMT-C6-Amine-ON CPG, AminoModifier II, N-TFA-C6-AminoModifier, C6-ThiolModifier, C6-Disulfide Phosphoramidite and C6-Disulfide CPG (Clontech, Palo Alto, Calif.). The peptides of the invention can also comprise one or more non-peptide linkages in their backbones.

As used herein with respect to polypeptides, the term "isolated" means separated from its native environment in sufficiently pure form so that it can be manipulated or used for any one of the purposes of the invention. Thus, "isolated" means sufficiently pure to be used (i) to raise and/or isolate antibodies, (ii) as a reagent in an assay, or (iii) for sequencing, etc.

The G7BPs of the invention can be produced in a number of ways. The G7BP may be made synthetically using a peptide synthesizer. Alternatively, an expression vector which incorporates a nucleic acid molecule encoding a G7BP, such as SEQ ID NO:11 through to SEQ ID NO:17 or degenerates thereof, may be introduced into cells to cause production of the G7BP. In another method, mRNA transcripts encoding the G7BPs may be microinjected or otherwise introduced into cells to cause production of the encoded peptide. Translation of G7BP mRNA in cell-free extracts such as the reticulocyte lysate system also may be used to produce G7BPs. Those skilled in the art also can readily follow known methods for isolating G7BPs. These include, but are not limited to, immunochromatography, HPLC, size-exclusion chromatography, and ion-exchange chromatography. In a preferred embodiment, the peptides are identified using a phage display technology as described in the Examples and in PCT patent application WO98/02176 (PCT/US97/12501).

Unique fragments of the isolated G7BPs are also provided. A unique fragment of a Grb7 binding peptide, in general, has the features and characteristics of unique fragments of nucleic acid molecules as discussed herein. As will be recognized by those skilled in the art, the size of the unique fragment will depend upon factors such as whether the fragment constitutes a portion of a conserved motif such as for example the Y-X-N motif common to the G7BPs disclosed herein. Thus, some regions of SEQ ID NO:1 through to SEQ ID NO:7, SEQ ID NO:34; SEQ ID NO: 60 through to SEQ ID NO: 194, inclusive, SEQ ID NO:35, SEQ ID NO:39, SEQ ID NO:40, SEQ ID NO:41, SEQ ID NO:42, SEQ ID NO:43, SEQ ID NO:44, SEQ ID NO:47, SEQ ID NO:48, SEQ ID NO:49, SEQ ID NO:50, SEQ ID NO:51, SEQ ID NO:52 and SEQ ID NO:53 will require longer segments to be unique while others will require only short segments, typically between 5 and 12 amino acids (e.g., 5, 6, 7, 8, 9, 10, 11 and 12 amino acids long or more, including each integer up to the full length). Virtually any segment of SEQ ID NO:1 through to SEQ ID NO:7 inclusive, SEQ ID NO:35, SEQ ID NO:39 through to SEQ ID NO:44 inclusive, and SEQ ID NO:47 through to SEQ ID NO:53 inclusive, that is 9 or more amino acids in length will be unique.

Unique fragments of a peptide preferably are those fragments which retain the ability to bind to Grb7 and more preferably to preclude or inhibit the binding of Grb7 to one or more of its ligands. These latter unique fragments are considered functionally equivalent fragments. Other useful functional capabilities which can be retained in a unique fragment of a polypeptide include useful activity in a screening assay for further Grb7 antagonists, or interaction with antibodies. Antibodies so identified may be used in order to identify peptides or other small molecules that are structurally similar (including charge similarity) to the specific peptides disclosed herein. A preferred subset of unique fragments will also be capable of inhibiting cell growth in cells which possess abnormal or adverse interaction of Grb7 with its ligands. Another important activity is the ability of the unique fragment to act as a signature for identifying polypeptides which comprise the amino acid sequences selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:35, SEQ ID NO:39, SEQ ID NO:40, SEQ ID NO:41, SEQ ID NO:42, SEQ ID NO:43, SEQ ID NO:44, SEQ ID NO:47, SEQ ID NO:48, SEQ ID NO:49, SEQ ID NO:50, SEQ ID NO:51, SEQ ID NO:52 and SEQ ID NO:53. Such polypeptides may be native binding partners of Grb7, and more preferably, may be native inhibitory binding partners of Grb7. Those skilled in the art are well versed in methods for selecting unique amino acid sequences. A comparison of the sequence of the fragment to those in known databases is all that is typically required. Preferably, the unique fragment is unique in humans, i.e., it is long enough to assure that its precise sequence is not found in other molecules encoded by the human genome which have been identified and publicly disclosed as of the date of invention and/or the filing date of this application.

Unique fragments, however, exclude fragments completely composed of the amino acid sequences of any of GenBank accession numbers listed in Table 1 (see below) or other previously published sequences as of the filing date of this application or the date of the invention. A fragment which is completely composed of a sequence described in a GenBank deposit of Table 1 is one which does not include any of the amino acids unique to the sequences of the invention. Thus, a unique fragment must contain an amino acid sequence other than the exact sequence of those in GenBank or fragments thereof. The difference may be an addition, deletion or substitution with respect to all or part of the GenBank sequence or it may be a sequence wholly separate from the GenBank sequence.

The G7PBs disclosed herein will be useful as is or as leads for developing further Grb7 antagonists. Grb7 antagonists may be identified as variants of the G7BPs described herein or alternatively they may be produced in a more random fashion and identified via assays which employ G7BPs as competitive inhibitors of Grb7 binding or signaling.

Thus, the invention embraces variants of the G7BPs described above. As used herein, a "variant" of a G7BP is a peptide or peptidomimetic which contains one or more modifications to the primary amino acid sequence of a G7BP. The invention embraces variants of G7BP which possess substituents at various positions. Modifications to the G7BPs which preserve the size, structure, and charge distribution of the G7BP, particularly at the most conserved residues (such as the YXN motif), are preferred in some embodiments. A person of ordinary skill in the art is capable of determining the size, structure, and charge distribution characteristics of the G7BPs disclosed herein and of designing other putative inhibitory agents based on this knowledge. For example, glutamine (Glu) residues may be replaced with α-aminoadipate molecules and tyrosine positions may be substituted with 4-carboxymethyl-Phe.

In preferred embodiments, the variants are functional equivalents of G7BPs. As used herein, a functional equivalent of a G7BP is an antagonist which is able to function in a similar manner to a G7BP in binding to Grb7 and inhibiting Grb7 association (i.e., binding) with its ligand or in disrupting a pre-formed complex of Grb7 and its ligand. The ability of the agent to bind to Grb7 specifically, to preclude binding of Grb7 to one or more of its ligands, and to disrupt Grb7 binding to its ligands can be determined using the binding assays described herein or others known in the art. The functional equivalence of a compound so generated can be deduced by performing screening assays similar to those described in the Examples in which the ability of the agent to bind to Grb7-SH2 domains, mutant Grb7-SH2 domains, Grb2-SH2 domains and Grb14-SH2 domains is tested either concurrently or consecutively. The preferred functional equivalents are those which bind specifically to Grb7-SH2 domains but not to mutant Grb7-SH2 domains, Grb2-SH2 domains or Grb14-SH2 domains. Functional equivalence refers to an equivalent activity (e.g., binding to Grb7), however it also embraces variation in the level of such activity. For example, a functional equivalent is a variant that binds to Grb7 with lesser, equal, or greater affinity than the G7BPs described herein, provided that the variant is still useful in the invention (i.e., it binds to Grb7 and inhibits Grb7 association with Grb7 ligands or disrupts a pre-formed complex of Grb7 and a Grb7 ligand). Thus, as an example, the G7BP4 (NA) peptide is a functional equivalent of G7BP-4 as shown in the Examples. The functional equivalent of a G7BP may be peptide, non-peptide or chimeric in nature. The synthesis of such functionally equivalent variants is described below. In some preferred instances, a functional equivalent mimics the G7BPs of the invention with respect to size, structure, and charge distribution.

The functional equivalents of the G7BPs provided herein, including unique fragments of the G7BPs, may differ from the amino acid sequences provided herein at 1, 2, 3, 4, 5, 6, 7, 8, 9, or more positions. Alternatively, the functional equivalents may possess greater than 95% identity, greater than 90% identity, greater than 80% identity, greater than 75% identity, greater than 60% identity, or greater than 50% identity with any of the G7BP described herein. In preferred embodiments, the amino acid differences between the G7BPs described herein and their functional equivalents exist at a location other than the central YXN motif.

The skilled artisan will realize that conservative amino acid substitutions may also be made in G7BPs to provide functionally equivalent variants of the foregoing peptides. As used herein, a "conservative amino acid substitution" refers to an amino acid substitution which does not alter the relative charge or size characteristics of the peptide or protein in which the amino acid substitution is made. Variants can be prepared according to methods for altering peptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the G7BPs include conservative amino acid substitutions of SEQ ID NO:1 through to SEQ ID NO:7 inclusive, SEQ ID NO:35, SEQ ID NO:39 through to SEQ ID NO:44 inclusive, and SEQ ID NO:47 through to SEQ ID NO:53 inclusive. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Phosphorus and non-phosphorus based analogs may be used in the variants of the G7BPs. Phosphorotyrosine mimetics, which may or may not contain phosphorus, sometimes have better cell penetration properties than phosphotyrosine-containing peptides. Unlike phosphotyrosine-containing peptides, most of these mimetics are not susceptible to endogenous phosphatase activity. Tyrosine analogs which can be used in place of the tyrosine residue in the G7BPs of the invention include phenylalanine (Phe), pentafluoro phenylalanine (PfPhe), 4-carboxymethyl-L-phenylalanine (cmPhe), 4-carboxydifluoromethyl-L-phenylalanine ($F_2$cmPhe), 4-phosphonomethyl-phenylalanine (Pmp), (difluorophosphonomethyl)phenylalanine ($F_2$Pmp), O-malonyl-L-tyrosine (malTyr or OMT), and fluoro-O-malonyltyrosine (FOMT). In some embodiments, phosphonate-based mimetics which substitute a methylene unit for the tyrosyl phosphate ester bond are preferred. These substitutions are well known in the art and are described in, inter alia, Burke et al., 1999, Bioorg Med Chem Lett, 9:347-352; Long et al., 1999, Biochem Biophys Res Commun 264:902-908; Yao et al., 1999, J. Med Chem, 42:25-35; Ye et al., 1995, J Med Chem, 38:4270-4275.

In some instances, glutamic acid residues can be modified to possess an additional methylene group or they may simply be substituted with α-amino-adipate (Adi). Such modifications have been found to increase binding affinity in Grb2 antagonists. (Long et al., 1999, Biochem. Biophys. Res. Commun. 264:902-908) In another study, Yao et al. reported the synthesis and use of Noc-oxalyl groups in Grb2 inhibitory molecules. (Yao, et al., J. Med. Chem., 42:25-35, 1999) Other residues which may be incorporated into the G7BP variants include the non-naturally occurring amino acid 1-aminocyclohexylcarboxylic acid ($Ac_6c$) (e.g., at the +1 position relative to the pY position of 0) and 3-(2-hydroxynaphtalen-1-yl)-propyl, both of which have been incorporated into CGP78850, a Grb2 antagonist variant synthesized and reported by Gay et al. (Gay et al., Int. J. Cancer, 83:235-241, 1999). Other residues include non-naturally occurring amino acids, such as 2-azetidinecarboxylic acid or pipecolic acid (which have 6-membered, and 4-membered ring structures respectively) for proline residues, and S-ethylisothiourea, 2-$NH_2$-thiazoline and 2-$NH_2$-thiazole. Compounds having a Pmp residue in the 0 position (i.e., replacing the tyrosine) and an $Ac_6c$ residue at the +1 position (relative to the tyrosine) may be particularly useful as G7BP variants, particularly since this combination has been reported to antagonize Grb2. (Schoepfer, et al., Bio. Med. Chem. Lett. 9:221-226, 1999) Also useful in the synthesis of G7BP variants is the use of an asparagine residue substituted with 3-indolyl-propyl at the C terminal carboxyl group.

It will be apparent to one of ordinary skill in the art that the invention embraces the synthesis of a wide variety of G7BP variants having any combination of amino acid analogs and/or peptidomimetic residues as described above and as are known in the art. (See, for example, Burke, et al., Bio. Med. Chem. Lett., 9:347-352, 1999). Further potential modifications of G7BPs envisioned by the invention include modifications of cysteines, histidines, lysines, arginines, tyrosines, glutamines, asparagines, prolines, and carboxyl groups as are well known in the art and are described in U.S. Pat. No. 6,037,134. Synthesis of the afore-mentioned variants is described in the cited references and is well within the realm of one of ordinary skill in the art.

The G7BPs may be modified to introduce or stabilize certain structural features. As an example, other groups have reported the ability to introduce structural features including, but not limited to, β-bends into inhibitory peptides of other SH2 containing proteins. In particular, a peptide capable of blocking Grb2 binding to its endogenous ligand was synthesized with a 1-aminocyclohexanecarboxylic acid in the pTyr +1 position. (Garcia-Echeverria, J Med Chem. 1998, 41(11):1741-4.) In other embodiments and as discussed above, it may be preferred that the G7BP variants possess a stable cyclic structure. This may be achieved by generating thio-ether cyclized peptides (to replace the disulfide bonds on the presently disclosed G7BPs) such as those reported by Oligino et al. and Lou et al. (Oligino et al., J. Biol. Chem. 272:29046-29052, 1997; Lou et al., Arch Biochem Biophys, 372:309-314, 1999) This modification ensures a stable conformation which, in some instances, may be optimal for Grb7 inhibition. Similarly, the cyclic structure can also be formed via other linkages such as, but not limited to, peptide bonds.

Known binding peptides, such as the G7BPs described herein, may also be subjected to directed or random chemical modifications such as acylation, alkylation, esterification, amidification, etc. to produce structural analogs which may function as antagonists.

In an alternative approach, Grb7 antagonists can be rationally designed. One way of doing this involves modeling the binding site of Grb7 complexed with or without, for example, a G7BP, using X-ray crystallography or NMR or Raman spectroscopy. In addition, the successful use of computer-based algorithms to model binding sites is discussed in U.S. Pat. No. 5,741,713, the entire contents of which are incorporated by reference herein. The strategy usually involves computer-based structural modeling of the binding site including its conformation, reactive groups, and charge groups, and generally requires knowledge of the three-dimensional structure of the binding site obtained by X-ray crystallography or NMR or Raman spectroscopy. With this knowledge, the requirements for a useful antagonist can be determined, and rational design of synthetic antagonists can follow.

Rational design of G7BP variants can also be accomplished by comparing and contrasting the amino acid sequences of the various G7BPs disclosed herein (e.g., SEQ ID NO:1 through SEQ ID NO:7, inclusive). A study of the amino acid sequence as well as a structural analysis and subsequent comparison with peptides which bind to other Grb family members (e.g., Grb2 or Grb14) and not Grb7, can elucidate the amino acid residues and three-dimensional conformation involved in the specificity of inhibition. Random or directed mutation of the putative amino acid residues involved in the recognition and/or binding of the peptide to Grb7 can help to identify further binding and inhibitory peptides, as described herein.

One of skill in the art will be familiar with methods for predicting the effect on protein conformation of a change in protein sequence, and can thus "design" a variant which functions as an antagonist according to known methods. One example of such a method is described by Dahiyat and Mayo in Science 278:82-87, 1997, which describes the design of proteins de novo. The method can be applied to a known peptide to vary only a portion of the amino acid sequence. By applying the computational methods of Dahiyat and Mayo, specific variants of G7BPs can be proposed and tested to determine whether the variant retains a desired conformation and the ability to bind and inhibit Grb7. Similarly, Blake (U.S. Pat. No. 5,565,325) teaches the use of known structures to predict and synthesize variants with similar or modified function.

Other methods for preparing or identifying peptides which bind to a particular target are known in the art. Molecular imprinting, for instance, may be used for the de novo construction of macromolecular structures such as peptides which bind to a particular molecule. See, for example, Kenneth J. Shea, Molecular Imprinting of Synthetic Network Polymers: The De Novo synthesis of Macromolecular Binding and Catalytic Sites, TRIP Vol. 2, No. 5, May 1994; Klaus Mosbach, Molecular Imprinting, Trends in Biochem. Sci., 19(9) January 1994; and Wulff, G., in Polymeric Reagents and Catalysts (Ford, W. T., Ed.) ACS Symposium Series No. 308, pp 186-230, American Chemical Society (1986). One method for preparing mimics of G7BPs involves the steps of: (i) polymerization of functional monomers around a known substrate (i.e., the template or in this case, the G7BP) that exhibits a desired activity; (ii) removal of the template molecule; and then (iii) polymerization of a second class of monomers in the void left by the template, to provide a new molecule which exhibits one or more desired properties which are similar to that of the template. In addition to preparing peptides in this manner other binding molecules such as polysaccharides, nucleosides, drugs, nucleoproteins, lipoproteins, carbohydrates, glycoproteins, steroids, lipids, and other biologically active materials can also be prepared. This method is useful for designing a wide variety of biological mimics that are more stable than their natural counterparts, because they are typically prepared by the free radical polymerization of functional monomers, resulting in a compound with a nonbiodegradable backbone. Other methods for designing such molecules include, for example, drug design based on structure activity relationships which require the synthesis and evaluation of a number of compounds and molecular modeling.

In important embodiments, peptide variants are made and screened using the phage display technology described herein. Peptide variants can be synthesized using degenerate oligos which are biased for a sequence encoding a known peptide that binds to the SH2 domain (such as, for example, YXN). In a preferred embodiment, the phage library are made using the Fuse5 vector. (Scott and Smith, 1990, 249:386-90; Smith and Scott, Methods Enzymol 1993, 217: 228-57) These techniques are well known in the art.

Conservative amino-acid substitutions in the amino acid sequence of G7BPs to produce functionally equivalent variants of G7BPs may be made by alteration of nucleic acid molecules encoding G7BPs (e.g., SEQ ID NO:11 through to SEQ ID NO:17, inclusive). Such substitutions can be made by a variety of methods known to one of ordinary skill in the art. For example, amino acid substitutions may be made by PCR-directed mutation, site-directed mutagenesis according to the method of Kunkel (Kunkel, Proc. Nat. Acad. Sci. U.S.A. 82: 488-492, 1985) or by chemical synthesis of a nucleic acid molecule encoding a G7BP. The activity of functionally equivalent fragments of G7BPs can be tested by cloning the nucleic acid molecule encoding the altered G7BP into a bacterial or mammalian expression vector, introducing the vector into an appropriate host cell, expressing the altered G7BP, and testing for a functional capability of the G7BPs as disclosed herein. In some embodiments, however, due to the size of the G7BPs, it may be more convenient to synthesize the variant peptides using a peptide synthesizer such as those commercially available. In preferred embodiments, the peptides are synthesized and screened using phage display technology, as described herein.

Variants can include G7BP polypeptides which are modified specifically to alter a feature of the polypeptide unrelated to its binding and inhibitory activity. For example, cysteine residues can be substituted or deleted to prevent disulfide linkages, which may be desirable if other means of linkage are available in the peptide. Similarly, certain amino acids can be changed to enhance expression of a G7BP by eliminating proteolysis by proteases in an expression system (e.g., dibasic amino acid residues in yeast expression systems in which KEX2 protease activity is present).

Modifications made to the nucleic acid molecules which encode G7BPs can include deletions, point mutations, truncations, potentially resulting in amino acid additions, deletions or substitutions and can serve to: 1) enhance a property of a G7BP, such as peptide stability in an expression system or the stability of peptide-protein binding; 2) provide a novel activity or property to a G7BP, such as addition of an antigenic epitope, a detectable moiety or a localization signal sequence (such as the translocation sequences discussed herein); or 3) to provide equivalent or better binding to Grb7. Alternatively, modifications can be made directly to the peptide, such as by cleavage, addition of a linker molecule, addition of a detectable moiety, such as biotin, addition of a fatty acid, and the like.

Modifications also embrace fusion proteins comprising all or part of the G7BP amino acid sequences (e.g., SEQ ID NO:1 through to SEQ ID NO:7 inclusive, SEQ ID NO:35, SEQ ID NO:39 through to SEQ ID NO:44 inclusive, and SEQ ID NO:47 through to SEQ ID NO:53 inclusive). As discussed herein, one preferred modification is the fusion of the G7BP amino acid sequence with a translocation agent capable of transporting G7BP into the cell cytoplasm, or a fusion of the G7BP amino acid sequence with a nuclear translocation agent capable of transporting G7BP into the nucleus of the cell. Examples of translocation agents include, but are not limited to, membrane translocating sequence, a transportan sequence, an Antennapedia sequence, a cyclic integrin-binding peptide, and a Tat-mediated peptide. Nuclear translocation sequences (or signals) include but are not limited to importing-β sequence and β-catenin sequence (Lee et al., 2000, J Mol Biol, 302:251-264), ETO/MTG8 sequence (Odaka et al., 2000, Oncogene, 19:3584-3597, cytomegalovirus DAN-binding protein pUL56 sequence (Giesen et al., 2000, J Gen Virol, 81: Pt 9:2231-2244), and the interferon-γ sequence (Subramaniam et al., 2000, J Cell Sci, 113: Pt15:2771-2781).

Mutations of nucleic acid molecules which encode G7BPs preferably preserve the amino acid reading frame of the coding sequence, and preferably do not create regions in the nucleic acid molecule which are likely to hybridize to form secondary structures, such a hairpins or loops, which can be deleterious to expression of the variant peptide.

Mutations can be made by selecting an amino acid substitution, or by random mutagenesis of a selected site in a nucleic acid molecule which encodes the peptide. Variant polypeptides are then expressed and tested for one or more activities to determine which mutation provides a variant peptide with the desired properties. Further mutations can be made to variants (or to non-variant G7BPs) which are silent as to the amino acid sequence of the peptide, but which provide preferred codons for translation in a particular host. The preferred codons for translation of a nucleic acid molecule in, e.g., E. coli, are well known to those of ordinary skill in the art. Still other mutations can be made to the noncoding sequences of G7BP nucleic acid molecules to enhance expression of the peptide.

Grb7 antagonists can be synthesized from peptides or other biomolecules including but not limited to saccharides, fatty acids, sterols, isoprenoids, purines, pyrimidines, derivatives or structural analogs of the above, or combinations thereof, and the like. Phage display libraries and chemical combinatorial libraries can be used to develop and select synthetic Grb7 antagonists. Also envisioned in the invention is the synthesis of Grb7 antagonists made from non-natural amino acids, peptoids, random bio-oligomers (U.S. Pat. No. 5,650,489), benzodiazepines, diversomeres such as dydantoins, benzodiazepines, and dipeptides, non-peptidal peptidomimetics with a beta-D-glucose scaffolding, oligocarbamates or peptidyl phosphonates.

Many if not all of these compounds can be synthesized using recombinant or chemical library approaches. A vast array of candidate antagonists can be generated from libraries of synthetic or natural compounds. Libraries of natural compounds in the form of bacterial, fungal, plant and animal extracts are available or can readily be produced. Natural and synthetically produced libraries and compounds can be readily modified through conventional chemical, physical, and biochemical means.

Methods for preparing libraries of molecules are well known in the art and many libraries are commercially available. Libraries of interest in the invention include peptide libraries, randomized oligonucleotide libraries, synthetic organic combinatorial libraries, and the like. Degenerate peptide libraries can be readily prepared in solution; peptides libraries can also be in immobilized form as bacterial flagella display libraries or as phage display libraries. Peptide ligands can be selected from combinatorial libraries of peptides containing at least one amino acid. Libraries can be synthesized of peptoids and non-peptide synthetic moieties. Such libraries can further be synthesized which contain non-peptide synthetic moieties which are less subject to enzymatic degradation compared to their naturally-occurring counterparts. Libraries are also meant to include, for example, but are not limited to peptides-on-plasmid libraries, polysome libraries, aptamer libraries, synthetic peptide libraries, synthetic small molecule libraries, and chemical libraries. The libraries can also comprise cyclic carbon or heterocyclic structure and/or aromatic or polyaromatic structures substitutions.

The methods of the invention utilize this library technology to identify small molecule antagonists including small peptides which bind to Grb7 SH2 interaction sites. One advantage of using libraries for inhibitor identification is the facile manipulation of millions of different putative candidates of small size in small reaction volumes (i.e., in synthesis and screening reactions). Another advantage of libraries is the ability to synthesize antagonists which might not otherwise be attainable using naturally occurring sources, particularly in the case of non-peptide moieties.

Synthetic DNA and RNA libraries are also routinely used in the art. For instance, Ellington and Szostak describe the use of random polynucleotide libraries to identify novel ligands (Ellington and Szostak, Nature, 346, 818-822 (1990)). Accordingly, modifications which create G7BP variants can be made at the level of the nucleic acid molecule sequences which encode the peptides, as described above. Amino acid substitutions may be made by PCR-directed mutation, site-directed mutagenesis according to the method of Kunkel (Kunkel, Proc. Nat. Acad. Sci. U.S.A. 82: 488-492, 1985), or by chemical synthesis of a nucleic acid molecule encoding a G7BP variant.

Small molecule combinatorial libraries may also be generated. A combinatorial library of small organic compounds is a collection of closely related analogs that differ from each other in one or more points of diversity and are synthesized by organic techniques using multi-step processes. Combinatorial chemistry libraries include a large number of small organic compounds. One type of combinatorial library is prepared by means of parallel synthesis methods to produce a compound array. A "compound array" as used herein is a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in PCT published patent application WO95/18972, published Jul. 13, 1995 and U.S. Pat. No. 5,712,171 granted Jan. 27, 1998 and its corresponding PCT published patent application WO96/22529, which are hereby incorporated by reference.

In certain embodiments, the libraries may have at least one constraint imposed upon the displayed peptide sequence. A constraint includes, e.g., a positive or negative charge, hydrophobicity, hydrophilicity, a cleavable bond, and the necessary residues surrounding that bond, one or more cysteines for producing a cyclic peptide and combinations thereof. In certain embodiments, more than one constraint is present in each of the peptide sequences of the library. An example of an imposed constraint is the length of the peptide. In certain important embodiments, peptides that are 4-20 amino acids in length are preferred. An example of an imposed constraint is the presence of cysteine residues at the ends or at least on the arms of the peptide. Yet another imposed constraint in the presence of a YXN motif, such as a YAN, YDN or YEN motif. The YXN motif which may be located anywhere throughout the length of the peptide. For example, the YXN sequence may be located at or near the end of the length of the peptide such as for example, starting at the +1 or +2, +3 or +4 position or starting at the +15, +16, +17 or +18 position (relative to the first amino acid of a 20 amino acid peptide). Alternatively, the YXN motif may be internal and may start at the +5, +6, +7, +8, +9, +10, +11, +12, +13, or +14 position in a 20 amino acid peptide. It is to be understood that although the examples provided herein are for 20 amino acid long peptides, they equally apply to peptides of greater or lesser length whereby the YXN can be start at any location along the peptide.

In certain embodiments, the Grb7 peptide antagonist has a sequence of $X_m$-YXN-$X_n$, wherein m and n can each be 0 through to 17 inclusive provided that the sum of m and y is equal to or less than 17 (if the peptide is 20 amino acids in length), and wherein X is an amino acid, or an amino acid substitution, and is randomly selected independently from the selection of every other X residue in the peptide. In some important embodiments, the peptide has flanking cysteine residues and the corresponding sequence is C-$X_a$-YXN-$X_b$-C (SEQ ID NO:34; SEQ ID NO: 60 through to SEQ ID NO: 194, inclusive) wherein a and b can each can be 0 through to 15 inclusive provided that the sum of a and b is less than or equal to 15 (if the peptide is 20 amino acids in length). Exemplary sequences of Grb7 antagonists may further comprise an amino acid sequence selected from the group consisting of C-XXX-YAN-XXX-C (SEQ ID NO:23), C-XXX-YDN-XXX-C (SEQ ID NO:24), C-XXX-YEN-XXX-C (SEQ ID NO:25), C-XXXX-YAN-XXX-C (SEQ ID NO:26), C-XXXX-YDN-XXX-C (SEQ ID NO:27), C-XXXX-YEN-XXX-C (SEQ ID NO:28), C-XXX-YAN-XXXX-C (SEQ ID NO:29), C-XXX-YDN-XXXX-C (SEQ ID NO:30), and C-XXX-YEN-XXXX-C (SEQ ID NO:31). In still other embodiments, the peptide has the sequence $X_4$-C-$X_4$-YXN-$X_3$-C-$X_4$ (SEQ ID NO:33). In most instances, the tyrosine residue of the YXN motif will be non-phosphorylated.

Peptides which bind to Grb7 and thereby interfere with Grb7 binding to either a Grb7 ligand (e.g., a signaling factor) or, alternatively, a G7BP, can be generated and identified by conventional screening methods such as phage display procedures (e.g., methods described in Hart, et al., J. Biol. Chem. 269:12468 (1994)). Hart et al. report a filamentous phage display library for identifying novel peptide ligands for mammalian cell receptors. In general, phage display libraries using, e.g., M13 or fd phage, are prepared using conventional procedures such as those described in the foregoing reference. The libraries display inserts containing from 4 to 80 amino acid residues. The inserts optionally represent a completely degenerate or a biased array of peptides. Peptides that bind selectively to Grb7, and more preferably the SH2 domain of Grb7, are obtained by selecting those phages which express on their surface an amino acid sequence which recognizes and binds to Grb7 or the SH2 domain of Grb7. These phage then are subjected to several cycles of re-selection to identify the Grb7-binding phage that have the most useful binding characteristics. The minimal linear portion of the sequence that binds to Grb7 or the SH2 domain of Grb7 can be determined. Typically, phage that exhibit the best binding characteristics (e.g., highest affinity) are further characterized by nucleic acid molecule analysis to identify the particular amino acid sequences of the peptides expressed on the phage surface and the optimum length of the expressed peptide to achieve optimum binding. Phage can also be prescreened for their ability to bind to Grb2-SH2 domains or Grb14-SH2 domains or mutant Grb7-SH2 domains. Preferably, the peptides bind specifically to Grb7-SH2 domains and not to the other SH2 domains. Thus, prescreening of phage to Grb2-SH2 or Grb 14-SH2 domains or mutant Grb7 domains can enrich for phage of interest.

The displayed peptide sequence can vary in size. As the size increases, the complexity of the library increases. It is preferred that the total size of the displayed peptide sequence (the random amino acids plus any spacer amino acids) should not be greater than about 100 amino acids long, more preferably not greater than about 50 amino acids long, and even more preferably not greater than about 25 amino acids long, and most preferably less than or equal to 20 amino acids long. In some even more preferred embodiments, the peptide sequence is less than or equal to 12 amino acids in length.

Grb7 inhibitors can be identified using a set of screening assays. A first screen may involve selecting for binding partners of Grb7. Compounds such as library members can be screened for their ability to bind to Grb7 in vitro using standard binding assays well known to the ordinary artisan and are described below. For binding to Grb7, Grb7 may be presented in a number of ways including, but not limited to, cells expressing Grb7 (such as those described below), isolated Grb7, an isolated domain of Grb7 (e.g., an SH2 domain) or a fragment thereof, or a fusion protein of the SH2 domain and another protein such as an immunoglobulin or a GST fusion partner. Preferably, the Grb7 fragment is one capable of binding Grb7 ligands. For some high throughput screening assays, the use of purified forms of Grb7, its SH2 domain or a fusion of its SH2 domain with another protein may be preferable. Isolation of binding partners may be performed in solution or in solid state according to well-known methods.

Accordingly, the invention provides a method for screening a molecular library to identify a compound that inhibits interaction between Grb7 and a peptide comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:35, SEQ ID NO:39, SEQ ID NO:40, SEQ ID NO:41, SEQ ID NO:42, SEQ ID NO:43, SEQ ID NO:44, SEQ ID NO:47, SEQ ID NO:48, SEQ ID NO:49, SEQ ID NO:50, SEQ ID NO:51, SEQ ID NO:52 and SEQ ID NO:53, or functional equivalents thereof. The method generally involves performing a first assay between Grb7 and the peptide to obtain a first assay result; performing a second assay between Grb7 and the peptide in the presence of a molecular library member to obtain a second assay result; and comparing the first and second assay results to determine whether the molecular library member inhibits the interaction between Grb7 and the peptide. The assay may be a binding assay and it may be performed in vitro or in vivo. The assay may alternatively be a signaling assay. The method may involve the initial step of selecting a molecular library suspected of containing a Grb7 antagonist. Such a selection process may involve using libraries which are made with the preferred constraints mentioned herein. This general screening assay is amenable to screening a variety of libraries including peptide libraries such as synthetic peptide libraries, phage display libraries, peptidomimetic libraries, and combinatorial chemistry libraries. In order to increase the specificity of a library for Grb7, the library may be pre-screened by exposing it to a cell population which does not express Grb7 (e.g., a Grb2 or Grb14 containing preparation or a preparation of mutant Grb7-SH2 domains). In this way, binding partners which are not specific for Grb7 can be eliminated or at least reduced in number from the library prior to further screening. Procedures for pre-screening include but are not limited to affinity column purification or biopanning.

Standard binding assays are well known in the art, and a number of these are suitable in the present invention including ELISA, competition binding assay (particularly suitable in the present invention since either a native substrate of Grb7 such as ErbB2 or one of the G7BPs may be used), sandwich assays, radioreceptor assays using radioactively labeled G7BPs (wherein the binding is blocked in the presence of the antagonist), labeled in vitro protein-protein binding assays, electrophoretic mobility shift assays, immunoassays, cell-based assays such as two- or three-hybrid screens, etc. The nature of the assay is not essential provided it is sufficiently sensitive to detect binding of a small number of library members, although this sensitivity may not be as necessary for phage display based binding assays.

A variety of other reagents also can be included in the binding mixture. These include reagents such as salts, buffers, neutral proteins (e.g., albumin), detergents, etc. which may be used to facilitate optimal protein-protein and preferably protein-peptide binding. Such a reagent may also reduce non-specific or background interactions of the reaction components. Other reagents that improve the efficiency of the assay may also be used. The mixture of the foregoing assay materials is incubated under conditions under which the Grb7 normally specifically binds one or more of its ligands (e.g., ErbB2). The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours. After incubation, the presence or absence of specific binding between Grb7 and its ligand (e.g., ErbB2 or a G7BP) is detected by any convenient method available to the user.

Typically, a plurality of assay mixtures are run in parallel with different agent concentrations to obtain a different response to the various concentrations. One of these concentrations serves as a negative control, i.e., at zero concentration of agent or at a concentration of agent below the limits of assay detection.

For cell-free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., columns or gels of polyacrylamide, agarose or sepharose, microtiter plates, microbeads, resin particles, etc. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

For cell-free binding assays, one of the components usually comprises, or is coupled to, a detectable label. A detectable label is a moiety, the presence of which can be ascertained directly or indirectly. Generally, detection of the label involves an emission of energy by the label. The label can be detected directly by its ability to emit and/or absorb light of a particular wavelength (e.g., radioactivity, luminescence, optical or electron density, etc.). A label can be detected indirectly by its ability to bind, recruit and, in some cases, cleave another moiety which itself may emit or absorb light of a particular wavelength (e.g., epitope tag such as the FLAG epitope, enzyme tag such as horseradish peroxidase, etc.). An example of indirect detection is the use of a first enzyme label which cleaves a substrate into visible products. The label may be of a chemical, peptide or nucleic acid molecule nature although it is not so limited. Other detectable labels include radioactive isotopes such as $P^{32}$ or $H^3$, luminescent markers such as fluorochromes, optical or electron density markers, etc., or epitope tags such as the FLAG epitope or the HA epitope, biotin, avidin, and enzyme tags such as horseradish peroxidase, β-galactosidase, etc. The label may be bound to a library member, or incorporated into the structure of the library member. Grb7 (or an SH2 domain of Grb7), the Grb7 ligand (e.g., ErbB2 or a G7BP), or the candidate antagonist may be labeled by a variety of means for use in screening. There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the binding partners used in the screening assays, or will be able to ascertain such, using routine experimentation. Furthermore, the coupling of these labels the binding partners used in the screening assays of the invention can be done using standard techniques common to those of ordinary skill in the art.

Another labeling technique which may result in greater sensitivity consists of coupling the binding partners to low molecular weight haptens. These haptens can then be specifically altered by means of a second reaction. For example, it is common to use haptens such as biotin, which reacts with avidin, or dinitrophenol, pyridoxal, or fluorescein, which can react with specific anti-hapten antibodies.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, streptavidin-biotin conjugates, etc. Methods for detecting the labels are well known in the art.

One example of a suitable binding assay involves the use of Grb7, an SH2 domain of Grb7 or a Grb7 fusion protein immobilized on resin beads contained within a column or as a slurry in test tubes. This can be achieved by using a glutathione-S-transferase (GST) fusion of Grb7 or its SH2 domain and a column containing anti-GST antibody. The Grb7-GST fusion polypeptide is first immobilized on the column or resin, followed by the addition of a suspension of candidate antagonists such as, for example, library members, in a solution compatible with the binding of select antagonists to the SH2 domain of Grb7. The column is then washed to remove any residual non-bound compounds. The bound compounds are then eluted by changing the conditions on the column such that binding to the ligand binding site is no longer favored, such as pH or ionic concentration change, or competitive elution with reduced glutathione. The eluate is collected and the compounds contained therein are further analyzed. In the case where the compounds are peptides, the eluted peptides can be sequenced using standard Edman degradation amino acid sequencing techniques or in the case of non-peptide moieties, the eluted compounds are analyzed by standard analytical techniques such as HPLC and mass spectroscopy. Apparati for performing Edman degradation sequencing, an example of which is the Applied Biosystems 477A Protein Sequencer, are available commercially. Analysis of lead candidates from such binding assays using NMR spectroscopy are described in U.S. Pat. No. 5,877,030, the contents of which are incorporated herein by reference. In this way, the sequence or composition of the compounds which bind to the column can be deduced. This method allows one to determine the preferred binding partners of Grb7 or its SH2 domain.

Other assays for determining binding of a putative antagonist to Grb7 or the SH2 domain of Grb7 include labeled in vitro protein-protein binding assays, electrophoretic mobility shift assays, immunoassays, cell-based assays such as two- or three-hybrid screens, expression assays, etc. For example, two-hybrid screens are used to rapidly examine the effect of transfected nucleic acid molecules on the intracellular binding of G7BP or G7BP fragments (e.g., SH2 domains) to putative antagonists. The transfected nucleic acid molecules can derive from, for example, combinatorial peptide libraries or cDNA libraries. Convenient reagents for such assays, e.g., GAL4 fusion proteins, are known in the art.

As stated above, a second criteria which putative Grb7 antagonists must meet is the ability to compete with native Grb7 ligands (e.g., signaling factors such as tyrosine kinases, phosphatases, and adaptor proteins) for binding to Grb7. Thus, a second useful screen in the identification of Grb7 antagonists is the ability of the library member to bind to Grb7 in the presence of, for example, a tyrosine kinase such as ErbB2, and its ability, at a reasonable physiological concentration, to preclude erbB2 from binding to Grb7. An example of a similar assay designed to test Grb2 antagonists is reported by Yao et al. in which the Grb ligand is immobilized on a surface and a labeled Grb SH2 domain is applied to the surface in the presence or absence of the putative inhibitory peptide or agent. (Yao, et al., J. Med. Chem., 42:25-35, 1999) In this latter assay, the inhibitory efficacy of the peptide or agent can be determined, quantitated, and compared with other peptides by measuring the amount of label attached to the solid support (over background) in the presence of the peptide relative to in the absence of the peptide. Peptides or agents that inhibit or interfere with binding of Grb7 to its ligand will result in lower levels of label bound in their presence while those peptides which do not interfere with binding will generally not have an effect on the amount of label bound.

In a variation of these afore-mentioned binding assays, the candidate antagonist may be tested for the ability to disrupt a pre-formed complex of Grb7 and its ligand (e.g., a Grb7-ErbB2 complex). Disruption of the complex is intended to embrace not only the physical separation of Grb7 and one or more of its ligands, but also a disruption of the activity of the complex (i.e., the transmittal of a signal from, for example, a tyrosine kinase to another Grb7 ligand via Grb7). In this latter assay, Grb7 and its ligand are allowed to associate with each other to form a stable complex prior to the addition of the candidate antagonist. One member of the binding pair may be attached to a solid support while the other may be free. Preferably, the free binding member is also conjugated to a detectable label which allows its location to be determined. As an example, Grb7 (or the SH2 domain of Grb7) is attached to a solid surface and then exposed to ErbB2 (preferably in a phosphorylated form) which in turn may be conjugated to a fluorescent label. Maximum fluorescence is measured in the absence of the candidate antagonist. Fluorescence measurements are taken again following the addition of the candidate antagonist. Fluorescence measurements are taken again following the addition of the candidate antagonist. A decrease in the fluorescence following addition of the compound is indicative of an antagonist. Other assays for measuring disruption of Grb7 containing complexes are described in U.S. Pat. No. 6,001,583 and 6,037,134.

As used herein, signaling factors are proteins or polypeptides that are involved in transducing a signal into or within a cell. Grb7 ligands include endogenous signaling factors which interact with Grb7 to transmit a signal to Grb7 or to accept a signal from Grb7. As used herein, an "endogenous" molecule is one that is known to naturally exist in a cell and includes intracellular and transmembrane molecules.

Examples of endogenous Grb7 ligands include tyrosine kinases, phosphatases, and adaptor proteins. Tyrosine kinases include receptor tyrosine kinases and non-receptor tyrosine kinases. Receptor tyrosine kinases include, but are not limited to, EGRF, PDGFR, CSF-1R (c-fms), c-kit, LET-23R, HGFR/SFR (c-met), FGFR, HER2/neu, HER4, IGF1R, flt3/flk2, flk1, ErbB, c-ret, EphA2, TrkB (BDNFR), tek/tie2, stk, flt-1 (VEGFR), RON, TrkA (NGFR), MuSK, VEGFR2, ROR, tie1, etc. Non-receptor tyrosine kinases include, but are not limited to, Fyn, Lck, Lyn, Syk/ZAP-70, Src, Yes, Hck, Blk, Yrk, Fgr, Rak, Brk, and Csk. Still other molecules lack tyrosine kinase activity but are still capable of being phosphorylated by a tyrosine kinase (e.g., ErbB2). Molecules can be phosphorylated by virtue of the fact they contain a tyrosine, a serine or a threonine residue which can be phosphorylated. Depending upon the embodiment of the invention, these molecules may or may not be phosphorylated. Receptor tyrosine kinases may be ligand-activated or not activated. In some preferred embodiments, the Grb7 ligands are tyrosine kinases selected from the group consisting of HER2/ErbB2, PDGFR, epidermal growth factor (EGFR), cKit/Stem cell receptor, FAK, Ret proto-oncogene, RndI, a member of the Rho family, and the insulin receptor; phosphatases such as Syp/SHPTP2; and adaptor proteins such as Shc and Grb10. In another embodiment, the Grb7 ligand is ErbB3. In yet other embodiments, the Grb7 ligand is an Fc epsilon receptor. In the screening assays described herein, the Grb7 ligand may be a G7BP, or it may be an antibody or an antibody fragment specific for Grb7 such as #188 disclosed by Margolis in U.S. Pat. No. 6,037,134. Two other Grb7 specific antibodies are commercially available from Santa Cruz Biotech (#sc606 rabbit polyclonal of the carboxy-terminal end, and #sc-607 rabbit polyclonal of the N-terminus) which are reactive with mouse, rat, and human Grb7.

Binding interactions between Grb7 and its endogenous ligands can also be carried out through the use of cell-based assays. As example of this is immunoprecipitation of Grb7 ligands from cell lysates using purified Grb7 or purified Grb7 SH2 domains in the presence and absence of putative antagonists. This latter approach has been used previously to identify Grb2 inhibitory peptides.

In some embodiments, the screening assays of the invention can also be used to identify antibodies and fragments of antibodies (e.g., Fab, F(ab)$_2$, Fd and antibody fragments which include a CDR3 region which binds selectively to a Grb7 polypeptide, preferably at the SH2 domain of Grb7) and which are Grb7 antagonists. Preferably, the antibodies for human therapeutic applications are human or humanized antibodies.

As is well-known in the art, only a small portion of an antibody molecule, the paratope, is involved in the binding of the antibody to its epitope (see, in general, Clark, W. R. (1986) *The Experimental Foundations of Modem Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/043 81 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Binding partner screens can then be followed by screens for biological antagonist activity. To be useful, the Grb7 antagonist binds to Grb7, precludes or inhibits binding of Grb7 to one or more of its endogenous ligands and, in doing so, prevents, inhibits or interferes with signal transduction from the Grb7 ligand and events downstream of such signaling. An example of an event downstream of signaling may be cell proliferation. One way of measuring cell proliferation involves the use of in vitro clonogenic assays. Such assays can be performed using either cell lines known to express a functional Grb7 or other cells which have been manipulated (i.e., transfected) to express Grb7. The number and quality of colonies can be determined as a function of the presence and absence of the library member. Preferably, the assays are carried out by culturing the cells in a semi-solid culture under conditions which stimulate maximal colony growth from the cell population. The library member is then titrated into the cultures in order to determine the amount necessary to reduce colony formation. In this manner, in addition to the amount of antagonist necessary to inhibit colony growth altogether, one can also determine that amount which inhibits the growth by a particular percentage. In this way, the amount of antagonist which impacts upon colony growth from, for example, aggressive Grb7-expressing cell lines, but not on the growth of less aggressive non-Grb7-expressing cell lines can be determined. For example, it may be desirable to reduce colony growth of Grb7-expressing cell lines by the maximum amount possible while leaving colony growth by non-Grb7-expressing cell lines unaffected. Clonogenic assays such as those described herein are routinely employed by artisans of ordinary skill. (DeFriend et al., 1994, Br. J. Cancer, 70(2):204-11; Glinsky et al., 1996, Clin. Exp. Metastasis, 14(3):253-67; Shen et al., 1998, Oncol. Res. 10(6):325-31; Perez et al., 1998, Cancer Chemother. Pharmacol. 41(6):448-52) Moreover, each of the afore-mentioned in vitro screening assays is amenable to high-throughput screening.

Cells useful in these in vitro clonogenic assays are cell lines or primary cells which preferably are known to express Grb7 and one or more of its endogenous ligands. Examples include breast cancer cell lines such as SKBR-3, HER1-2 and BT474. Cells which are genetically manipulated to overexpress Grb7 are also useful in the invention. Cell lines which can be so manipulated are preferably breast cancer cell lines, but are not so limited, and include MDA-MB-435, MDA-MB-453, MDA-MB-468, MDA-MB-231, and HEK-293. A control breast cell line which can be used is MCF-12A. The Examples provided herein demonstrate cell lines that are useful for the assay of G7BP inhibitory function.

Another way of measuring the biological antagonist activity of the synthetic compound is to perform in vivo assays in which the putative antagonist is introduced into animals, preferably mice, which have been made susceptible to, for example, breast cancer tumors. The mice are then analyzed to determine whether the putative antagonist ameliorates the symptoms of, for example, the cancer (e.g., a reduction in tumor growth). In some instances, breast tissue may also be harvested and plated into a clonogenic assay. Preferably the size of tumors in vivo and/or the number and quality of colonies derived from test animals should be compared to that of animals injected with control carrier (i.e., saline) lacking the putative antagonist. Adverse side effects can also be tested in animals injected with putative antagonists in this manner. Examples of such in vivo mouse models of breast cancer have been described by Gabri et al., 1999 Pathobiology 67(4):180-5; Liu et al., 1999 Am. J. Pathol. 155(6): 1861-7; and Vodovozona et al., 2000 Eur. J. Cancer 36(7): 942-9.

The antagonists generated as described herein can also be screened in vivo or in vitro for the ability to prevent metastasis, using two different animal models of cancer, B 16BL6 and LLC. Divino et al., 2000 Breast Cancer Res. Treat. 650(2): 129-34 specifically describes a mouse model of breast cancer metastasis. In some embodiments of the invention, the antagonists can be screened according to their ability to prevent invasion of tumor cells across a barrier. The barrier for the tumor cells may be an artificial barrier in vitro or a natural barrier in vivo. An in vivo barrier refers to a cellular barrier present in the body of a subject. In vitro barriers include but are not limited to extracellular matrix coated membranes, such as Matrigel. Thus the putative antagonists can be tested for their ability to inhibit tumor cell invasion in a Matrigel invasion assay system as described in detail by Parish, C. R., et al., "A Basement-Membrane Permeability Assay which Correlates with the Metastatic Potential of Tumour Cells," Int. J. Cancer (1992) 52:378-383, provided the cells used in the assay have been characterized as having abnormal interaction of Grb7 and its ligands. Matrigel is a reconstituted basement membrane containing type IV collagen, laminin, heparan sulfate proteoglycans such as perlecan, which bind to and localize bFGF, vitronectin as well as transforming growth factor-β (TGF-β), urokinase-type plasminogen activator (uPA), tissue plasminogen activator (tPA), and the serpin known as plasminogen activator inhibitor type 1 (PAI-1). Other in vitro and in vivo assays for metastasis have been described in the prior art, see, e.g., U.S. Pat. No. 5,935,850, issued on Aug. 10, 1999, which is incorporated by reference.

The invention also embraces the use of nucleic acid molecules that code for Grb7 peptide antagonists such as the G7BPs of the invention. Due to the degeneracy of the genetic code, a number of nucleic acid molecules code for each G7BP of the invention. For example, while the nucleic acid molecule having the sequence CGU GUU CAA GAA UGU AAA UAU UUA UAU UAU GAU AAU GAU AUA UUA UGU AAA GAU GAU GGU (SEQ ID NO:11) encodes G7BP-1, there are multiple other nucleic acid molecules which also encode G7BP-1. For example, the arginine residue in the first position of G7BP-1 is coded by the following six codons: CGU, CGC, CGA, CGG, AGA, and AGG. Each of the six codons is equivalent for the purposes of encoding an arginine residue. Thus, it will be apparent to one of ordinary skill in the art that any of the arginine-encoding nucleotide triplets may be employed to direct the peptide synthesis apparatus, in vitro or in vivo, to incorporate an arginine residue into a G7BP. Thus, although SEQ ID NO:11 uses only the first of these codons, it is to be understood that the invention embraces nucleic acid molecules which use any of the six codons to code for arginine. Similarly, the invention embraces nucleic acid molecules that use any of the four codons coding for valine (GUU, GUC, GUA, and GUG), or either of the two codons coding for glutamine (CAA, CAG), or either of the two codons coding for glutamic acid (GAA, GAG), or either of the two codons coding for cysteine (UGU, UGC), or either of the two codons coding for lysine (AAA, AAG), or either of the two codons coding for tyrosine (UAU, UAC), or any of the six codons coding for leucine (UUA, UUG, CUU, CUC, CUA, and CUG), or either of the two codons coding for aspartic acid (GAU, GAC), or either of the two codons coding for asparagine (AAU, AAC), or any of the four codons coding for glycine (GGU, GGC, GGA, and GGG), or either of the two codons coding for phenylalanine (UUU, UUC), or either of the two codons coding for histidine (CAU, CAC), or any of the four codons coding for proline (CCU, CCC, CCA, CCG), or any of the four codons coding for threonine (ACU, ACC, ACA, and ACG), or any of the six codons coding for serine (UCU, UCC, UCA, UCG, AGU, and AGC), or any of the four codons coding for alanine (GCA, GCU, GCC, and GCG), or any of the three codons coding for isoleucine (AUU, AUC, and AUA). Methionine and tryptophan are each coded by a single codon respectively.

Thus an exemplary nucleic acid molecule that encodes G7BP-2 is AAA UUA UUU UGG UGU ACU UAU GAA GAU UAU GCA AAU GAA UGG CCU UGU CCU GGU UAU UCU (SEQ ID NO:12), an exemplary nucleic acid molecule that encodes G7BP-3 is AAU GUU UCU GAA UGU AUU UAU AUU CAU UAU GAU AAU UGG UCU UUA UGU GGU GUU GAA GUU (SEQ ID NO:13), an exemplary nucleic acid molecule that encodes G7BP-4 is GGU GUU UCU AAU UGU GUU UUU UGG GGU UAU GCA AAU GAU UGG UUA UGU UCU GAU UAU UCU (SEQ ID NO:14), an exemplary nucleic acid molecule that encodes G7BP-5 is CGU UCU ACU UUA UGU UGG UUU GAA GGU UAU GAU AAU ACU UUU CCU UGU AAA UAU UUU CGU (SEQ ID NO:15), an exemplary nucleic acid molecule that encodes G7BP-6 is UUU UGU GCA GUU UGU AAU GAA GAA UUA UAU GAA AAU UGU GGU GGU UGU UCU GUU GGU AAA (SEQ ID NO:16), and an exemplary nucleic acid molecule that encodes G7BP-7 is CGU ACU UCU CCU UGU GGU AUA AUU GGU UAU GAU AAU AUU UUU GAA UGU ACU UAU UUA GGU (SEQ ID NO:17).

It is to be understood that although the codons and nucleotide sequences listed herein contain uracil bases, codons and nucleic acid molecules in which uracil is replaced with thymidine are equally embraced by the invention. Accordingly, the nucleic acid sequences listed above can be in an RNA form (as stated in the Sequence Listing) or in a DNA form. Similarly, modified nucleotides may also be used in any of the nucleic acid molecules of the invention provided their function is preserved (e.g., hybridization, ability to be cloned or transcribed, etc.). Examples of modified nucleotides include those with a modified base and/or sugar, those having backbone sugars which are covalently attached to low molecular weight organic groups other than a hydroxyl group at the 3' position and other than a phosphate group at the 5' position (e.g., a 2'-O-alkylated ribose group). In addition, modified nucleic acids may include sugars such as arabinose instead of ribose. The nucleic acids may be heterogeneous in backbone composition thereby containing any possible combination of polymer units linked together such as peptide-nucleic acids (which have an amino acid backbone with nucleic acid bases). In some embodiments, the nucleic acids are homogeneous in backbone composition. The purines and pyrimidines of the nucleic acids may also be substituted e.g., base analogs such as C-5 propyne substituted bases (Wagner et al., *Nature Biotechnology* 14:840-844, 1996). Purines and pyrimidines which can be incorporated into the nucleic acids of the invention include but are not limited to adenine, cytosine, guanine, thymine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties.

As used herein with respect to nucleic acid molecules, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid molecule is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated, but a nucleic acid molecule sequence existing in its native state in its natural host is not. An isolated nucleic acid molecule may be substantially purified, but need not be. For example, a nucleic acid molecule that is isolated within a cloning or expression vector is not pure in that it may comprise only a tiny percentage of the material in the cell in which it resides. Such a nucleic acid molecule is isolated, however, as the term is used herein because it is readily manipulable by standard techniques known to those of ordinary skill in the art.

According to the invention, isolated G7BP nucleic acid molecules include: (a) nucleic acid molecules which code for amino acid sequences such as SEQ ID NO:1, SEQ ID NO:2, SEQ ID NO:3, SEQ ID NO:4, SEQ ID NO:5, SEQ ID NO:6, SEQ ID NO:7, SEQ ID NO:35, SEQ ID NO:39, SEQ ID NO:40, SEQ ID NO:41, SEQ ID NO:42, SEQ ID NO:43, or SEQ ID NO:44, SEQ ID NO:47, SEQ ID NO:48, SEQ ID NO:49, SEQ ID NO:50, SEQ ID NO:51, SEQ ID NO:52, SEQ ID NO:53, or functionally equivalent fragments thereof (b) deletions, additions and substitutions of (a) which code for a Grb7 antagonist, (c) nucleic acid molecules that differ from the nucleic acid molecules of (a) or (b) in codon sequence due to the degeneracy of the genetic code (as described above), and (d) complements of (a), (b) or (c). Examples of G7BP nucleic acid molecules include nucleic acid molecules having the nucleotide sequence selected from the group consisting of SEQ ID NO:11, SEQ ID NO:12, SEQ ID NO:13, SEQ ID NO:14, SEQ ID NO:15, SEQ ID NO:16, and SEQ ID NO:17, and degenerates thereof.

Homologs and alleles of the G7BP nucleic acid molecules of the invention may include endogenous Grb7 inhibitory ligands. These molecules can be identified by conventional techniques. An example of this aspect of the invention is those endogenous nucleic acid molecules which code for a peptide comprising the amino acid sequence of any of the G7BPs disclosed herein and which hybridize under stringent conditions to a nucleic acid molecule having a nucleotide sequence selected from the group consisting of SEQ ID NO:11, SEQ ID NO:12, SEQ ID NO:13, SEQ ID NO:14, SEQ ID NO:15, SEQ ID NO:16, and SEQ ID NO:17. The term "stringent conditions" as used herein refers to parameters with which the art is familiar. Nucleic acid molecule hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH 7), 0.5% SDS, 2 mM EDTA). SSC is 0.15M sodium chloride/0.15M sodium citrate, pH 7; SDS is sodium dodecyl sulphate; and EDTA is ethylenediaminetetracetic acid. After hybridization, the membrane upon which the DNA is transferred is washed at 2×SSC at room temperature and then at 0.1×SSC/0.1% SDS at temperatures up to 68° C.

There are other conditions, reagents, and so forth which can be used, and would result in a similar degree of stringency. The skilled artisan will be familiar with such conditions, and thus they are not given here. It will be understood, however, that the skilled artisan will be able to manipulate the conditions in a manner to permit the clear identification of homologs and alleles of G7BP nucleic acid molecules of the invention. The skilled artisan also is familiar with the methodology for screening phage, cells and libraries preferably peptide or aptamer libraries for expression of Grb7 antagonists which then are isolated, followed by isolation of the pertinent nucleic acid molecule and sequencing.

In general homologs and alleles typically will share at least 75% nucleotide identity to any G7BP nucleic acid molecules and/or at least 90% amino acid identity to any G7BP (e.g., SEQ ID NO:1 through to SEQ ID NO:7 inclusive). Preferably, homologs and alleles will share at least 85% nucleotide identity and/or at least 95% amino acid identity and, even more preferably, at least 95% nucleotide identity and/or at least 99% amino acid identity will be shared. The homology can be calculated using various, publicly available software tools developed by NCBI (Bethesda, Md.) that can be obtained through the internet at the NIH website. Exemplary tools include the BLAST system using default settings, available at the NCBI website on the internet. Pairwise and ClustalW alignments (BLOSUM30 and/or BLOSUM62 matrix settings) as well as Kyte-Doolittle hydropathic analysis can be obtained using the MacVetor sequence analysis software (Oxford Molecular Group). Watson-Crick complements of the foregoing nucleic acid molecules also are embraced by the invention.

The invention also provides isolated unique fragments of G7BP nucleic acid molecules or complements thereof. A unique fragment is one that is a 'signature' for the larger nucleic acid molecule such as, for example, those encoding G7BPs or endogenous Grb7 inhibitory ligands. For example, the unique fragment is long enough to assure that its precise sequence is found sparingly in molecules within the human genome. Those of ordinary skill in the art may apply no more than routine procedures to determine if a fragment is unique within the human genome. Unique fragments, however, exclude fragments completely composed of the nucleotide sequences of any of GenBank accession numbers listed in Table 2 (see below) or other previously published sequences as of the filing date of this application.

A fragment which is completely composed of the sequence described in the foregoing GenBank deposits is one which does not include any of the nucleotides unique to the sequences of the invention. Thus, a unique fragment must contain a nucleotide sequence other than the exact sequence of those in GenBank or fragments thereof. The difference may be an addition, deletion or substitution with respect to all or part of the GenBank sequence or it may be a sequence wholly separate from the GenBank sequence.

Unique fragments can be used as probes in Southern and Northern blot assays to identify nucleic acid molecules which contain these nucleotide sequences, or can be used in amplification assays such as those employing PCR. Unique fragments also can be used to produce fusion proteins for generating antibodies or determining binding of the peptide fragments or for generating immunoassay components.

As will be recognized by those skilled in the art, the size of the unique fragment will depend upon its conservancy in the genetic code. Thus, some regions of G7BP nucleic acid molecules (e.g., SEQ ID NO:11 through to SEQ ID NO:17, inclusive (as well as degenerates thereof)), or complements thereof will require longer segments to be unique while others will require only short segments, typically between 12 and 32 nucleotides long (e.g. 12, 13, 14, 15, 16, 17, 18, 19, 20, 21, 22, 23, 24, 25, 26, 27, 28, 29, 30, 31, and 32 bases) or more, up to the entire length of the disclosed sequence. As mentioned above, this disclosure intends to embrace each and every fragment of each sequence listed, beginning at the first nucleotide, the second nucleotide and so on, up to 8 nucleotides short of the end, and ending anywhere from nucleotide number 8, 9, 10, and so on for each sequence listed, up to the very last nucleotide, provided the sequence is unique as described above. Taking into account the exclusion described above, virtually any segment of the region of, for example, SEQ ID NO:11, SEQ ID NO:12, SEQ ID NO:13, SEQ ID NO:14, SEQ ID NO:15, SEQ ID NO:16, or SEQ ID NO:17 beginning at nucleotide 1 and ending at nucleotide 60, or complements thereof, that is 20 or more nucleotides in length will be unique. Those skilled in the art are well versed in methods for selecting such sequences, typically on the basis of the ability of the unique fragment to selectively distinguish the sequence of interest from other sequences in the human genome of the fragment to those on known databases typically is all that is necessary, although in vitro confirmatory hybridization and sequencing analysis may be performed.

Most if not all of the characteristics of nucleic acid molecule unique fragments are shared with peptide unique fragments disclosed herein.

The invention also involves expression vectors coding for G7BPs and fragments and variants thereof and host cells containing those expression vectors. Virtually any cells, prokaryotic or eukaryotic, which can be transformed with heterologous DNA or RNA, and which can be grown or maintained in culture, may be used in the practice of the invention. Examples include bacterial cells such as *E. coli* and mammalian cells such as mouse, hamster, pig, goat, primate, etc. They may be of a wide variety of tissue types, including mast cells, fibroblasts, oocytes, and lymphocytes, and they may be primary cells or cell lines. Specific examples include CHO cells and COS cells. Cell-free transcription systems also may be used in lieu of cells.

As used herein, a "vector" may be any of a number of nucleic acid molecules into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. In some preferred embodiments, the expression system is a phage. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a marker or coding sequence and regulatory sequences are said to be "operably" joined when they are covalently linked in such a way as to place the expression or transcription of the coding sequence under the influence or control of the regulatory sequences. If it is desired that the coding sequences be translated into a functional peptide or polypeptide, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CCAAT sequence, and the like. Especially, such 5' non-transcribed regulatory sequences will include a promoter region which includes a promoter sequence for transcriptional control of the operably joined coding sequence. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered for G7BP expression by the introduction of a heterologous nucleic acid molecule, usually DNA, encoding a G7BP or fragment or a variant thereof into the cells. The heterologous nucleic acid molecules are placed under operable control of transcriptional elements to permit the expression of the heterologous nucleic acid molecules in the host cell.

Preferred systems for mRNA expression in mammalian cells are those such as pcDNA3.1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally suitable for expression in primate or canine cell lines is the pCEP4 vector (Invitrogen, Carlsbad, Calif.), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (Nuc. Acids Res. 18:5322, 1990), and its use in transfection experiments is disclosed by, for example, Demoulin (Mol. Cell. Biol. 16:4710-4716, 1996). Still another preferred expression vector is an adenovirus, described by Stratford-Perricaudet, which is defective for E1 and E3 proteins (J. Clin. Invest. 90:626-630, 1992). The use of the adenovirus as an Adeno.P1A recombinant is disclosed by Warnier et al., in intradermal injection in mice for immunization against P1A (Int. J. Cancer, 67:303-310, 1996).

The invention also embraces so-called expression kits, which allow the artisan to prepare a desired expression vector or vectors. Such expression kits include at least one or more of the previously discussed coding sequences or fragments thereof. Other components may be added, as desired, as long as the previously mentioned sequences, which are required, are included.

It will also be recognized that the invention embraces the use of the above described G7BP nucleotide sequence-containing expression vectors to transfect host cells and cell lines, be these prokaryotic (e.g., *E. coli*), or eukaryotic (e.g., CHO cells, COS cells, yeast expression systems, and recombinant baculovirus expression in insect cells). Especially useful are mammalian cells such as human, mouse, hamster, pig, goat, primate, etc., from a wide variety of tissue types including primary cells and established cell lines. Specific examples include mammalian epithelial cells, fibroblast cells, and kidney epithelial cells, either as primary cells or cell lines.

As eluded to earlier, the Grb7 antagonists of the invention, including G7BP-1 through to G7BP-7, SEQ ID NO:34; SEQ ID NO: 60 through to SEQ ID NO: 194, inclusive, SEQ ID NO:39, SEQ ID NO:40, SEQ ID NO:41, SEQ ID NO:42, SEQ ID NO:43, and SEQ ID NO:44, and preferably the nucleic acid molecules that encode theses peptides, can be used to screen cells or peptide or nucleic acid libraries for naturally occurring Grb7 antagonists with homology to the G7BPs. Naturally occurring Grb7 antagonists may comprise or share homology with the amino acid sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:35, SEQ ID NO:39, SEQ ID NO:40, SEQ ID NO:41, SEQ ID NO:42, SEQ ID NO:43, SEQ ID NO:44, SEQ ID NO:47, SEQ ID NO:48, SEQ ID NO:49, SEQ ID NO:50, SEQ ID NO:51, SEQ ID NO:52, or SEQ ID NO:53, or functionally equivalent fragments thereof. Alternatively, the nucleic acid molecules which code for naturally occurring Grb7 antagonists may have homology to the nucleic acid molecules which encode G7BPs. Naturally occurring nucleic acid molecules with such homology may be identified through stringent hybridization of the G7BP nucleic acid molecules to cells (e.g., whole cell filter hybridization) or nucleic acid libraries (e.g., cDNA libraries). Naturally occurring peptides or polypeptides with such homology may be identified through binding to antibodies specific for G7BP. In this way, native, naturally occurring binding partners of Grb7 may be identified. Polypeptides identified in the manner may be useful, for example, as Grb7 antagonists as well as in elucidating the natural mechanism through which Grb7 and its interactions are inhibited. Polypeptides which are identified in this manner can be isolated from biological samples including tissue or cell homogenates, or alternatively can also be expressed recombinantly in a variety of prokaryotic and eukaryotic expression systems by constructing an expression vector appropriate to the expression system, introducing the expression vector into the expression system, and isolating the recombinantly expressed protein.

The peptides, and unique fragments thereof, may be used in the diagnostic or therapeutic methods of the invention either in a free form (i.e., unconjugated or not complexed with another compound), or alternatively they may be used in a conjugated form.

Thus, the invention embraces conjugates of Grb7 antagonists such as G7BP-1 through to G7BP-7, and G7BP-1NA through to G7BP-7NA, and compounds such as detectable labels and cytotoxic agents.

Conjugation of the Grb7 antagonist to a detectable label facilitates, among other things, the use of such agents in diagnostic assays. Another category of detectable labels includes diagnostic and imaging labels such as for magnetic resonance imaging (MRI): Gd(DOTA); for nuclear medicine: $^{201}$Tl, gamma-emitting radionuclide 99 mTc; for positron-emission tomography (PET): positron-emitting isotopes, (18)F-fluorodeoxyglucose ((18)FDG), (18)F-fluoride, copper-64, gadodiamide, and radioisotopes of Pb(II) such as 203Pb; 111In.

Cytotoxic agents that can be conjugated to the peptides in order to induce death of the tissue or tumor include, but are not limited to, taxanes (paclitaxel and docetaxel), vinorelbine, gemcitabine, and capecitabine (for breast cancer), small molecule quinazoline and pyrimidine-based inhibitors, radioisotopes such as 212Pb, anti-cancer agents such as doxorubicin, and including other anti-cancer agents and chemotherapeutics listed herein, toxins such as pokeweed anti-viral protein, cholera toxin, pertussis toxin, ricin, gelonin, abrin, diphtheria exotoxin, or Pseudomonas exotoxin. Toxin moieties can also be high energy-emitting radionuclides such as cobalt-60.

Other agents which can be conjugated to the peptides of the invention include immunomodulatory agents, anti-angiogenic agents, and translocation agents. An immunomodulatory agent is an agent which is capable of modulating an immune response, preferably at the tissue having the disorder. An anti-angiogenic agent is an agent which can inhibit angiogenesis, including inhibiting new blood vessel budding or growth of pre-existing vessels. Such agents are useful in restricting the blood supply to a diseased tissue or tumor. Anti-angiogenic agents include sulfated beta-cyclodextrins, sulfated malto-oligosaccharides, suramin, angiostatin, endostatin, fumagillin, non-glucocorticoid steroids, and heparin or heparin fragments, and antibodies to one or more angiogenic peptides such as αFGF, βFGF, VEGF, IL-8, and GM-CSF. Translocation agents, as used herein, refer to compounds, preferably peptides, which enable the transport of the peptides of the invention (e.g., G7BP-1 through G7BP-7, functional equivalents and unique fragments thereof) from the extracellular compartment to the intracellular compartment. Usually these translocation agents permit entry of a G7BP, or its functional equivalent, into the cell cytoplasm, where Grb7 and its ligands exist and complex. Examples of translocation agents which are useful in the invention include, but are not limited to, membrane translocating sequence (SEQ ID NO:18), transportan sequence (SEQ ID NO:19), Antennapedia sequence (SEQ ID NO:20), cyclic integrin-binding peptide (SEQ ID NO:21), and Tat-mediated peptide (SEQ ID NO:22).

The conjugations or modifications described herein employ routine chemistry, which chemistry does not form a part of the invention and which chemistry is well known to those skilled in the art of chemistry. The use of protecting groups and known linkers such as mono- and hetero-bifunctional linkers are well documented in the literature and will not be repeated here.

As used herein, "conjugated" means two entities stably bound to one another by any physiochemical means. It is important that the nature of the attachment be of such a nature that it does not impair substantially the effectiveness of either entity. Keeping these parameters in mind, any linkage known to those of ordinary skill in the art may be employed, covalent or noncovalent. Covalent is preferred. Noncovalent methods of conjugation may also be used. Noncovalent conjugation includes hydrophobic interactions, ionic interactions, high affinity interactions such as biotin-avidin and biotin-streptavidin complexation and other affinity interactions. Such means and methods of attachment are well known to those of ordinary skill in the art.

The invention additionally provides methods which use the Grb7 antagonists disclosed herein. These methods include methods of diagnosis, including medical imaging, and methods of prevention and treatment of disorders characterized by abnormal interaction of Grb7 with its ligands. The invention seeks, in one aspect, to prophylactically or therapeutically treat subjects having or at risk of having a disorder characterized by abnormal or adverse interaction of Grb7 with a Grb7 ligand. The method involves administering to a subject in need of such treatment (i.e., a subject who has been diagnosed as having or at risk of having the disorder) a Grb7 antagonist that is capable of binding to Grb7, precluding the interaction of Grb7 with one or more of its ligands or disrupting a pre-existing Grb7-containing complex (i.e., a complex of Grb7 and one or more of its ligands) and inhibiting or interfering with signal transduction. The antagonist is administered in an amount effective to inhibit the disorder. In important embodiments, the Grb7 antagonist is a peptide comprising an XYN amino acid sequence preferably selected from the group consisting of YAN, YEN, and YDN, or a functional equivalent thereof. In preferred embodiments, the peptide is non-phosphorylated. In even more preferred embodiments, the antagonist is a peptide having an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:35, SEQ ID NO:39, SEQ ID NO:40, SEQ ID NO:41, SEQ ID NO:42, SEQ ID NO:43, SEQ ID NO:44, SEQ ID NO:47, SEQ ID NO:48, SEQ ID NO:49, SEQ ID NO:50, SEQ ID NO:51, SEQ ID NO:52, SEQ ID NO:53, or functional equivalents (including fragments) thereof. The peptides may be linear, but in some preferred embodiments, they are cyclic.

As used herein, a subject is a human, non-human primate, cow, horse, pig, sheep, goat, dog, cat or rodent. In all embodiments, human subjects are preferred.

The subject to be treated, according to the methods of the invention, may be at risk of developing a disorder characterized by abnormal interaction of Grb7 to a signaling factor such as a Grb7 ligand, or alternatively, the subject may have such a disorder. The term "characterized by abnormal interaction of Grb7 with a Grb7 ligand" refers to abnormal quality or quantity of interaction. Abnormal interaction may include but is not limited to increased interaction of Grb7 with one or more of its ligands, increased signal transduction through Grb7, or interaction of Grb7 with a signaling factor which Grb7 normally does not interact with. Increased interaction of Grb7 with one or more of its ligands may be a manifestation of an underlying phenomenon such as increased transcription and translation of Grb7, increased transcription and translation of one or more Grb7 ligands, or mutation of Grb7 and/or one or more of its ligands so as to produce a higher affinity complex than might exist in normal cells.

The disorder may also result from increased levels of Grb7 ligands, or increased accessibility of these ligands to Grb7, thereby saturating Grb7 binding sites and precluding interaction with other ligands. By inhibiting a subset of Grb7 interactions, the antagonists may return the cell to a normal level of Grb7 interactions. In this way, the invention also provides methods and compositions for identifying and using antagonists that selectively inhibit some Grb7 interactions but not all. This can be easily accomplished by screening putative antagonists for their ability to selectively disrupt some but not all Grb7 interactions. In certain embodiments, it may be preferred that the antagonist inhibit or disrupt all Grb7 interactions.

Abnormal levels of Grb7, Grb7 ligands or of Grb7 interaction are defined as levels higher than those observed in a control normal population itself as described herein. A "normal" level, as used herein in reference to the level of Grb7 mRNA or polypeptide, Grb7 ligand mRNA or polypeptide or Grb7 association with one or more of its ligands may be a level in a control population, which preferably includes subjects having similar characteristics as the treated individual, such as age and sex. The "normal" level can also be a range, for example, where a population is used to obtain a baseline range for a particular group into which the subject falls. Thus, the "normal" value can depend upon a particular population selected. Preferably, the normal levels are those of apparently healthy subjects who have no prior history of Grb7 or signaling molecule-mediated disorders. As an example, if the subject to be treated has been diagnosed as having breast cancer or is at risk of having breast cancer, then the control population is one that does not have breast cancer and is not at risk of having breast cancer (e.g., that does not have a family history of breast cancer).

More preferably, the normal level is that level in a tissue of a normal subject corresponding to the tissue sampled for the test subject. In other instances, the normal levels can also be determined by measuring transcription, translation and/or binding levels in a sample of normal tissue adjacent to the suspected diseased tissue in the subject to be treated. As an example, breast tumors are, in some cases, sufficiently delineated to the extent that such tissue can be distinguished from the surrounding normal breast tissue. This delineation facilitates selective removal of diseased breast tissue, such as occurs in non-radical mastectomies (e.g., lumpectomy). Similarly, such delineation can be used in the present invention to harvest both suspected diseased tissue and normal tissue from a given subject. Such normal levels can then be established as preselected values, taking into account the category in which an individual falls. Appropriate ranges and categories can be selected with no more than routine experimentation by those of ordinary skill in the art. Either the mean or another preselected number within the range can be established as the normal preselected value.

The disorders to be prevented or treated according to the invention may occur in tissues in which Grb7 is known to be expressed. Tissues in which Grb7 is predominantly expressed include liver, kidney, and gonads, including the testes, ovary, and uterus (in mouse), and pancreas, kidney, prostate, small intestine, and placenta (in humans). Tissues in which Grb7 is expressed at lower levels include (in humans) lung, liver, testis, and colon. However, disorders to be prevented or treated may also occur in tissues in which Grb7 expression has not been detected normally (e.g., heart, breast, brain, esophagus, skeletal muscle, spleen, thymus, and peripheral blood leukocytes). Tissues at risk of developing a disorder similarly include tissues in which Grb7 is normally expressed as well as tissues in which the disorders listed herein have been found previously (e.g., breast and esophageal tissue).

Preferably, the disorder being diagnosed or treated is a proliferative disorder such as cancer. As used herein, a cancer is defined as an uncontrolled (e.g., factor independent) growth of abnormal cells, which can either remain localized, or may disseminate throughout the body via the bloodstream or the lymphatic system, and thereby seed a secondary site (i.e., a metastasis). The diagnostic, prophylactic, and treatment methods of the invention are intended to be used to in the prevention and treatment of primary tumors and secondary tumors (i.e., metastases). Examples of cancers to be diagnosed, prevented, and/or treated include: biliary tract cancer; brain cancer, including glioblastomas and medulloblastomas; breast cancer; cervical cancer; choriocarcinoma; colon cancer; endometrial cancer; esophageal cancer; gastric cancer; hematological neoplasms, including acute lymphocytic and myelogenous leukemia; chronic lymphocytic and myelogenous leukemia; multiple myeloma; AIDS-associated leukemias and adult T-cell leukemia lymphoma; intraepithelial neoplasms, including Bowen's disease and Paget's disease; liver cancer; lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells, and mesenchymal cells; pancreas cancer; prostate cancer, colorectal cancer; sarcomas, including leiomyosarcoma, rhabdomyosarcoma, liposarcoma, fibrosarcoma, and osteosarcoma; skin cancer, including melanoma, Kaposi's sarcoma, basocellular cancer, and squamous cell cancer; testicular cancer, including germinal tumors (seminoma, non-seminoma teratomas, and choriocarcinomas), stromal tumors, and germ cell tumors; thyroid cancer, including thyroid adenocarcinoma and medullar carcinoma; and renal cancer including adenocarcinoma and Wilms' tumor. In some important embodiments, the cancer is defined as an ErbB2 expressing cancer such as breast cancer, lung cancer, ovarian cancer, gastric cancer and bladder cancer. Inhibition of Grb7 interaction with PDGF can be for the prevention and/ore treatment of disorders involving PDGF such as atherosclerosis, myelofibrosis as well as some cancers. Preferably, the invention is directed at breast cancer and esophageal cancer. In some embodiments, the G7BPs of the invention are intended for the diagnosis, prevention, and/or treatment of some forms of retinopathies as well as some forms of autoimmune disease.

The Grb7 antagonists of the invention can also be used to prevent or inhibit metastasis. Tumor metastasis involves the spread of tumor cells primarily via the vasculature following the disassembly of tumor cell-ECM interactions through the degradation of the ECM, and tumor cell extravasation through the capillary bed. The invasion and metastasis of cancer is a complex process which involves changes in cell adhesion properties which allow a transformed cell to invade and migrate through the extracellular matrix (ECM) and acquire anchorage-independent growth properties. Liotta, L. A., et al., Cell 64:327-336 (1991). Some of these changes occur at focal adhesions, which are cell/ECM contact points containing membrane-associated, cytoskeletal, and intracellular signaling molecules. Metastatic disease occurs when the disseminated foci of tumor cells seed a tissue which supports their growth and propagation, and this secondary spread of tumor cells is responsible for the morbidity and mortality associated with the majority of cancers. Thus the term "metastasis" as used herein refers to the invasion and migration of tumor cells away from the primary tumor site.

Subjects having the disorder characterized by abnormal Grb7 interaction with one or more of its ligands include subjects who have a disorder such as cancer. These subjects may be identified using the diagnostic methods described herein, and/or the methods used to diagnose the cell proliferative disorders listed above, including physical exam and diagnostic imaging tests. The diagnosis of such disorders, including cell proliferative disorders such as cancer and metastasis, are well known in the art and are routinely practiced by medical professionals. The treatment method may further comprise the selection of a subject having the disorder prior to the administration of the Grb7 antagonist, according to the teaching provided herein.

The prophylactic methods of the invention are directed to subjects who are at risk of developing the disorder. Such a subject may also be identified using the diagnostic methods provided herein. Namely, a subject at risk may be one who exhibits an abnormal level of Grb7 or signaling factor expression products or one who exhibits an abnormal level of interaction of Grb7 with a signaling factor. Other subjects at risk of developing such a disorder may be those with a family history of such disorders. As an example, subjects with a family history of breast cancer and/or abnormal Grb7 and signaling factor interaction may be considered subjects for prophylactic treatment. Subjects at risk of certain disorders characterized by an abnormal interaction of Grb7 and its ligands may also be those who have previously been diagnosed and treated for such a disorder. An example of this is a subject who has previously been diagnosed and treated for breast cancer. This subject is at risk of redeveloping breast cancer either as a primary tumor or as a metastasis at a secondary site. In certain embodiments, the prophylactic methods further comprise first selecting a subject who is at risk of developing the disorder prior to the administration of the Grb7 antagonist.

The Grb7 antagonists of the invention are administered to a subject either at risk of developing the disorder or a subject having the disorder in an effective amount. The effective amount will depend upon the mode of administration, the particular condition being treated, and the desired outcome. It will also depend upon, as discussed above, the stage and severity of the condition, the subject to be treated including the age and physical condition of the subject, the nature of concurrent therapy, if any, and like factors well-known to the medical practitioner. For prophylactic applications, it is generally that amount sufficient to delay the onset of, inhibit the progression of, or halt altogether the particular condition sought to be prevented. For therapeutic applications, it is generally that amount sufficient to achieve a medically desirable result.

When used therapeutically, an effective amount may be that amount which inhibits the disorder. Such inhibition may be measured by an inhibition or a decrease in cell proliferation or, in some instances, tumor growth. Inhibition of tumor growth may be manifest as a reduction in the size of a tumor mass, or as a failure of the tumor to increase in size. When used prophylactically, an effective amount may be that amount which prevents a disorder from arising. Such inhibition may be measured by an absence of a tumor, perhaps manifest as a failure of the suspect tissue to increase in size or mass, or to develop a discernible tumor. If the subject to be treated already has a tumor, or is at risk of having a metastasis, the effective amount may also be that amount which prevents the spread of a primary tumor to secondary sites (i.e., an inhibition in metastasis). Thus, in one embodiment, the agent may be administered in an effective amount to inhibit metastasis, independent of its ability to inhibit primary tumor growth.

As shown in the Examples, the Grb7 antagonists have varying binding affinity for Grb7. This variation can be exploited in the treatment of subjects where it is necessary to control the extent of Grb7 inhibition desired either as a function of development or of time in a treatment regimen. Thus, early on in a subject's treatment it may be desirable to administer a higher affinity G7BP (such as G7BP-4) while later in the treatment (for example, during a remission) it may be more suitable to administer a lesser affinity G7BP (such as G7BP-4-NA).

The invention further embraces pharmaceutical preparations of Grb7 antagonists (e.g., G7BPs) and nucleic acid molecules encoding them. In particular, pharmaceutical preparations are provided which comprise antagonists which bind to Grb7 and preferably antagonists which interfere with signal transduction from the native binding partners of Grb7. An antagonist is present in the pharmaceutical preparation in a prophylactically or therapeutically effective amount. In addition the pharmaceutical preparation themselves will also contain a pharmaceutically acceptable carrier. The pharmaceutical preparations may themselves be administered in effective amounts, as described above.

Thus, the invention provides a composition of the above-described Grb7 inhibitors for use as a medicament, methods for preparing the medicament, and methods for the sustained release of the medicament in vivo.

Generally, doses of active compounds of the present invention would be from about 0.01 mg/kg per day to 1000 mg/kg per day. It is expected that doses ranging from 1-500 mg/kg, and preferably doses ranging from 1-100 mg/kg, and even more preferably doses ranging from 1-50 mg/kg, will be suitable. A variety of administration routes are available. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration may be preferred for prophylactic treatment because of the convenience to the patient as well as the dosing schedule. Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

When the compounds described herein (including peptide and non-peptide varieties) are used therapeutically, in certain embodiments a desirable route of administration may be by pulmonary aerosol. Techniques for preparing aerosol delivery systems containing compounds are well known to those of skill in the art. Generally, such systems should utilize components which will not significantly impair the biological properties of the compounds, for example the Grb7 binding capacity of the G7BPs (see, for example, Sciarra and Cutie, "Aerosols," in *Remington's Pharmaceutical Sciences,* 18th edition, 1990, pp 1694-1712; incorporated by reference). Those of skill in the art can readily determine the various parameters and conditions for producing aerosols without resort to undue experimentation.

The Grb7 antagonists of the invention, including the G7BPs, may be administered directly to a tissue. Preferably, the tissue is itself a tumor or it is a tissue in which the disorder exists. Alternatively, the tissue is one in which a tumor or disorder is likely to exist. For example, a subject at risk of developing breast cancer may be prophylactically treated by administering a G7BP into the breast tissue of the subject. Direct tissue administration may be achieved by direct injection. The G7BPs may be administered once, or alternatively they may be administered in a plurality of administrations. If administered multiple times, the G7BPs may be administered via different routes. For example, the first (or the first few) administrations may be made directly into the affected tissue while later administrations may be systemic.

G7BPs may also be targeted to a tissue using targeting compound such as ligands specific for a particular tissue or tumor type. The agents of the invention may be targeted to primary or, in some instances, secondary (i.e., metastatic) lesions through the use of targeting compounds which preferentially recognize a cell surface marker. The targeting compound may be directly conjugated to the agents of the invention via a covalent linkage. The agent may be indirectly conjugated to a targeting compound via a linker. Methods of conjugation suitable in the invention have been described elsewhere herein. Alternatively, the targeting compound may be conjugated or associated with an intermediary compound such as, for example, a liposome within which the agent is encapsulated. Liposomes are artificial membrane vessels which are useful as a delivery vector in vivo or in vitro. It has been shown that large unilamellar vessels (LUV), which range in size from 0.2-4.0 µm can encapsulate large macromolecules. Liposomes may be targeted to a particular tissue, such as the vascular cell wall, by coupling the liposome to a specific ligand such as a monoclonal antibody, sugar, glycolipid, or protein. Liposomes are commercially available from Gibco BRL, for example, as LIPOFECTIN™ and LIPOFECTACE™, which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology*, V. 3, p. 235-241 (1985). In still other embodiments, the targeting compound may be loosely associated with the antagonists of the invention, such as within a microparticle comprising a polymer, the antagonist and the targeting compound.

Targeting compounds useful according to the methods of the invention are those which direct the antagonist to a site of a disorder characterized by Grb7 interaction with a Grb7 ligand (e.g., a tumor). The targeting compound of choice will depend upon the nature of, for example, the tumor or the tissue origin of the metastasis. In some instances it may be desirable to target the agent to the tissue in which the tumor is located. As an example, agents can be delivered to breast epithelium by using a targeting compound specific for breast tissue. In important embodiments, the target is specific for malignant breast epithelium. Examples of compounds which may localize to malignant breast epithelium include, but are not limited to, estrogen and progesterone, epithelial growth factor (EGF) and HER-2/neu ligand, among others. The HER-2/neu ligand may also be used to target agents to ovarian cancers. Ovarian cancers are also known to express EGFR and c-fins, and thus could be targeted through the use of ligands for either receptor. In the case of c-fins which is also expressed by macrophages and monocytes, targeted delivery to an ovarian cancer may require a combination of local administration such as a vaginal suppository as well as a targeting compound. Prostate cancers can be targeted using compounds such as peptides (e.g., antibodies or antibody fragments) which bind to prostate specific antigen (PSA) or prostate specific membrane antigen (PSMA). Other markers which may be used for targeting of the agent to specific tissues include, for example, in liver: HGF, insulin-like growth factor I, II, insulin, OV-6, HEA-125, hyaluronic acid, collagen, N-terminal propeptide of collagen type III, mannose/N-acetylglucosamine, asialoglycoprotein, tissue plasminogen activator, low density lipoprotein, carcinoembryonic antigen; in kidney cells: angiotensin II, vasopressin, antibodies to CD44v6; in keratinocytes and skin fibroblasts: KGF, very low density lipoprotein, RGD-containing peptides, collagen, laminin; in melanocytes: kit ligand; in gut: cobalamin-intrinsic factor, heat stable enterotoxin of *E. coli*; in breast epithelium: heregulin, prolactin, transferrin, cadherin-11. Other markers specific to particular tissues are available and would be known to one of ordinary skill in the art. In still other embodiments, the agent of the invention may be targeted to fibroblasts via ligands or binding partners for fibroblast specific markers. Examples of these markers include, but are not limited to fibroblast growth factors (FGF) and platelet derived growth factor (PDGF).

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

As mentioned earlier, the Grb7 inhibitors may be combined, optionally, with a pharmaceutically-acceptable carrier. The term "pharmaceutically-acceptable carrier" as used herein means one or more compatible solid or liquid filler, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being commingled with the agents of the present invention, and with each other, in a manner such that there is no interaction which would substantially impair the desired pharmaceutical efficacy.

When administered, the pharmaceutical preparations of the invention are applied in pharmaceutically-acceptable amounts and in pharmaceutically-acceptable compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

In yet other embodiments, the preferred vehicle is a biocompatible microparticle or implant that is suitable for implantation into the mammalian recipient. Exemplary bioerodible implants that are useful in accordance with this method are described in PCT International Application No. PCT/US/03307 (Publication No. WO 95/24929, entitled "Polymeric Gene Delivery System", claiming priority to U.S. patent application Ser. No. 213,668, filed Mar. 15, 1994). PCT/US/0307 describes a biocompatible, preferably biodegradable polymeric matrix for containing a biological macromolecule. The polymeric matrix may be used to achieve sustained release of the agent in a subject. In accordance with one aspect of the instant invention, the agent described herein may be encapsulated or dispersed within the biocompatible, preferably biodegradable polymeric matrix disclosed in PCT/US/03307. The polymeric matrix preferably is in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents of the invention may be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the Grb7 inhibitor, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for prophylactic treatment of subjects at risk of having a disorder characterized by abnormal interaction of Grb7 and a Grb7 ligand. Long-term release, as used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

In other aspects, the Grb7 antagonists of the invention are co-administered with another agent. In some embodiments, the agents may be administered substantially simultaneously with the other, preferably therapeutic, agents. By substantially simultaneously, it is meant that a Grb7 antagonist of the invention (e.g., G7BP-1, G7BP-2, G7BP-3, G7BP-4, G7BP-5, G7BP-6 or G7BP-7) is administered to a subject close enough in time with the administration of the other therapeutic agent, whereby the two compounds may exert an additive or even synergistic effect. In some instances, the antagonist and the other therapeutic agent are conjugated to each other. In others, the compounds are physically separate.

The agents of the invention may be administered with several categories of therapeutic agents. In certain embodiments the agent can be administered, as mentioned earlier, in combination with therapeutic agents which are anti-cancer agents. Anti-cancer agents are agents which possess a preferential cytotoxicity towards malignant cells. Examples of anti-cancer agents include but are not limited to: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Sinitrazene; Sparfosate Sodium; Sparsomycin; Spirogermanium Hydrochloride; Spiromustine; Spiroplatin; Streptonigrin; Streptozocin; Sulofenur; Talisomycin; Tecogalan Sodium; Tegafur; Teloxantrone Hydrochloride; Taxol; Taxotere; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other anti-cancer drugs include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins;

iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A +myobacterium cell wall sk; mopidamol; multiple drug resistance gene inhibitor; multiple tumor suppressor 1-based therapy; mustard anti cancer compound; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Anti-cancer supplementary potentiating compounds include: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and multiple drug resistance reducing compounds such as Cremaphor EL.

Other compounds which are useful in combination therapy for the purpose of the invention include the anti-proliferation compound, Piritrexim Isethionate; the antiprostatic hypertrophy compound, Sitogluside; the benign prostatic hyperplasia therapy compound, Tamsulosin Hydrochloride; the prostate growth inhibitor, Pentomone; radioactive compounds such as Fibrinogen 1125, Fludeoxyglucose F 18, Fluorodopa F 18, Insulin I 125, Insulin I 131, Iobenguane I 123, Iodipamide Sodium I 131, Iodoantipyrine I 131, Iodocholesterol I 131, Iodohippurate Sodium I 123, Iodohippurate Sodium I 125, Iodohippurate Sodium I 131, Iodopyracet I 125, Iodopyracet I 131, Iofetamine Hydrochloride I 123, Iomethin I 125, Iomethin I 131, Iothalamate Sodium I 125, Iothalamate Sodium I 131, Iotyrosine I 131, Liothyronine I 125, Liothyronine I 131, Merisoprol Acetate Hg 197, Merisoprol Acetate Hg 203, Merisoprol Hg 197, Selenomethionine Se 75, Technetium Tc 99m Antimony Trisulfide Colloid, Technetium Tc 99m Bicisate, Technetium Tc 99m Disofenin, Technetium Tc 99m Etidronate, Technetium Tc 99m Exametazime, Technetium Tc 99m Furifosmin, Technetium Tc 99m Gluceptate, Technetium Tc 99m Lidofenin, Technetium Tc 99m Mebrofenin, Technetium Tc 99m Medronate, Technetium Tc 99m Medronate Disodium, Technetium Tc 99m Mertiatide, Technetium Tc 99m Oxidronate, Technetium Tc 99m Pentetate, Technetium Tc 99m Pentetate Calcium Trisodium, Technetium Tc 99m Sestamibi, Technetium Tc 99m Siboroxime, Technetium Tc 99m Succimer, Technetium Tc 99m Sulfur Colloid, Technetium Tc 99m Teboroxime, Technetium Tc 99m Tetrofosmin, Technetium Tc 99m Tiatide, Thyroxine I 125, Thyroxine I 131, Tolpovidone I 131, Triolein I 125 and Triolein I 131.

TABLE 1

Peptide GenBank Accession Numbers

G7BP-1

AAD33672.1, CAA08765.1, AAF57850.1, AAF46412.1, AAF48202.1, P17137, O13368, Q00422, Q06546, NP_059119.1, AAF76451.1, NP_010601.1, 1786519 (AE000139), 1789462 (AE000390), 1790056 (AE000440), 1787116 (AE000191), 1AWC, AAE03740.1, CAA01933.1, AAA93714.1, T01232, T23954, C70879, JC4110, S71361, A48146, T02914, T29233, T32875, G69189

G7BP-2

AAD24572.1, NP_006453.1, JC5983, AAF51052.1, AAF50522.1, AAF56991.1, P13779, Q04370, AAF73601.1, AAF73635.1, AAF79407.1, NP_013739.1, NP_014814.1, NP_013624.1, NP_012257.1, NP_010521.1, 1RDG, 1DAN, M21005_HSAL002524_rf-3, L05173_HSAL001270_rf-1, AAA55227.1, AAA53821.1, 1789087 (AE000357), JC5983, T21560, T40445, D71511, A70695, A30363, T03179, B70729, A72104, T06144, A36705, A69263, T32331, B47417, S54784, I48771, A29176, B71610, T08428, T03137, T26480, S18199, B72062, JC4321, T26562, S33879, T08947, T37255

G7BP-3

AAF17214.1, AAF17488.1, AAF17490.1, AAF17489.1, NP_038474.1, AAF17487.1, AAD51405.1, AAA99070.1, NP_014132.1, AAF62454.1, NP_036159.1, AAF44494.1, CAB46239.1, AAC67235.1, T18431, T20713, T02265, AAF58590.1, AAF54518.1, AAF54335.1, AAF51070.1, CAB95239.1, P39104, P25167, O89042, P33609, P36963, 1ROT, AAC89537.1, AAC89548.1, AAC89549.1, AAC87495.1, AAC89547.1, AAC87496.1, AAE06363.1, AAE06364.1, NP_014132.1, NP_015348.1, NP_014471.1, NP_010844.1, NP_011309.1, 1789161 (AE000363), 1787108 (AE000190), 1788013 (AE000267), L22740_HSAL004720_rf1, X62902_HSAL000350_rf-2

G7BP-4

BAA92321.1, AAF42105.1, T32386, NP_009940.1, BAA22939.1, NP_032760.1, AAF50769.1, AAF45403.1, AAF79407.1, AAF79379.1, P25615, P76318, P11467, P27738, P03833, P14412, P40943, 2HIP, NP_009940.1, NP_014681.1, L11910_HSAL002841_rf-3, X02419_HSAL001048_rf-2, NP_009940.1, NP_014681.1, 1788240 (AE000285), 1788041 (AE000269)

G7BP-5

F71065, AAC35918.1, AAF60832.1, P22382, AAF33670.1, AAF59107.1, AAF52233.1, AAF52232.1, CAB95077.1, CAB95077.1, AAF75220.1, AAF75222.1, AAF75221.1, P22382, P38147, P04351, 1AGI, AAA01624.1, AAA01622.1, M33613_HSAL002172_rf1, M86165_HSAL003675_rf-3, NP_009833.1, NP_015271.1, NP_015155.1, 1790145 (AE000448), 1788417 (AE000299)

G7BP-6

T04906, AAF79267.1, T01867, T28626, CAB06038.1, AAF47844.1, AAF48518.1, AAF56320.1, AAF79267.1, AAF79353.1, Q07327, P26314, P55201, P31627, P25190, P36334, P41413, P25192, Q04592, 1EGD, M80651_HSAL001553_rf-3, Z15027_HSAL000627_rf-1, NP_011384.1, NP_009441.1, NP_014142.1, NP_013105.1, 1790173 (AE000450), AAE21397.1, AAE21398.1, AAE03587.1, CAB69283.1, CAB69284.1, AAC11735.1, AAE03589.1, AAE03586.1, AAE03588.1,

G7BP-7

T20778, AAF14258.1, CAA10281.1, T276677, T23551, CAB85311.1, AAF47629.1, AAF56505.1, BAA33512.2, BAA33512.2, P75059, P47288, P25202, Q50203, P56370, P05813, 1GUP, 1HXP, 1HXQ, 1HXQ, AAE06141.1, X55502_HSAL000745_rf2, NP_009833.1, 1786973 (AE000178), 1786848 (AE000167)

TABLE 2

Nucleic Acid GenBank Accession Numbers

G7BP-1

AC004561.2, AE001438.2, AC068960.2, AC009998.2, AL355141.4, AL356157.6, AC069181.2, AC008758.4, AC067903.2, AZ203004.1, AZ203003.1, AP001113.2, NC_001133.1, NC_001147.1, NC_001136.1, NC_001224.1, AE000244, AE000139, 1C2W, E00614.1, I03580.1, AE003538.1, AE003609.1, AE002816.1, AE003767.1, AI078971.1, AW506481.1, AI999706.1, BE195390.1, AA463274.1, AW706216.1, AI721582.1, AI096231.1, AI442270.1, AW996680.1, AW976605.1, AW940293.1, AW268626.1, AI356279.1, AA550180.1, AL145207.1, G36364.1, AW046412.1, AA726027.1, AA672792.1, AA666983.1, L05669.1, D31785, AA463274.1, AW996680.1, AW976605.1, AW268626.1, AI356279.1, AI078971.1, AW506481.1, AI999706.1, BE195390.1, AW706216.1, AI721582.1, AI096231.1, AW940293.1, AA550180.1, AI442270.1, AZ203004.1, AZ203003.1, AZ251981.1, AQ827443.1, AQ378354.1, AQ217128.1, AZ129573.1, AQ539625.1, AQ284608.1, AZ099151.1, AZ204867.1, AZ204343.1, AZ165319.1, AL105293.1, AL077560.1, AQ798100.1, AQ188033.1, AQ024253.1, AC068960.2, AC009998.2, AL355141.4, AL356157.6, AC069181.2, AC008758.4, AC067903.2, AC022605.3,

G7BP-2

AF070064.1, AJ286313.1, U55198.1, AL132985.2, AE003742.1, AF124663.1, NM_006462.1, AF061234.1, U67322.1, U48248.1, AL079333.7, AB011369.1, AF045679.1, AF045670.1, AL326907.1, AL138817.6, AL357153.1, BE032989.1, AC018547.7, AC026227.2, AC069083.2, AL121747.23, AC023050.14, AC008083.15, AL139398.3, AZ195903.1, AZ154671.1, NC_001145.1, AE000481, AE000349, A37267.1, AL155313.1, G10149.1, AF224994.1, G42404.1, Z53535.1, G18081.1, AW654578.1, BE032989.1, AW692180.1, AW321695.1, AI909655.1, AA895282.1, AA451409.1, AA135664.1, AA108185.1, W97233.1,

TABLE 2-continued

Nucleic Acid GenBank Accession Numbers

N99547.1, AI379209.1, AW321695.1, AA895282.1, AA451409.1, AA108185.1, W97233.1, AI909655.1,
AA135664.1, N99547.1, AI379209.1, AW654578.1, BE032989.1, AW692180.1, AE003742.1, AL326907.1,
AL194173.1, AQ221847.1, AQ188276.1, AQ840552.1, AQ147099.1, AZ195903.1, AZ154671.1, AQ163491.1,
AC019109.3, AL138817.6, AC022995.2, AL357153.1, AC064809.2, AC023415.3, AC009269.2, AC018547.8,
AC026227.2, AC069083.2, AC023902.3, AC025364.2, AC020026.1, AL121747.23, AC023050.14,
AC008083.15, AC027010.2, AC021810.3, AL139398.3, AC073235.1,
G7BP-3

Z92804.1, AC007286.18, AC006582.13, AC005266.1, AC005744.2, AF219467.1, AF117233.1, X89088.1,
AL033544.15, AF188714.1, AF192785.1, AC073045.1, AC011747.4, AL161633.3, AC073345.1, AL158819.3,
E01028.1, AI099017.1, AI019877.1, AA499169.1, AA120494.1, AE003739.1, AE003421.1, AI099017.1,
N80502.1, AW656545.1, AW344766.1, AI019877.1, AA499169.1, AA120494.1, G54774.1, N80502.1,
AW656545.1, AW344766.1, AQ304345.1, AL098716.1, AQ659126.1, AQ254392.1, AC009485.2,
AC073045.1, AC021717.3, AC024685.2, AC011747.4, AC021669.1, AL161633.3, AC073345.1, AC011399.2,
AC008438.3, AC025971.2, AL139387.3, AL158819.3, AC013484.11, AC013485.1, AL160053.5,
G7BP-4

AL161713.3, L15440.1, L78810.1, AC004973.1, AF067844.1, Z77670.1, AL031678.2, AE003808.1,
AC004516.1, AL163032.2, D89663.1, D89662.1, D89661.1, U53583.1, AL138780.3, AL035689.26, M88253.1,
AP001692.1, AC024718.4, AL121899.23, AL356142.3, AC016731.3, AC069282.2, AC025591.7, AC073119.1,
AC027262.2, AL139338.4, AC073488.3, AL356805.2, AC026095.2, AL138801.8, AR052312.1, I28252.1,
AE003808.1, H74240.1, AI966612.1, AI966597.1, AI496521.1, AI403160.1, AA403198.1, AA875320.1,
X87259.1, G28440.1, C79322.1, AV067115.1, AI226547.1, BE199949.1, AV213868.1, AA538060.1,
H74240.1, AA403198.1, AI966612.1, AI966597.1, AI496521.1, AI403160.1, AA875320.1, AQ783079.1,
AQ807863.1, AQ925923.1, AQ519733.1, AQ438650.1, AC056415.1, AC047157.1, AC047156.1, AC040643.1,
AC024718.4, AC063965.2, AC013669.2, AL121899.23, AL356142.3, AC016731.3, AC069282.2, AC025591.7,
AC073119.1, AC019066.4, AC027262.2, AC011880.4, AL139338.4, AC073488.3, AC025937.3, AC027255.1,
AC023958.2, AC020355.1, AC007579.3, AC007194.1, AC004426.1, AL356805.2, AL354744.1, AC016087.5,
AC026095.2, AC024042.3, AC055869.2, AC068104.1, AC023879.2, AL138801.8, AL136163.4,
G7BP-5

AC006147.2, AC027663.14, Z82194.1, AE003570.1, U66106.1, AL356799.2, AL078591.18, AJ237644.1,
D90902.1, AC026741.4, AP000596.2, AC073256.2, AP000810.2, AL138801.8, AC007341.4, AC068717.2,
AC023059.8, AL161851.2, AL135901.8, AL354956.2, AL136301.9, BB052012.1, BB027656.1, AP001098.3,
AC063952.6, AC009753.4, BB052012.1, BB027656.1, AW693883.1, AU009095.1, AE003570.1, BB052012.1,
BB027656.1, AU009095.1, AW693883.1, AJ232119.1, AQ345383.1, AC024927.2, AC025454.3, AC019267.3,
AC018853.3, AC008902.3, AC026741.4, AC073256.2, AP000810.2, AP000596.2, AC023879.2, AC022661.2,
AL138801.8, AC007341.4, AC008869.3, AC068717.2, AC023156.3, AC023059.8, AL161851.2, AP001098.3,
AC025408.3, AC015992.3, AC022040.2, AL135901.8, AL354956.2, AL136301.9, AL162405.2, AC063952.6,
AC009753.4, AC023393.3, AC011706.13, AC010917.15, AC014555.1,
G7BP-6

AL031587.3, Z92540.1, AE003543.1, AF128626.1, AL160394.6, AL355504.5, BE075250.1,
AE003543.1, AV282789.1, AW213936.1, BE075250.1, AU060639.1, AU060595.1, AV282789.1,
AW213936.1, BE075250.1, AU060639.1, AU060595.1, AQ290210.1, AC040898.2, AC068330.1, AC021920.1,
AL159160.8, AL160394.6, AL355504.5, Z84464.1, AC013494.3, AC014959.1,
G7BP-7

AC002443.1, AE003667.1, AL357044.8, AE003667.1, AV087190.1, AV287042.1, AV226864.1, AV149656.1,
AV080866.1, AV130186.1, AV329897.1, AV321951.1, AV164613.1, AV045278.2, AV042911.2, AV087190.1,
AV287042.1, AV226864.1, AV149656.1, AV080866.1, AV130186.1, AV329897.1, AV321951.1, AV164613.1,
AV045278.2, AV042911.2, AV039422.2, AV025848.1, AV025351.1, AV224494.1, AV091378.1, AV026396.1,
BB094539.1, BB008250.1, AV242898.1, AV240612.1, AV222545.1, AV170949.1, AV091298.1, AV036505.1,
AV029816.1, AV027656.1, AV026412.1, AV026374.1, AV026201.1, AV026197.1, AV026170.1, AV026074.1,
AV026047.1, AV026008.1, AV025710.1, AV025703.1, AV025667.1, AV025588.1, AV025559.1, AV025450.1,
AV025429.1, AV025411.1, AV025331.1, AV025283.1, AV025119.1, AV024891.1, AV024878.1, AV024871.1,
AV024437.1, AV024297.1, AV285784.1, AV026455.1, AV026162.1, AV025352.1, AQ224850.1, AL357044.8,
AC018216.1,

The following examples are included for purposes of illustration and are not intended to limit the scope of the invention.

EXAMPLES

Example 1

Identification of G7BP

The G7BPs were identified using peptide phage display techniques. Two phage display libraries were created and screened that led to the identification of these peptides. The first library was a random peptide phage-display library containing more than $10^7$ different cyclic decapeptides flanked at each end by regions of four amino acids, according to the following general motif: $X_4$ C $X_{10}$ C $X_4$ (X=any amino acid residue, C=cysteine). These sequences are displayed on the gene III protein of the fd FuseV phage system (Scott and Smith 1990 Science 249:386-390). The SH2 domain of human Grb7 containing a GST fusion tag was purified from an *E. coli* expression system. The random 10mer library was screened using standard phage display methodology (Smith GP. 1985. Science. 228:1315-7). The phage library was added to the target protein which was immobilized on glutathione Sepharose beads (Pharmacia). The unbound phage were removed with a series of washes and the bound phage were eluted by competitive elution with excess glutathione. These bound phage were allowed to infect E. coli in order to amplify the eluted phage. This screening process was repeated two times for a total of three rounds of screening. After the third round of screening, clones from the amplified phage were isolated and sequenced. Thirty-nine clones were characterized and all contained a Y-A/D/E-N motif, where the +2 position was enriched for alanine, aspartic acid, and glutamic acid. The second library, biased for this Y-A/D/E-N motif, was created in the same FuseV phage display system. This biased library contained over 10⁶ different clones. Screening of this library was carried out using the same procedure used with the random library, however screening this library resulted in peptides that bind strongly and specifically to Grb7 SH2 domain in an ELISA assay, as shown in FIG. 1. The sequences of these seven peptides are shown in Table 3.

TABLE 3

Sequences of G7BP-1 Peptides

| Peptide | Sequence | SEQ ID NO: |
|---|---|---|
| G7BP-1 | RVQE C KYLY YDN DYL C KDDG | 1 |
| G7BP-2 | KLFW C TYED YAN EWP C PGYS | 2 |
| G7BP-3 | NVSE C IYIH YDN WSL C GVEV | 3 |
| G7BP-4* | GVSN C VFWG YAN DWL C SDYS | 4 |
| G7BP-5** | RSTL C WFEG YDN TFP C KYFR | 5 |
| G7BP-6 | FCAV C NEEL YEN CGG C SVGK | 6 |
| G7BP-7 | RTSP C GYIG YDN IFE C TYLG | 7 |
| G7BP-1NA | C KYLY YDN DYL C | 39 |
| G7BP-2NA | C TYED YAN EWP C | 40 |
| G7BP-3NA | C IYIH YDN WSL C | 41 |
| G7BP-4NA* | C VFWG YAN DWL C | 35 |
| G7BP-5NA** | C WFEG YDN TFP C | 42 |
| G7BP-6NA | C NEEL YEN CGG C | 43 |
| G7BP-7NA | C GYIG YDN IFE C | 44 |
| G7BP-1NATE | ⌢KYLY YDN DYL C⌢ | 47 |
| G7BP-2NATE | ⌢TYED YAN EWP C⌢ | 48 |
| G7BP-3NATE | ⌢IYIH YDN WSL C⌢ | 49 |
| G7BP-4NATE* | ⌢VFWG YAN DWL C⌢ | 50 |
| G7BP-5NATE** | ⌢WFEG YDN TFP C⌢ | 51 |
| G7BP-6NATE | ⌢NEEL YEN CGG C⌢ | 52 |
| G7BP-7NATE | ⌢GYIG YDN IFE C⌢ | 53 |

*G7BP-4 is also referred to as G7-8
G7BP-4NA is also referred to as G7-8NA
G7BP-4NATE is also referred to as G7-8NATE
**G7BP-5 is also referred to herein as G7-18
G7BP-5NA is also referred to herein as G7-18NA
G7BP-5NATE is also referred to herein as G7-18NATE
⌢ signifies a thioether bond between the ends of the peptide Example 2

Grb7 Specificity of the G7BP

Figure 2:
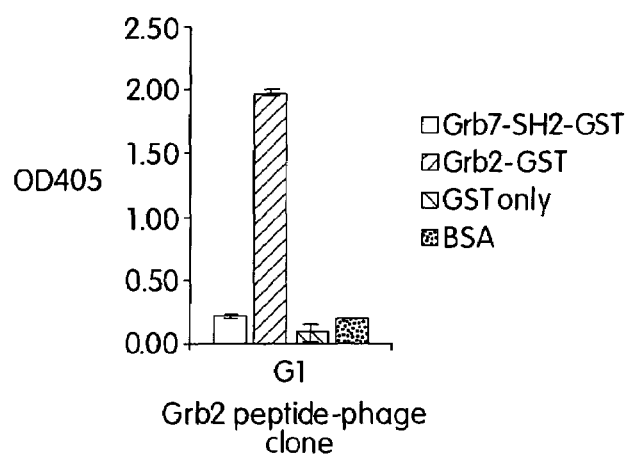
FIG. 2 is a histogram showing the binding of a control phage clone to the SH2 domain of Grb2 but not to the SH2 domain of Grb7.

An ELISA binding assay was used to determine whether the peptide-phage bind specifically to the SH2 domain of Grb7, and not to the fusion protein (GST) or other SH2 domains that are homologous to Grb7. The overall methodology of an ELISA is well established. Four different proteins were bound to a polystyrene 96-well plate: Grb7-SH2 domain-GST, GST alone, Grb2-GST and BSA as a non-specific negative control. Preparations of the concentrated Grb7 peptide-phage clones were allowed to bind to these proteins. Non-specific binding was blocked by casein. Binding of phage was detected using an anti-phage antibody conjugated to horseradish peroxidase. As seen in FIG. 1, these seven peptide-phage clones bind strongly to Grb7 SH2 domain and not to the other proteins. FIG. 2 shows binding of a control phage clone which displays a peptide which binds specifically to the SH2 domain of Grb2 (Oligino et. al. 1997 J. Biol. Chem. 272: 229046-29052). This peptide contains the YXN motif but does not bind to Grb7, showing that the peptides identified in this manner are specific for the Grb7 SH2 domain and that binding to Grb7 is not a general characteristic of fd phage or any YXN motif peptide.

These peptides are the first non-phosphorylated peptides identified which bind to the SH2 domain of Grb7. Inhibition of SH2 domain function of Grb7 has been previously attempted using peptides that contain a phosphotyrosine (Janes et al 1997. J Biol Chem 272: 8490-8497). However these phosphorylated peptides are not stable inside living cells and therefore unlikely to be effective long-lasting cancer therapeutics. Having a non-phosphorylated peptide provides a more stable structure, eliminating the problem of the loss of a phosphorylated tyrosine via the activity of endogenous phosphatases. Additionally, these Grb7-binding peptides offer improved cell penetration, as they do not contain a charged residue on the tyrosine, while still maintaining specificity for Grb7.

Example 3

Mutagenesis of peptides

Different portions of the peptides have been modified to determine which regions, primary sequences and/or three dimensional structure and charge distribution, are important for binding to Grb7. These modifications include (1) substituting serine or valine for the fixed cysteines (at positions 5 and 16) to determine if the peptides need to be cyclic, (2) removing the 4 amino acids flanking the cysteines, (3) minimizing the number (and size) of the amino acids between the cysteines, and (4) changing the location of the YXN motif within the peptide relative to the ends and the cysteines.

Figure 3:
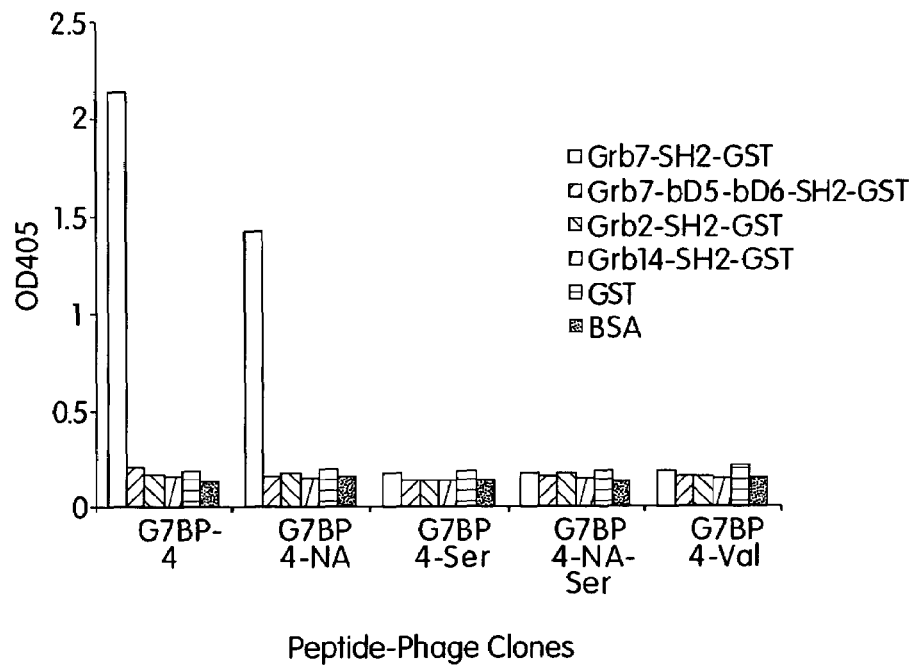
FIG. 3 is a histogram showing the effect of mutation on a G7BP-4 phage clone on its ability to bind to the SH2 domain of Grb7.

Mutational analysis of G7BP-4 has been conducted to determine which amino acid residues are important in peptide binding to Grb7-SH2 as well as to determine the size restriction of these peptides. The mutations for G7BP-4 include the following: (1) eliminating the 4 amino acids flanking the cysteines (CVFGYANDWLC, SEQ ID NO:35) referred to as G7BP4-No Arms (NA), (2) mutating the cysteines to serine residues (GVSNSVFGYANDWLSSDYS, SEQ ID NO:36), which are structurally very similar, referred to as G7BP4-Ser, (3) mutating the cysteines to valine residues (GVSNVVFGYANDWLVSDYS, SEQ ID NO:37), which is similar in structure and charge, and (4) a combination where the cysteines were mutated to serines and the 4 flanking amino acids were removed (SVFGYANDWLS, SEQ ID NO:38), referred to as G7BP-No Arms(NA)-Ser. The substitutions of valine and serine for cysteine will eliminate the peptides ability to form a disulfide loop. The mutations were created as a DNA oligo, ligated into the fuse5 vector, and expressed as a peptide-phage. The resultant phage were tested in a phage ELISA for their ability to bind to Grb7-SH2-GST. The results shown in FIG. 3 indicate the that the cysteines are important for G7BP-4 binding to the Grb7-SH2 domain, and that substitution of cysteine with either valine or serine residues reducing the binding capacity. This data suggest that peptides with the sequence of G7BP-4 are more effective in a cyclic form than in a linear form. In addition, eliminating the 4 amino acids flanking the cysteine residues in G7BP-4 did not effect its ability to bind to the Grb7-SH2 domain, suggesting that the amino acids essential for binding to the SH2 domain are primarily located between the cysteine residues in this peptide. Variants of the G7BP-1, G7BP-2, G7BP-3, G7BP-5, G7BP-6 and G7BP-7 which similarly lack the 4 tracking amino acids on both ends can also bind specifically to Grb7. These peptides have the following amino acid sequences respectively:

```
G7BP-1NA:    C KYLY YDN DYL C    (SEQ ID NO:39);
G7BP-2NA:    C TYED YAN EWP C    (SEQ ID NO:40);
G7BP-3NA:    C IYIH YDN WSL C    (SEQ ID NO:41);
G7BP-5NA:    C WFEG YDN TFP C    (SEQ ID NO:42);
G7BP-6NA:    C NEEL YEN CGG C    (SEQ ID NO:43); and
G7BP-7NA:    C GYIG YDN IFE C    (SEQ ID NO:44).
```

Example 4

Specificity of Peptides

Figure 4:
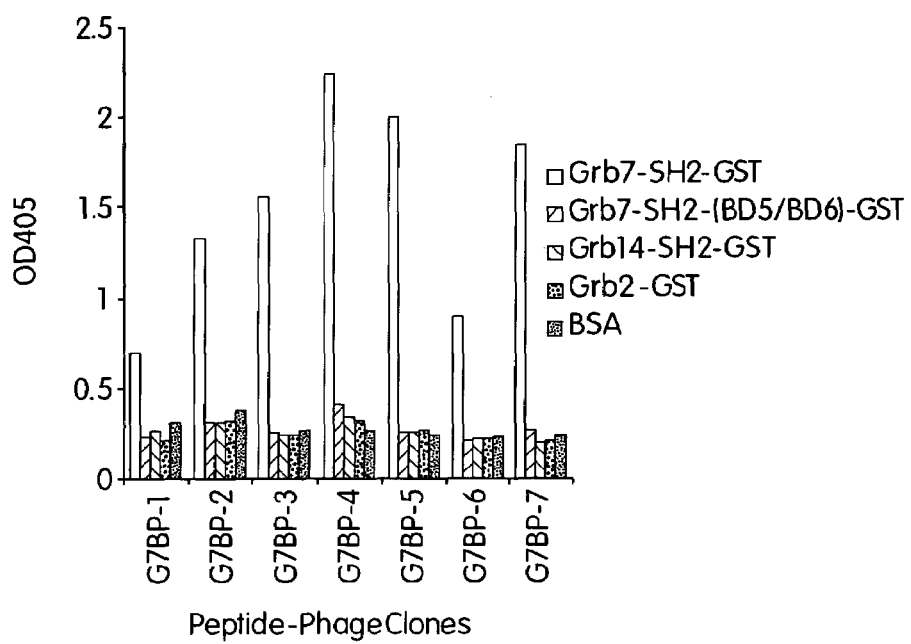
FIG. 4 is a histogram showing the binding specificity of seven Grb7 binding peptides to the SH2 domains of Grb7, Grb7 βD5-βD6, Grb14, full length Grb2, and BSA using a phage ELISA.

The ability of Grb7 peptide-phage and free peptides to bind homologous proteins is tested. The SH2 domain of Grb2 is 50% similar to Grb7 on the amino acid level and binds to the same site on ErbB2. The SH2 domain of Grb14 is 81% similar to Grb7 on the amino acid level but Grb14 does not bind ErbB2. As shown in FIG. 4, Grb7 binding peptide-phage clones G7P-1 through to G7BP-7, inclusive, do not bind to Grb14, despite the high homology between Gr7 and Grb14 SH2 domains. The results indicate that the Grb7 binding peptides are unable to bind to Grb14-SH2-GST or Grb2-GST indicating that the peptides are specific for Grb7 only. There are other SH2 containing proteins, such as PI3-kinase and Shc, which are being used to further test the specificity of the newly identified non-phosphorylated G7BP.

Example 5

Testing Binding Affinity of the Free Peptides

Figure 5A:
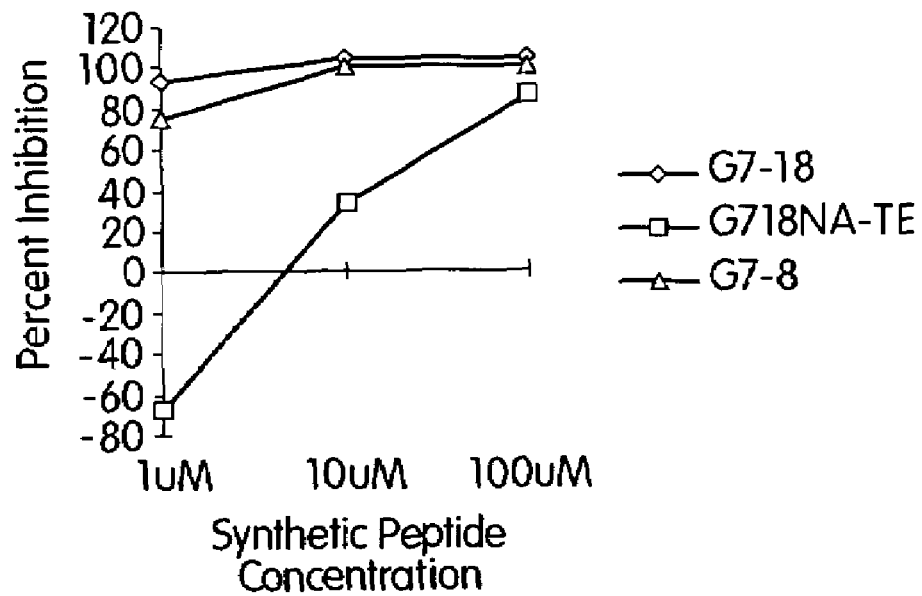
FIG. 5A is a graph showing the inhibition of G7-18 peptide-phage binding to Grb7-SH2 with the free synthetic peptides G7-18, G7-18NATE and G7-8.
Figure 5B:
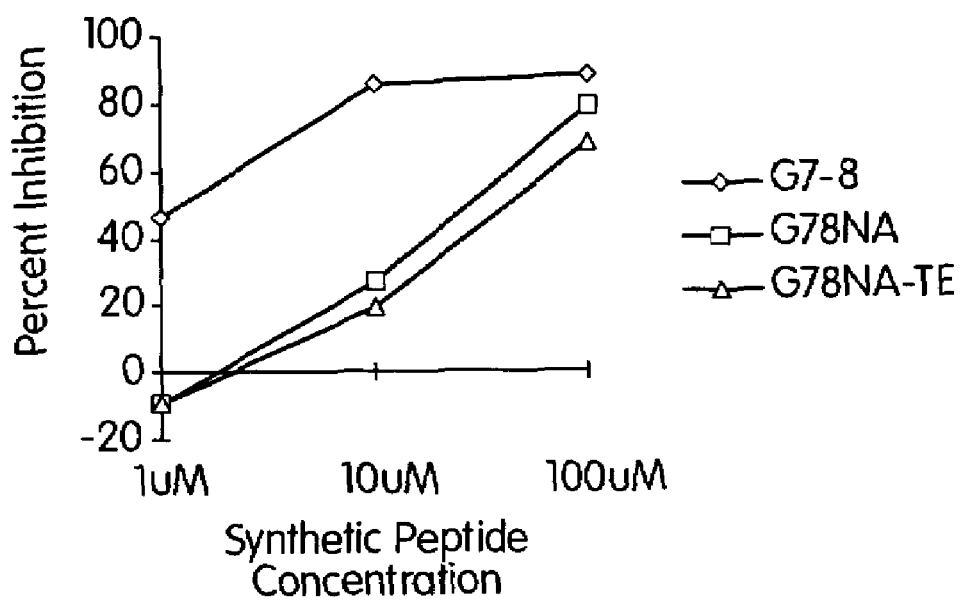
FIG. 5B is a graph showing the inhibition of G7-8NA peptide-phage binding to Grb7-SH2 with the free synthetic peptides G7-8, G7-8NA and G7-8NATE.

The relative ability of the free synthetic Grb7-binding peptides (G7-8 and G7-18) to inhibit the interaction between the Grb7 binding peptide-phage and Grb7-SH2 was determined in competition ELISA. Purified Grb7-SH2-GST (5 ug/ml) was added to the pre-coated anti-GST plate and blocked with casein in Tris-Buffered Saline (TBS) (Pierce). The G7-18 (FIG. 5A) and G7-8NA (FIG. 5B) peptide-phage were concentrated with standard polyethylene glycol precipitation methods and added to each well ($1 \times 10^6$ phage/well) in the presence of synthetic peptides or without (control). G7-18 peptide-phage competitors were G7-18, G7-18NATE and G7-8 free synthetic peptides (FIG. 5A). G7-8NA peptide-phage competitors were G7-8, G7-8NA and G7-8NATE free synthetic peptides (FIG. 5B). The synthetic peptides were mixed at different concentrations (1, 10, 100 uM) with peptide-phage before adding to Grb7-SH2-GST. Unbound phage were washed away with Tween-TBS buffer and bound phage were detected with anti-M13-horseradish peroxidase (Amersham-Pharmacia Biotech) and ABTS substrate (Calbiochem). Phage was detected by anti-M13-HRP antibody conjugate and detected using ABTS substrate. Plates were read at $OD_{405}$. Percent inhibition was calculated as follows: $100 \times (Y_{max}-Y)/Y_{max}$, where $Y_{max}$ is equal to $A_{405}$ in the absence of competitor, and Y is equal to the $A_{405}$ in the presence of the synthetic peptides.

FIGS. 5A and 5B illustrate that free synthetic peptides and their respective peptide-phage clone bind to the same sites. In addition, free synthetic G7-8 inhibits G7-18 peptide-phage, demonstrating that both peptides are binding to the same site. No inhibition was seen with N1480 peptide, which is an PI3 kinase-SH2-binding peptide (DpYVPML, SEQ ID NO:45) (data not shown). Additionally, the synthetic Grb7-binding peptides do not inhibit Grb2-binding peptide-phage, further demonstrating that this is a specific interaction (data not shown). In preparation for the in vitro experiments, the disulfide bond was replaced by a thioether bond, because of the instability of a disulfide bond potentially caused by the reduction in cell lysate conditions, as discussed Oligino et al. 1997. Inhibition is also achieved with thioether containing peptides (G7-8NATE and G7-18NATE), but to a lesser extent than seen with the disulfide containing peptides, also shown in FIGS. 5A and 5B. As these thioether containing peptides also lack the 4 amino acid sequences that flank the cysteine residues of G7BP-1 through to G7BP-7 (i.e., the "arm" sequences), it is possible that these "arm" sequences are also important in binding to Grb7.

Example 6

G7-18 Grb7-Binding Peptide Blocks Grb7-SH2 Domain Function in Cell Extracts

Two of the Grb7-binding peptides were tested for their ability to inhibit Grb7 from binding its known target molecules, such as ErbB2 and ErbB3, in whole cell extracts. Whole cell extracts were made from the cell line SKBR3, which overexpresses Grb7, ErbB2 and ErbB3. The cells were stimulated with heregulin β1 to increase the association of Grb7 with ErbB2 and ErbB3, as shown by Fiddes et.al. 1998 (Journal of Biological Chem. 273(13). p 7717). The stimulated SKBR3 cell lysate (1 mg) was incubated with the increasing amounts of synthetic G7-18NATE peptide or no peptide (control) for 1 hr at 4° C. then immunoprecipitated with anti-Grb7 (N-20, Santa Cruz #sc-607) overnight at 4° C. The immunocomplexes were collected by incubation with Protein-A sepharose beads (Zymed) for an hour at 4° C. The immunocomplexes were then collected by centrifugation and washed five times in cold lysis buffer and subjected to Western Blot analysis with anti-phosphotyrosine-HRP (Trans. Labs #610023). The immunoprecipitations were carried out with anti-Grb7 followed by western blot. The western blot was divided so the top half was incubated with anti-phosphotyrosine to detect the associated ErbB family that migrates at 185 kDa. The bottom half of western blot was incubated with anti-Grb7 as a loading control. (B) Densitometric analysis of autoradiographs using the Biorad Fluor-S Multimager with Quantity One 4.2.1 software shows G7-18NATE inhibits the association of Grb7, not Grb2, with the ErbB family in a dose-dependent manner.

Figure 6A:
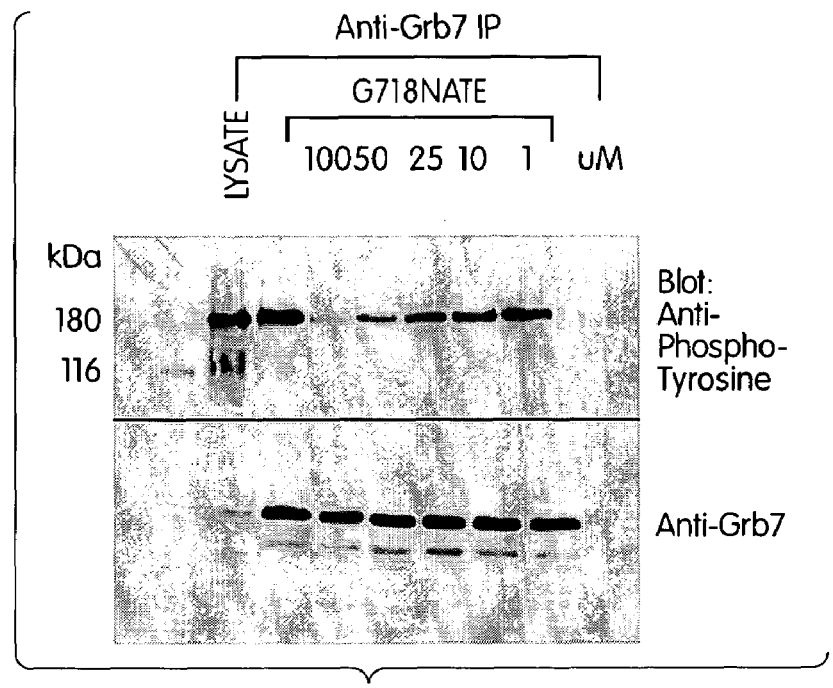
FIG. 6A is a graph showing G7-18NATE inhibits the association of Grb7 with the ErbB family of receptors, as detected by anti-phosphotyrosine.

Addition of G7-18NATE to lysates of Heregulin β-stimulated SKBR3 cells inhibits the immunoprecipitation of complexes between Grb7 and the ErbB family of tyrosine kinase receptors. FIG. 6A shows that in the presence of G7-18NATE there is a loss of binding between Grb7 and the co-precipitated tyrosine phosphorylated ErbB family, as detected by anti-phosphotyrosine at 185 kDa. FIG. 6A also demonstrates that all reactions had an equal amount of Grb7 present, as detected by anti-Grb7 (Santa Cruz #sc-607). Therefore, the loss of binding between Grb7 and the ErbB family in the presence of G7-18NATE is not because there is a lack Grb7 protein available or a difference in the amount of immunoprecipitant loaded. As a negative control immunoprecipitations were carried out in the presence of a non-phosphorylated peptide that mimics the site Grb7 binds to ErbB2 (Y1139, PQPEYVNQPD, SEQ ID NO:46), used in the Janes et al. study, side-by-side with G7-18NATE. The Y 139 non-phosphorylated ErbB2 peptide showed no competition for Grb7 binding to the ErbB family. However, this Y1139 peptide does compete when it is phosphorylated (data not shown). This demonstrated that the non-phosphorylated peptide is more effective than the natural Grb7 binding site on ErbB2 when it is not phosphorylated.

Figure 6B:
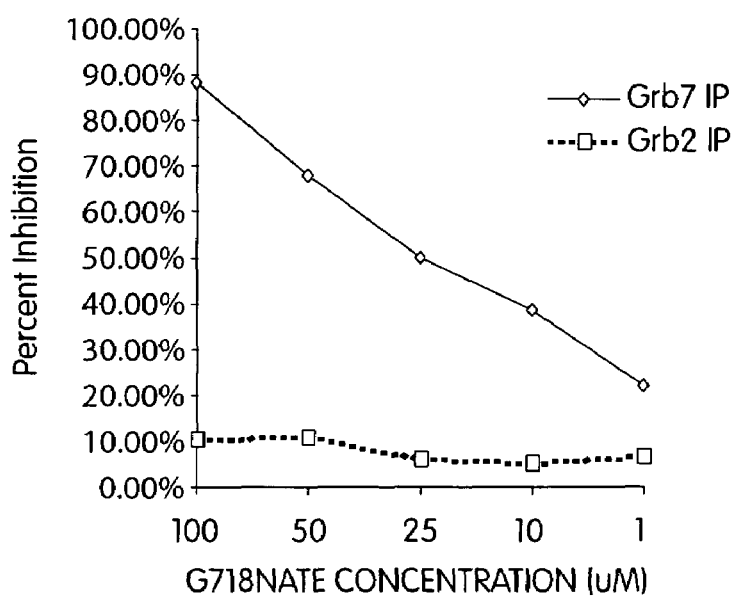
FIG. 6B is a densitometric analysis of autoradiographs using the Biorad Fluor-S Multimager with Quantity One 4.2.1 software, showing G7-18NATE inhibits the association of Grb7, not Grb2, with the ErbB family in a dose-dependent manner.

Densitometric analysis of the autoradiographs was performed using Biorad Fluor-S Multimager with Quantity One 4.2.1 software to further show that G7-18NATE is able to effectively inhibit Grb7 binding to the ErbB family in a dose-dependent manner, shown in FIG. 6B. This analysis includes monitoring Grb2 association with the ErbB family in the presence of G7-18NATE to test the specificity of G7-18NATE binding. Shown in densitometric analysis in FIG. 6B, the presence of 1-100 uM G7-18NATE has a negligible effect on the association of Grb2, compared to Grb7, co-precipitating with the tyrosine phosphorylated ErbB family, as detected by anti-phosphotyrosine at 185 kDa.

Interestingly, G7-18NATE is able to inhibit the association of Grb7 with the ErbB family even though this peptide was not as effective in the competition ELISA described above. The same levels of inhibition in co-immunoprecipitation experiments of Grb7 with the ErbB family were observed in the presence of G7-18NATE (thioether) and G7-18 (disulfide) at 100 uM (data not shown). G7-18 peptides made cyclic through the use of different covalent bonds (e.g., bonds between homocysteines) are predicted to inhibit these Grb7 interactions as well.

To further demonstrate the effect of G7-18NATE on the binding of Grb7 and the ErbB family, co-immunoprecipitation experiments were carried out between Grb7 and ErbB2 and ErbB3 specifically. The method to detect the association of Grb7 and ErbB3 is the same as described above, except that the western blots were carried out with anti-ErbB3 (Santa Cruz # sc-285). The top half of the western blot was incubated with anti-ErbB3, and the bottom half was incubated with anti-Grb7 as a loading control. Densitometric analysis of autoradiographs using the Biorad Fluor-S Multimager with Quantity One 4.2.1 software shows G7-18NATE inhibits the association of Grb7 with ErbB3 in a dose-dependent manner.

The immunoprecipitation experiments detecting the association of Grb7 and ErbB2 were carried out with purified Grb7-SH2 as a GST fusion protein immobilized onto Glutathione sepharose beads followed by a western blot analysis, following the methodology described by Janes et al. (J. of Biological Chem. 272 (13): 8490, 1997.) This method was required to detect the association of Grb7 and ErbB2 at levels at which peptide competition can be tested. The top half of the western blot was incubated with anti-ErbB2, and the bottom half was incubated with anti-Grb7 as a loading control. Densitometric analysis of autoradiographs using the Biorad Fluor-S Multimager with Quantity One 4.2.1 software shows G7-18NATE inhibits the association of Grb7 with ErbB2.

Figure 7A:
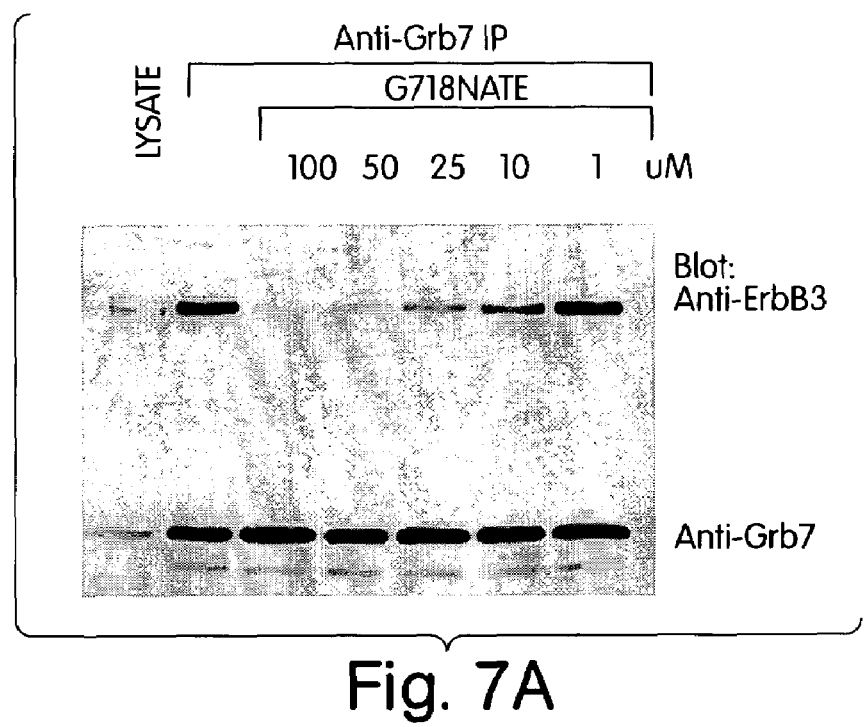
FIG. 7A is a graph showing that G7-18NATE inhibits the association of Grb7 with ErbB3 specifically in a dose-dependent manner, as detected by anti-ErbB3
Figure 7B:
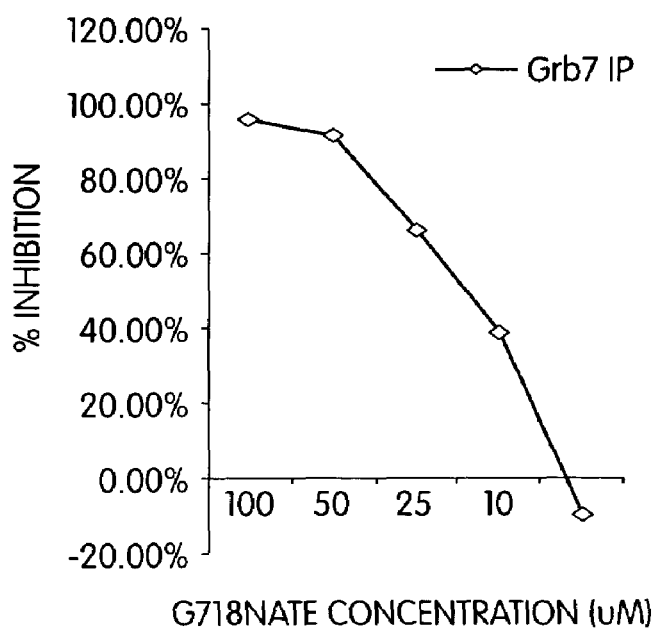
FIG. 7B is a densitometric analysis of autoradiographs using the Biorad Fluor-S Multimager with Quantity One 4.2.1 software showing that G7-18NATE inhibits the association of Grb7 with ErbB3 in a dose-dependent manner.
Figure 8A:
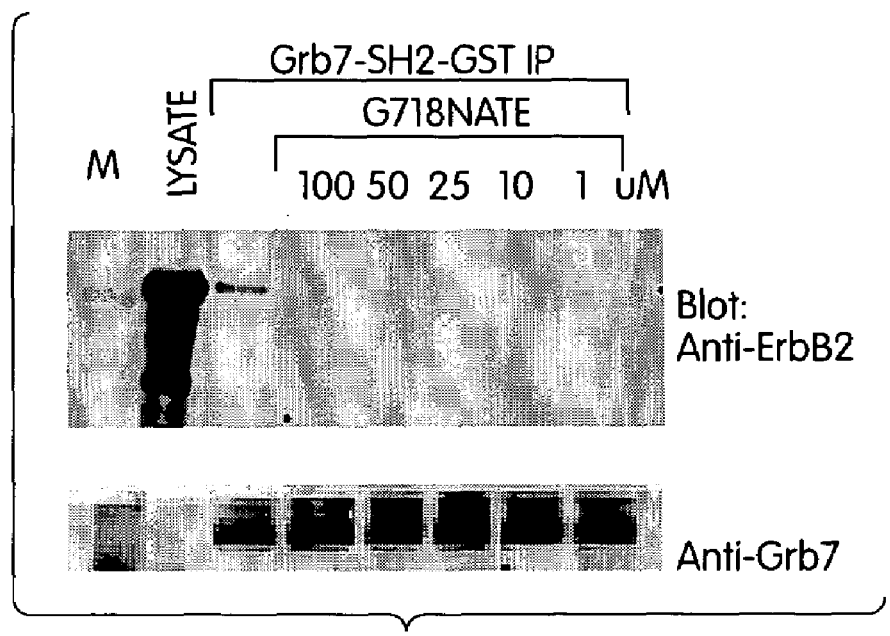
FIG. 8A is a graph showing that G7-18NATE inhibits the association of Grb7 with ErbB2 specifically in a dose-dependent manner, as detected by anti-ErbB2.
Figure 8B:
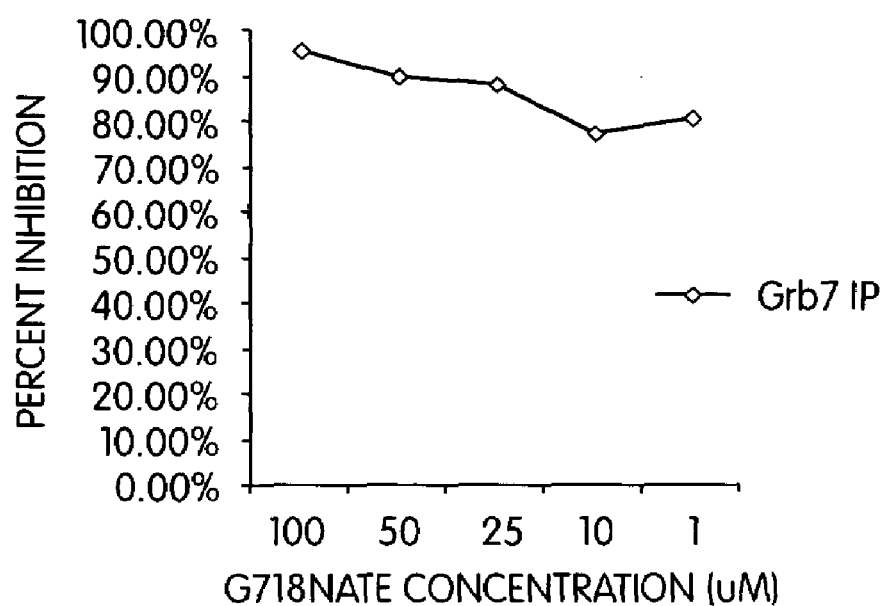
FIG. 8B is a densitometric analysis of autoradiographs using the Biorad Fluor-S Multimager with Quantity One 4.2.1 software showing that G7-18NATE inhibits the association of Grb7 with ErbB2 in a dose-dependent manner.
Figure 9A:
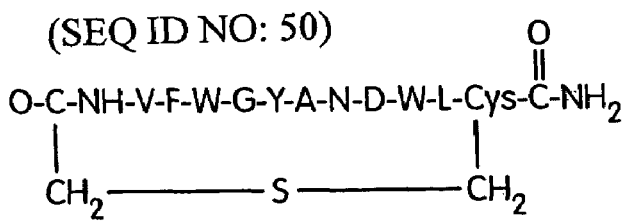
FIG. 9A is one possible chemical structure for G7BP-4NATE (SEQ ID NO:50). Other thioether linkages are illustrated in FIGS. 9B, 9C, 9D and 9E, and it is to be understood that any of these linkages can be used in the formation of G7BP-4NATE.
Figure 9B:
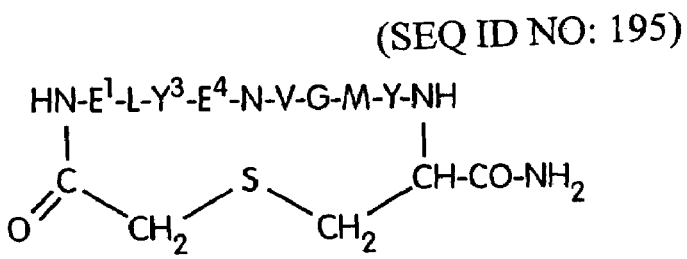
FIG. 9B is the structure of a thioether containing peptide (G1TE) (SEQ ID NO:195). This structure illustrates one possible thioether linkage between the N and C terminals of a peptide that can be used in the thioether containing peptides of the invention.
Figure 9C:
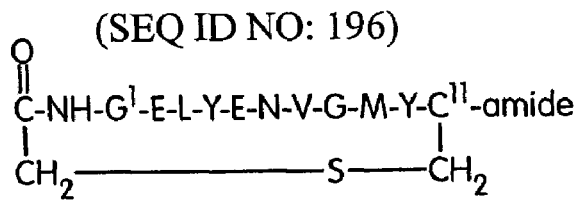
FIG. 9C is another possible structure for the thioether containing peptide G1TE (SEQ ID NO:196). This structure illustrates one possible thioether linkage between the N and C terminals of a peptide that can be used in the thioether containing peptides of the invention.
Figure 9D:
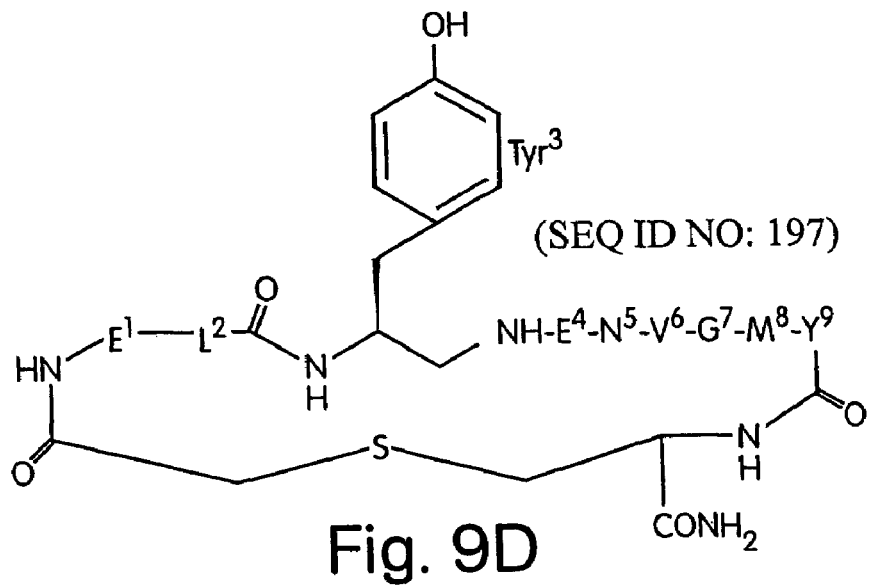
FIG. 9D is another possible structure for the thioether containing peptide G1TE (SEQ ID NO:197). This structure illustrates one possible thioether linkage between the N and C terminals of a peptide that can be used in the thioether containing peptides of the invention.
Figure 9E:
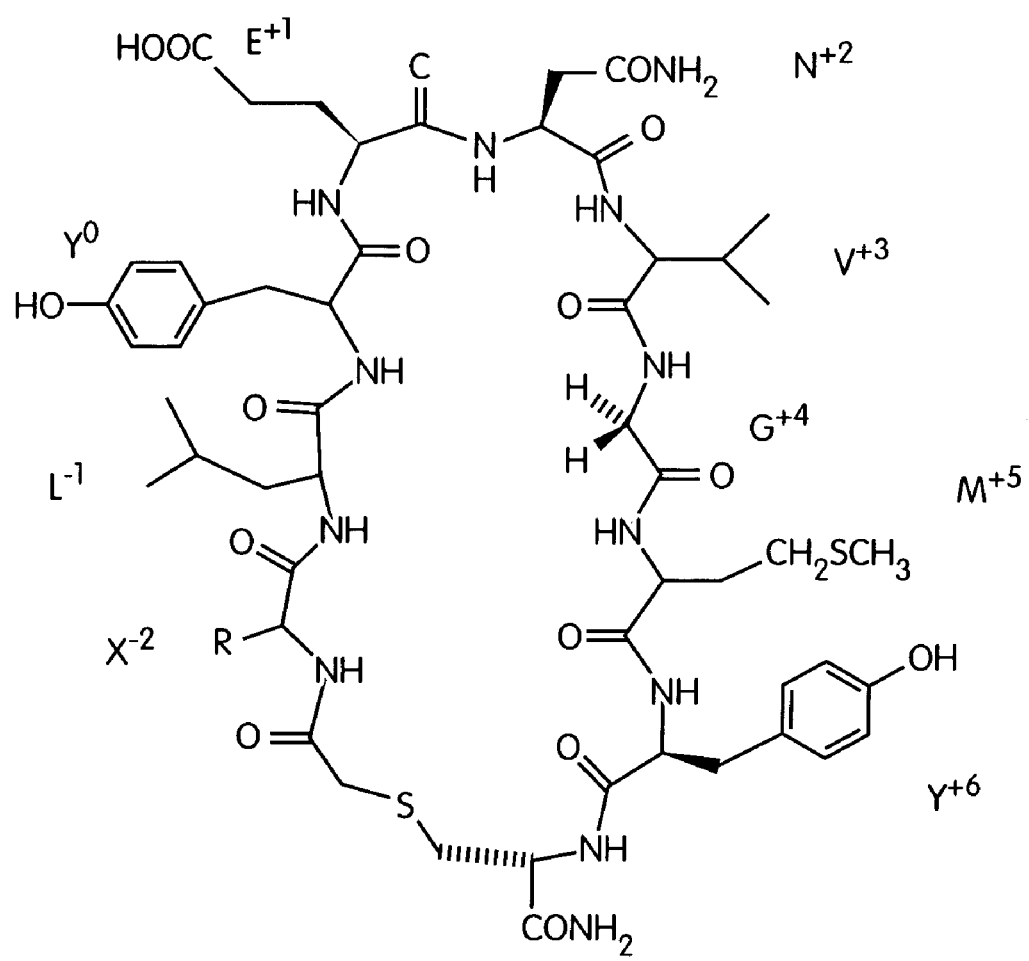
FIG. 9E is another possible structure for the thioether containing peptide G1TE. This structure illustrates one possible thioether linkage between the N and C terminals of a peptide that can be used in the thioether containing peptides of the invention.

G7-18NATE is able to inhibit the specific association of Grb7 binding to ErbB3 and ErbB2, as shown in FIGS. 7 and 8, respectively. This series of experiments, supported by the densitometric scans shown in FIGS. 7B and 8B, demonstrate that the association of Grb7 with ErbB family of receptors, specifically ErbB2 and ErbB3, can be inhibited by the small non-phosphorylated peptide G7-18NATE.

Peptides that inhibit these Grb7-ErbB family interactions less efficiently are being further analyzed to determine whether the lack of inhibition is because (1) the peptide is not stable under lysate conditions, (2) the peptide does not bind to Grb7 as strongly as G7-18NATE peptide, or (3) the peptide contains a thioether bond. Peptide binding competition assays indicate that peptide and peptide-phages of differing sequence can cross compete, suggesting the peptides and peptide-phages bind to the same site. It is likely that either stability or the thioether bond may limit the level of inhibition observed in this assay.

Example 6

Screening of Peptide Phase Library

Based on the sequences of the G7BP disclosed herein, other Grb7-binding peptides are designed using additional biased libraries which are enriched with the conserved amino acids. This is done to increase the affinity or specificity of the peptides disclosed herein. The amino acid sequences of G7BP-1 through to G7BP-7 are shown below, highlighting similar or isostructurally similar amino acids, along with the consensus sequence of the 7 peptides.

```
                                                 (SEQ ID NO:1)
G7BP-1      R V Q E C K Y L Y Y D N D Y L C K D D G (SEQ ID NO:2)
G7BP-2      K L F W C T Y E D Y A N E W P C P G Y S (SEQ ID NO:3)
G7BP-3      N V S E C I Y I H Y D N W S L C G V E V (SEQ ID NO:4)
G7BP-4      G V S N C V F W G Y A N D W L C S D Y S (SEQ ID NO:5)
G7BP-5      R S T L C W F E G Y D N T F P C K Y F R (SEQ ID NO:6)
G7BP-6      F C A V C N E E L Y E N C G G C S V G K (SEQ ID NO:7)
G7BP-7      R T S P C G Y I G Y D N I F E C T Y L G (SEQ ID NO:54)
Consensus   R V S - C - Y E G Y D N - - L C S - - -
```

Isostructural Amino Acids:
C = S = T; V = L; D = E; R = K
underline = fixed in library design
YXN, where X was enriched for D, E, A These conserved amino acids are enriched in important libraries. For example, one library design is the following:

Position 1: 50% Arginine, 20% Lysine, and 30% Random

Position 2: 70% Leucine or Valine and 30% Cysteine, Serine or Threonine

Position 3: 50% Serine, 20% Threonine, 30% Random

Position 4: 20% Glutamic Acid, 20% Leucine or Valine and 60% Random

Position 5: 100% cysteine

Position 6: 100% Random

Position 7: 70% Tyrosine, 20% Phenylalanine

This type of design biases the library for the conserved amino acids but still allow for the possibility of other amino acids to be at those positions.

Example 7

Structural Analysis of the Peptides

Gaining more structural information about the Grb7 peptides allows for further modification in order to achieve an increase in affinity or specificity of the inhibitor peptides of the invention. A study done by Janes et al. (Janes et al 1997, J Biol Chem 272: 8490-8497) reported that there are two amino acid residues within the Grb7 protein (βD5 and βD6) that are important in binding tyrosine-phosphorylated peptides. These residues were mutated in a Grb7 expressing construct and this mutant has been overexpressed, purified, and used in a screening assay of the Grb7 binding peptides of the invention. The Grb7 binding peptide-phage clones were tested for their ability to bind to a mutated form of the SH2-domain of Grb7. This mutated SH2 domain of Grb7 contains mutations in residues 480 (βD5) and 481 (βD6). To test the ability of the G7BPs to bind to mutant and wild-type Grb7-SH2 domains, the seven individual clones were tested in an ELISA with the Grb7-SH2-GST construct with mutations at βD5 and βD6, denoted as Grb7-SH2-(BD5/BD6)-GST. The results shown in FIG. 4 indicate that the Grb7 binding peptides were unable to bind to the mutant form of the Grb7-SH2 domain. This suggests that these peptides mimic the ErbB2 binding site of Grb7.

In addition, a more thorough investigation of the structure of these peptides is initiated. Structural analysis via NMR and crystallization of the SH2 domain of Grb7 are both conducted. In one set of experiments, the Grb7-binding peptides are used to obtain crystals, since having a ligand present with a protein sometimes generally facilitates crystallization. Once the structure of Grb7-SH2 is solved, the structure of Grb7-binding peptides are optimized by analysis of the binding site of the peptides on Grb7. This can be done by molecular modeling and by actually soaking the peptides into these structures, thereby visualizing how these peptides interact with the Grb7 SH2 domain. Further modifications are based on this structural information with natural and possibly non-natural amino acids.

Example 8

Internalization of Peptide

The G7BPs disclosed herein can be used as, as well as to identify further, non-phosphorylated Grb7 binding peptides with at least low micromolar affinity. Such screening can be performed in vitro using binding or competition assays as described herein. Peptides with that level of affinity can be conjugated to another peptide which functions primarily to deliver the inhibitory peptide to the cell cytoplasm. Small hydrophobic agents which may be peptide in nature can be used to transport other peptides and proteins across the cell membrane. These translocation agents include but are not limited to the translocation peptides Transportan (GWTLN-SAGYLLG—SEQ ID NO:18) (Pooga et. al., *FASEB* 1998), pAntennapedia (RQIKIWFQNRRMKWKK—SEQ ID NO:19) (Pooga et. al., *Nature Biotech* 1998), MTS (AAV-LLPVLLAAPG—SEQ ID NO:20) (Rojas et al., *Nature Biotech* 1998), Cyclic Integrin-binding Peptide (GGCRGD-MFGC—SEQ ID NO:21) (Hart et al., Journal of Biological Chemistry 1994), Tat-mediated Peptide (CFITKALGI-SYGRKKRRQRRRPPQGSQTHQVSLSKQ—SEQ ID NO:22) (Fawell et. al., PNAS 1994) and the synthetic import peptide carrier of Dokka et al. (Dokka et al., Pharm Research, 14:1759-1764, 1997. The internalization of these peptides can be monitored by adding a fluorescent or radioactive label to the peptides, followed by confocal microscopy or autoradiography.

Example 9

Biological Effects of Peptides

Once the peptides enter the cell, the phenotypic properties of cancer cells are compared between cells having and cells lacking the peptides. The ability of these peptides to inhibit the formation of complexes of Grb7 and Grb7 ligands (e.g., tyrosine kinase receptor ErbB2) as well as their ability to disrupt pre-existing complexes between Grb7 with Grb7 ligands is tested. The effects on downstream signaling members, such as SOS and Shc, which have been identified in the Grb7 signal transduction pathways is analyzed. The effects of these peptides on specific members in the Grb7 signaling pathway is analyzed in tumor cells, especially those known to express or overexpress Grb7 ligands (e.g., ErbB2). Possible effects may include cell death, inhibition of the cell cycle, and inhibition of the ability of tumor cells to invade. Normal cells are studied as controls to identify any unwanted, detrimental effects on normal and essential cells of the body.

EQUIVALENTS

It should be understood that the preceding is merely a detailed description of certain preferred embodiments. It therefore should be apparent to those of ordinary skill in the art that various modifications and equivalents can be made without departing from the spirit and scope of the invention. It is intended that the invention encompass all such modifications within the scope of the appended claims.

All references, patents and patent applications and publications that are cited or referred to in this application are incorporated in their entirety herein by reference.

---

We claim:

1. A method for treating a subject having a cancer characterized by overexpression of Grb7 comprising administering to a subject in need of such treatment a compound consisting of a non-phosphorylated Grb7 binding peptide consisting of the amino acid sequence set forth as SEQ ID NO:4, 5, 35, 42, 50, or 51, in an amount effective to inhibit metastasis, wherein the binding peptide is attached to a translocation agent capable of transporting the peptide into cell cytoplasm or the nucleus of a cell, binds to the SH2 domain of Grb7 and does not specifically bind the SH2 domain of Grb2 or Grb14, and wherein the peptide is administered locally to the cancer.

2. The method of claim 1, wherein the peptide is cyclic.

3. The method of claim 1 wherein the cancer is a metastasis.

4. The method of claim 1, wherein the Grb7 binding peptide is administered with a pharmaceutically acceptable carrier.

5. The method of claim 1, wherein the translocation agent has the amino acid sequence RQIKIWFQNRRMKWKK (SEQ ID NO:19).

* * * * *

SEQUENCE LISTING

```
<160> NUMBER OF SEQ ID NOS: 194
<210> SEQ ID NO 1
<211> LENGTH: 20
<212> TYPE: PRT
<213> ORGANISM: Artificial Sequence
<220> FEATURE:
<223> OTHER INFORMATION: Peptide sequence from FuseV Phage Display

<400> SEQUENCE: 1
```

-continued

Arg Val Gln Glu Cys Lys Tyr Leu Tyr Tyr Asp Asn Asp Tyr Leu Cys
1               5                   10                  15

Lys Asp Asp Gly
            20

<210> SEQ ID NO 2
<211> LENGTH: 20
<212> TYPE: PRT
<213> ORGANISM: Artificial Sequence
<220> FEATURE:
<223> OTHER INFORMATION: Peptide sequence from FuseV Phage Display

<400> SEQUENCE: 2

Lys Leu Phe Trp Cys Thr Tyr Glu Asp Tyr Ala Asn Glu Trp Pro Cys
1               5                   10                  15

Pro Gly Tyr Ser
            20

<210> SEQ ID NO 3
<211> LENGTH: 20
<212> TYPE: PRT
<213> ORGANISM: Artificial Sequence
<220> FEATURE:
<223> OTHER INFORMATION: Peptide sequence from FuseV Phage Display

<400> SEQUENCE: 3

Asn Val Ser Glu Cys Ile Tyr Ile His Tyr Asp Asn Trp Ser Leu Cys
1               5                   10                  15

Gly Val Glu Val
            20

<210> SEQ ID NO 4
<211> LENGTH: 20
<212> TYPE: PRT
<213> ORGANISM: Artificial Sequence
<220> FEATURE:
<223> OTHER INFORMATION: Peptide sequence from FuseV Phage Display

<400> SEQUENCE: 4

Gly Val Ser Asn Cys Val Phe Trp Gly Tyr Ala Asn Asp Trp Leu Cys
1               5                   10                  15

Ser Asp Tyr Ser
            20

<210> SEQ ID NO 5
<211> LENGTH: 20
<212> TYPE: PRT
<213> ORGANISM: Artificial Sequence
<220> FEATURE:
<223> OTHER INFORMATION: Peptide sequence from FuseV Phage Display

<400> SEQUENCE: 5

Arg Ser Thr Leu Cys Trp Phe Glu Gly Tyr Asp Asn Thr Phe Pro Cys
1               5                   10                  15

Lys Tyr Phe Arg
            20

<210> SEQ ID NO 6
<211> LENGTH: 20
<212> TYPE: PRT
<213> ORGANISM: Artificial Sequence
<220> FEATURE:
<223> OTHER INFORMATION: Peptide sequence from FuseV Phage Display

<400> SEQUENCE: 6

-continued

Phe Cys Ala Val Cys Asn Glu Glu Leu Tyr Glu Asn Cys Gly Gly Cys
1               5                   10                  15

Ser Val Gly Lys
            20

<210> SEQ ID NO 7
<211> LENGTH: 20
<212> TYPE: PRT
<213> ORGANISM: Artificial Sequence
<220> FEATURE:
<223> OTHER INFORMATION: Peptide sequence from FuseV Phage Display

<400> SEQUENCE: 7

Arg Thr Ser Pro Cys Gly Tyr Ile Gly Tyr Asp Asn Ile Phe Glu Cys
1               5                   10                  15

Thr Tyr Leu Gly
            20

<210> SEQ ID NO 8
<211> LENGTH: 3
<212> TYPE: PRT
<213> ORGANISM: Artificial Sequence
<220> FEATURE:
<223> OTHER INFORMATION: Consensus Sequence

<400> SEQUENCE: 8

Tyr Ala Asn
1

<210> SEQ ID NO 9
<211> LENGTH: 3
<212> TYPE: PRT
<213> ORGANISM: Artificial Sequence
<220> FEATURE:
<223> OTHER INFORMATION: Consensus Sequence

<400> SEQUENCE: 9

Tyr Glu Asn
1

<210> SEQ ID NO 10
<211> LENGTH: 3
<212> TYPE: PRT
<213> ORGANISM: Artificial Sequence
<220> FEATURE:
<223> OTHER INFORMATION: Consensus Sequence

<400> SEQUENCE: 10

Tyr Asp Asn
1

<210> SEQ ID NO 11
<211> LENGTH: 60
<212> TYPE: RNA
<213> ORGANISM: Artificial Sequence
<220> FEATURE:
<223> OTHER INFORMATION: Nucleic Acid of G7BP-1

<400> SEQUENCE: 11
cguguucaag aauguaaaua uuuauauuau gauaaugaua uauuauguaa agaugauggu     60

<210> SEQ ID NO 12
<211> LENGTH: 60
<212> TYPE: RNA
<213> ORGANISM: Artificial Sequence

```
<220> FEATURE:
<223> OTHER INFORMATION: Nucleic Acid of G7BP-2

<400> SEQUENCE: 12
aaauuauuuu gguguacuua ugaagauuau gcaaaugaau ggccuuguc  ugguuauucu       60

<210> SEQ ID NO 13
<211> LENGTH: 60
<212> TYPE: RNA
<213> ORGANISM: Artificial Sequence
<220> FEATURE:
<223> OTHER INFORMATION: Nucleic Acid Sequence of G7BP-3

<400> SEQUENCE: 13
aauguuucug aauguauuua uauucauuau gauaauuggu cuuuaugugg uguugaaguu       60

<210> SEQ ID NO 14
<211> LENGTH: 60
<212> TYPE: RNA
<213> ORGANISM: Artificial Sequence
<220> FEATURE:
<223> OTHER INFORMATION: Nucleic Acid Sequence of G7BP-4

<400> SEQUENCE: 14
gguguuucua auuguguuuu uuggguuau gcaaaugauu gguuauguuc ugauuauucu       60

<210> SEQ ID NO 15
<211> LENGTH: 60
<212> TYPE: RNA
<213> ORGANISM: Artificial Sequence
<220> FEATURE:
<223> OTHER INFORMATION: Nucleic Acid Sequence of G7BP-5

<400> SEQUENCE: 15
cguucuacuu uauguuggu ugaagguuau gauaauacuu uccuuguaa auauuuucgu       60

<210> SEQ ID NO 16
<211> LENGTH: 60
<212> TYPE: RNA
<213> ORGANISM: Artificial Sequence
<220> FEATURE:
<223> OTHER INFORMATION: Nucleic Acid Sequence of G7BP-6

<400> SEQUENCE: 16
uuuugugcag uuuguaauga agaauuauau gaaaauugug gugguuguuc uguugguaaa       60

<210> SEQ ID NO 17
<211> LENGTH: 60
<212> TYPE: RNA
<213> ORGANISM: Artificial Sequence
<220> FEATURE:
<223> OTHER INFORMATION: Nucleic Acid Molecule of G7BP-7

<400> SEQUENCE: 17
cguacuucuc cuuguggau aauugguuau gauaauauuu uugaauguac uuauuuaggu       60

<210> SEQ ID NO 18
<211> LENGTH: 12
<212> TYPE: PRT
<213> ORGANISM: Artificial Sequence
<220> FEATURE:
<223> OTHER INFORMATION: Translocation Agent

<400> SEQUENCE: 18

Gly Trp Thr Leu Asn Ser Ala Gly Tyr Leu Leu Gly
1               5                   10
```

```
<210> SEQ ID NO 19
<211> LENGTH: 16
<212> TYPE: PRT
<213> ORGANISM: Artificial Sequence
<220> FEATURE:
<223> OTHER INFORMATION: Translocation Agent

<400> SEQUENCE: 19

Arg Gln Ile Lys Ile Trp Phe Gln Asn Arg Arg Met Lys Trp Lys Lys
1               5                   10                  15

<210> SEQ ID NO 20
<211> LENGTH: 13
<212> TYPE: PRT
<213> ORGANISM: Artificial Sequence
<220> FEATURE:
<223> OTHER INFORMATION: Translocation Agent

<400> SEQUENCE: 20

Ala Ala Val Leu Leu Pro Val Leu Leu Ala Ala Pro Gly
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Translocation Agent

<400> SEQUENCE: 21

Gly Gly Cys Arg Gly Asp Met Phe Gly Cys
1               5                   10

<210> SEQ ID NO 22
<211> LENGTH: 36
<212> TYPE: PRT
<213> ORGANISM: Artificial Sequence
<220> FEATURE:
<223> OTHER INFORMATION: Translocation Agent

<400> SEQUENCE: 22

Cys Phe Ile Thr Lys Ala Leu Gly Ile Ser Tyr Gly Arg Lys Lys Arg
1               5                   10                  15

Arg Gln Arg Arg Arg Pro Pro Gln Gly Ser Gln Thr His Gln Val Ser
            20                  25                  30

Leu Ser Lys Gln
        35

<210> SEQ ID NO 23
<211> LENGTH: 11
<212> TYPE: PRT
<213> ORGANISM: Artificial Sequence
<220> FEATURE:
<223> OTHER INFORMATION: Amino Acid Sequence of a Grb7 antagonist
<221> NAME/KEY: MISC_FEATURE
<222> LOCATION: (2)..(4)
<223> OTHER INFORMATION: Xaa = any amino acid
<221> NAME/KEY: MISC_FEATURE
<222> LOCATION: (8)..(10)
<223> OTHER INFORMATION: Xaa = any amino acid

<400> SEQUENCE: 23

Cys Xaa Xaa Xaa Tyr Ala Asn Xaa Xaa Xaa Cys
1               5                   10
```

```
<210> SEQ ID NO 24
<211> LENGTH: 11
<212> TYPE: PRT
<213> ORGANISM: Artificial Sequence
<220> FEATURE:
<223> OTHER INFORMATION: Amino Acid Sequence of a Grb7 antagonist
<221> NAME/KEY: MISC_FEATURE
<222> LOCATION: (2)..(4)
<223> OTHER INFORMATION: Xaa = any amino acid
<221> NAME/KEY: MISC_FEATURE
<222> LOCATION: (8)..(10)
<223> OTHER INFORMATION: Xaa = any amino acid

<400> SEQUENCE: 24

Cys Xaa Xaa Xaa Tyr Asp Asn Xaa Xaa Xaa Cys
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Amino Acid Sequence of a Grb7 antagonist
<221> NAME/KEY: MISC_FEATURE
<222> LOCATION: (2)..(4)
<223> OTHER INFORMATION: Xaa = any amino acid
<221> NAME/KEY: MISC_FEATURE
<222> LOCATION: (8)..(10)
<223> OTHER INFORMATION: Xaa = any amino acid

<400> SEQUENCE: 25

Cys Xaa Xaa Xaa Tyr Glu Asn Xaa Xaa Xaa Cys
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Amino Acid Sequence of a Grb7 antagonist
<221> NAME/KEY: MISC_FEATURE
<222> LOCATION: (2)..(5)
<223> OTHER INFORMATION: Xaa = any amino acid
<221> NAME/KEY: MISC_FEATURE
<222> LOCATION: (9)..(11)
<223> OTHER INFORMATION: Xaa = any amino acid

<400> SEQUENCE: 26

Cys Xaa Xaa Xaa Xaa Tyr Ala Asn Xaa Xaa Xaa Cys
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Amino Acid Sequence of a Grb7 antagonist
<221> NAME/KEY: MISC_FEATURE
<222> LOCATION: (2)..(5)
<223> OTHER INFORMATION: Xaa = any amino acid
<221> NAME/KEY: MISC_FEATURE
<222> LOCATION: (9)..(11)
<223> OTHER INFORMATION: Xaa = any amino acid

<400> SEQUENCE: 27

Cys Xaa Xaa Xaa Xaa Tyr Asp Asn Xaa Xaa Xaa Cys
1               5                   10

<210> SEQ ID NO 28
<211> LENGTH: 12
<212> TYPE: PRT
```

-continued

```
<213> ORGANISM: Artificial Sequence
<220> FEATURE:
<223> OTHER INFORMATION: Amino Acid Sequence of a Grb7 antagonist
<221> NAME/KEY: MISC_FEATURE
<222> LOCATION: (2)..(5)
<223> OTHER INFORMATION: Xaa = any amino acid
<221> NAME/KEY: MISC_FEATURE
<222> LOCATION: (9)..(11)
<223> OTHER INFORMATION: Xaa = any amino acid

<400> SEQUENCE: 28

Cys Xaa Xaa Xaa Xaa Tyr Glu Asn Xaa Xaa Xaa Cys
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Amino Acid Sequence of a Grb7 antagonist
<221> NAME/KEY: MISC_FEATURE
<222> LOCATION: (2)..(4)
<223> OTHER INFORMATION: Xaa = any amino acid
<221> NAME/KEY: MISC_FEATURE
<222> LOCATION: (8)..(11)
<223> OTHER INFORMATION: Xaa = any amino acid

<400> SEQUENCE: 29

Cys Xaa Xaa Xaa Tyr Ala Asn Xaa Xaa Xaa Xaa Cys
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Amino Acid Sequence of a Grb7 antagonist
<221> NAME/KEY: MISC_FEATURE
<222> LOCATION: (2)..(4)
<223> OTHER INFORMATION: Xaa = any amino acid
<221> NAME/KEY: MISC_FEATURE
<222> LOCATION: (8)..(11)
<223> OTHER INFORMATION: Xaa = any amino acid

<400> SEQUENCE: 30

Cys Xaa Xaa Xaa Tyr Asp Asn Xaa Xaa Xaa Xaa Cys
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Amino Acid Sequence of a Grb7 antagonist
<221> NAME/KEY: MISC_FEATURE
<222> LOCATION: (2)..(4)
<223> OTHER INFORMATION: Xaa = any amino acid
<221> NAME/KEY: MISC_FEATURE
<222> LOCATION: (8)..(11)
<223> OTHER INFORMATION: Xaa = any amino acid

<400> SEQUENCE: 31

Cys Xaa Xaa Xaa Tyr Glu Asn Xaa Xaa Xaa Xaa Cys
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Non-phosphorylated peptide with YEN motif
```

```
<400> SEQUENCE: 32

Cys Glu Leu Tyr Glu Asn Val Gly Met Tyr Cys
1               5                   10

<210> SEQ ID NO 33
<211> LENGTH: 20
<212> TYPE: PRT
<213> ORGANISM: Artificial Sequence
<220> FEATURE:
<223> OTHER INFORMATION: General Formula
<221> NAME/KEY: MISC_FEATURE
<222> LOCATION: (1)..(4)
<223> OTHER INFORMATION: Xaa = any amino acid
<221> NAME/KEY: MISC_FEATURE
<222> LOCATION: (6)..(9)
<223> OTHER INFORMATION: Xaa = any amino acid
<221> NAME/KEY: MISC_FEATURE
<222> LOCATION: (11)..(11)
<223> OTHER INFORMATION: Xaa = any amino acid
<221> NAME/KEY: MISC_FEATURE
<222> LOCATION: (13)..(15)
<223> OTHER INFORMATION: Xaa = any amino acid
<221> NAME/KEY: MISC_FEATURE
<222> LOCATION: (17)..(20)
<223> OTHER INFORMATION: Xaa = any amino acid

<400> SEQUENCE: 33

Xaa Xaa Xaa Xaa Cys Xaa Xaa Xaa Xaa Tyr Xaa Asn Xaa Xaa Xaa Cys
1               5                   10                  15

Xaa Xaa Xaa Xaa
            20

<210> SEQ ID NO 34
<211> LENGTH: 5
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (3)..(3)
<223> OTHER INFORMATION: Xaa = any amino acid

<400> SEQUENCE: 34

Cys Tyr Xaa Asn Cys
1               5

<210> SEQ ID NO 35
<211> LENGTH: 11
<212> TYPE: PRT
<213> ORGANISM: Artificial Sequence
<220> FEATURE:
<223> OTHER INFORMATION: Variant of G7BP-4

<400> SEQUENCE: 35

Cys Val Phe Gly Tyr Ala Asn Asp Trp Leu Cys
1               5                   10

<210> SEQ ID NO 36
<211> LENGTH: 19
<212> TYPE: PRT
<213> ORGANISM: Artificial Sequence
<220> FEATURE:
<223> OTHER INFORMATION: Variant of G7BP-4

<400> SEQUENCE: 36

Gly Val Ser Asn Ser Val Phe Gly Tyr Ala Asn Asp Trp Leu Ser Ser
1               5                   10                  15
```

Asp Tyr Ser

<210> SEQ ID NO 37
<211> LENGTH: 19
<212> TYPE: PRT
<213> ORGANISM: Artificial Sequence
<220> FEATURE:
<223> OTHER INFORMATION: Variant of G7BP-4

<400> SEQUENCE: 37

Gly Val Ser Asn Val Val Phe Gly Tyr Ala Asn Asp Trp Leu Val Ser
1               5                   10                  15

Asp Tyr Ser

<210> SEQ ID NO 38
<211> LENGTH: 11
<212> TYPE: PRT
<213> ORGANISM: Artificial Sequence
<220> FEATURE:
<223> OTHER INFORMATION: Variant of G7BP-4

<400> SEQUENCE: 38

Ser Val Phe Gly Tyr Ala Asn Asp Trp Leu Ser
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Variant of G7BP-1

<400> SEQUENCE: 39

Cys Lys Tyr Leu Tyr Tyr Asp Asn Asp Tyr Leu Cys
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Variant of G7BP-2

<400> SEQUENCE: 40

Cys Thr Tyr Glu Asp Tyr Ala Asn Glu Trp Pro Cys
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Variant of G7BP-3

<400> SEQUENCE: 41

Cys Ile Tyr Ile His Tyr Asp Asn Trp Ser Leu Cys
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Variant of G7BP-5

<400> SEQUENCE: 42

```
Cys Trp Phe Glu Gly Tyr Asp Asn Thr Phe Pro Cys
1               5                   10
```

<210> SEQ ID NO 43
<211> LENGTH: 12
<212> TYPE: PRT
<213> ORGANISM: Artificial Sequence
<220> FEATURE:
<223> OTHER INFORMATION: Variant of G7BP-6

<400> SEQUENCE: 43

```
Cys Asn Glu Glu Leu Tyr Glu Asn Cys Gly Gly Cys
1               5                   10
```

<210> SEQ ID NO 44
<211> LENGTH: 12
<212> TYPE: PRT
<213> ORGANISM: Artificial Sequence
<220> FEATURE:
<223> OTHER INFORMATION: Variant of G7BP-7

<400> SEQUENCE: 44

```
Cys Gly Tyr Ile Gly Tyr Asp Asn Ile Phe Glu Cys
1               5                   10
```

<210> SEQ ID NO 45
<211> LENGTH: 6
<212> TYPE: PRT
<213> ORGANISM: Artificial Sequence
<220> FEATURE:
<223> OTHER INFORMATION: Amino acid sequence of PI3 kinase SH2 binding
      peptide
<221> NAME/KEY: MISC_FEATURE
<222> LOCATION: (2)..(2)
<223> OTHER INFORMATION: phosphotyrosine

<400> SEQUENCE: 45

```
Asp Tyr Val Pro Met Leu
1               5
```

<210> SEQ ID NO 46
<211> LENGTH: 10
<212> TYPE: PRT
<213> ORGANISM: Artificial Sequence
<220> FEATURE:
<223> OTHER INFORMATION: Non-phosphorylated peptide which mimics ErbB2
      site

<400> SEQUENCE: 46

```
Pro Gln Pro Glu Tyr Val Asn Gln Pro Asp
1               5                   10
```

<210> SEQ ID NO 47
<211> LENGTH: 11
<212> TYPE: PRT
<213> ORGANISM: Artificial Sequence
<220> FEATURE:
<223> OTHER INFORMATION: Variant G7BP-1NATE
<221> NAME/KEY: MISC_FEATURE
<222> LOCATION: (1)..(1)
<223> OTHER INFORMATION: thioether bond between ends of peptide
<221> NAME/KEY: MISC_FEATURE
<222> LOCATION: (11)..(11)
<223> OTHER INFORMATION: thioether bond between ends of peptide

<400> SEQUENCE: 47

```
Lys Tyr Leu Tyr Tyr Asp Asn Asp Tyr Leu Cys
1               5                   10
```

```
-continued

<210> SEQ ID NO 48
<211> LENGTH: 11
<212> TYPE: PRT
<213> ORGANISM: Artificial Sequence
<220> FEATURE:
<223> OTHER INFORMATION: Variant G7BP-2NATE
<221> NAME/KEY: MISC_FEATURE
<222> LOCATION: (1)..(1)
<223> OTHER INFORMATION: thioether bond between ends of peptide
<221> NAME/KEY: MISC_FEATURE
<222> LOCATION: (11)..(11)
<223> OTHER INFORMATION: thioether bond between ends of peptide

<400> SEQUENCE: 48

Thr Tyr Glu Asp Tyr Ala Asn Glu Trp Pro Cys
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Variant G7BP-3NATE
<221> NAME/KEY: MISC_FEATURE
<222> LOCATION: (1)..(1)
<223> OTHER INFORMATION: thioether bond between ends of peptide
<221> NAME/KEY: MISC_FEATURE
<222> LOCATION: (11)..(11)
<223> OTHER INFORMATION: thioether bond between ends of peptide

<400> SEQUENCE: 49

Ile Tyr Ile His Tyr Asp Asn Trp Ser Leu Cys
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Variant G7BP-4NATE
<221> NAME/KEY: MISC_FEATURE
<222> LOCATION: (1)..(1)
<223> OTHER INFORMATION: thioether bond between ends of peptide
<221> NAME/KEY: MISC_FEATURE
<222> LOCATION: (11)..(11)
<223> OTHER INFORMATION: thioether bond between ends of peptide

<400> SEQUENCE: 50

Val Phe Trp Gly Tyr Ala Asn Asp Trp Leu Cys
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Variant G7BP-5NATE
<221> NAME/KEY: MISC_FEATURE
<222> LOCATION: (1)..(1)
<223> OTHER INFORMATION: thioether bond between ends of peptide
<221> NAME/KEY: MISC_FEATURE
<222> LOCATION: (11)..(11)
<223> OTHER INFORMATION: thioether bond between ends of peptide

<400> SEQUENCE: 51

Trp Phe Glu Gly Tyr Asp Asn Thr Phe Pro Cys
1               5                   10

<210> SEQ ID NO 52
<211> LENGTH: 11
```

```
<212> TYPE: PRT
<213> ORGANISM: Artificial Sequence
<220> FEATURE:
<223> OTHER INFORMATION: Variant G7BP-6NATE
<221> NAME/KEY: MISC_FEATURE
<222> LOCATION: (1)..(1)
<223> OTHER INFORMATION: thioether bond between ends of peptide
<221> NAME/KEY: MISC_FEATURE
<222> LOCATION: (11)..(11)
<223> OTHER INFORMATION: thioether bond between ends of peptide

<400> SEQUENCE: 52

Asn Glu Glu Leu Tyr Glu Asn Cys Gly Gly Cys
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Variant G7BP-7NATE
<221> NAME/KEY: MISC_FEATURE
<222> LOCATION: (1)..(1)
<223> OTHER INFORMATION: thioether bond between ends of peptide
<221> NAME/KEY: MISC_FEATURE
<222> LOCATION: (11)..(11)
<223> OTHER INFORMATION: thioether bond between ends of peptide

<400> SEQUENCE: 53

Gly Tyr Ile Gly Tyr Asp Asn Ile Phe Glu Cys
1               5                   10

<210> SEQ ID NO 54
<211> LENGTH: 20
<212> TYPE: PRT
<213> ORGANISM: Artificial Sequence
<220> FEATURE:
<223> OTHER INFORMATION: Consensus Sequence
<221> NAME/KEY: MISC_FEATURE
<222> LOCATION: (4)..(4)
<223> OTHER INFORMATION: Xaa = any amino acid
<221> NAME/KEY: MISC_FEATURE
<222> LOCATION: (6)..(6)
<223> OTHER INFORMATION: Xaa = any amino acid
<221> NAME/KEY: MISC_FEATURE
<222> LOCATION: (13)..(14)
<223> OTHER INFORMATION: Xaa = any amino acid
<221> NAME/KEY: MISC_FEATURE
<222> LOCATION: (18)..(20)
<223> OTHER INFORMATION: Xaa = any amino acid

<400> SEQUENCE: 54

Arg Val Ser Xaa Cys Xaa Tyr Glu Gly Tyr Asp Asn Xaa Xaa Leu Cys
1               5                   10                  15

Ser Xaa Xaa Xaa
            20

<210> SEQ ID NO 55
<211> LENGTH: 4
<212> TYPE: PRT
<213> ORGANISM: Artificial Sequence
<220> FEATURE:
<223> OTHER INFORMATION: Amino acid sequences containing phosphotyrosine
      residues which bind Grb7
<221> NAME/KEY: MISC_FEATURE
<222> LOCATION: (1)..(1)
<223> OTHER INFORMATION: phosphotyrosine

<400> SEQUENCE: 55

Tyr Val Asn Val
1
```

<210> SEQ ID NO 56
<211> LENGTH: 4
<212> TYPE: PRT
<213> ORGANISM: Artificial Sequence
<220> FEATURE:
<223> OTHER INFORMATION: Amino acid sequences containing phosphotyrosine
      residues which bind Grb7
<221> NAME/KEY: MISC_FEATURE
<222> LOCATION: (1)..(1)
<223> OTHER INFORMATION: phosphotyrosine

<400> SEQUENCE: 56

Tyr Glu Asn Val
1

<210> SEQ ID NO 57
<211> LENGTH: 4
<212> TYPE: PRT
<213> ORGANISM: Artificial Sequence
<220> FEATURE:
<223> OTHER INFORMATION: Amino acid sequences containing phosphotyrosine
      residues which bind Grb7
<221> NAME/KEY: MISC_FEATURE
<222> LOCATION: (1)..(1)
<223> OTHER INFORMATION: phosphotyrosine

<400> SEQUENCE: 57

Tyr Val Asn Gln
1

<210> SEQ ID NO 58
<211> LENGTH: 4
<212> TYPE: PRT
<213> ORGANISM: Artificial Sequence
<220> FEATURE:
<223> OTHER INFORMATION: Amino acid sequences containing phosphotyrosine
      residues which bind Grb7
<221> NAME/KEY: MISC_FEATURE
<222> LOCATION: (1)..(1)
<223> OTHER INFORMATION: phosphotyrosine

<400> SEQUENCE: 58

Tyr Ser Asn Leu
1

<210> SEQ ID NO 59
<211> LENGTH: 4
<212> TYPE: PRT
<213> ORGANISM: Artificial Sequence
<220> FEATURE:
<223> OTHER INFORMATION: Amino acid sequences containing phosphotyrosine
      residues which bind Grb7
<221> NAME/KEY: MISC_FEATURE
<222> LOCATION: (1)..(1)
<223> OTHER INFORMATION: phosphotyrosine

<400> SEQUENCE: 59

Tyr Ala Glu Ile
1

<210> SEQ ID NO 60
<211> LENGTH: 6
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (3)..(3)
<223> OTHER INFORMATION: Xaa = any amino acid

```
<221> NAME/KEY: MISC_FEATURE
<222> LOCATION: (5)..(5)
<223> OTHER INFORMATION: Xaa = any amino acid

<400> SEQUENCE: 60

Cys Tyr Xaa Asn Xaa Cys
1               5

<210> SEQ ID NO 61
<211> LENGTH: 6
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(2)
<223> OTHER INFORMATION: Xaa = any amino acid
<221> NAME/KEY: MISC_FEATURE
<222> LOCATION: (4)..(4)
<223> OTHER INFORMATION: Xaa = any amino acid

<400> SEQUENCE: 61

Cys Xaa Tyr Xaa Asn Cys
1               5

<210> SEQ ID NO 62
<211> LENGTH: 7
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (3)..(3)
<223> OTHER INFORMATION: Xaa = any amino acid
<221> NAME/KEY: MISC_FEATURE
<222> LOCATION: (5)..(6)
<223> OTHER INFORMATION: Xaa = any amino acid

<400> SEQUENCE: 62

Cys Tyr Xaa Asn Xaa Xaa Cys
1               5

<210> SEQ ID NO 63
<211> LENGTH: 7
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(2)
<223> OTHER INFORMATION: Xaa = any amino acid
<221> NAME/KEY: MISC_FEATURE
<222> LOCATION: (4)..(4)
<223> OTHER INFORMATION: Xaa = any amino acid
<221> NAME/KEY: MISC_FEATURE
<222> LOCATION: (6)..(6)
<223> OTHER INFORMATION: Xaa = any amino acid

<400> SEQUENCE: 63

Cys Xaa Tyr Xaa Asn Xaa Cys
1               5

<210> SEQ ID NO 64
<211> LENGTH: 7
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(3)
<223> OTHER INFORMATION: Xaa = any amino acid
```

```
<221> NAME/KEY: MISC_FEATURE
<222> LOCATION: (5)..(5)
<223> OTHER INFORMATION: Xaa = any amino acid

<400> SEQUENCE: 64

Cys Xaa Xaa Tyr Xaa Asn Cys
1               5

<210> SEQ ID NO 65
<211> LENGTH: 8
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (3)..(3)
<223> OTHER INFORMATION: Xaa = any amino acid
<221> NAME/KEY: MISC_FEATURE
<222> LOCATION: (5)..(7)
<223> OTHER INFORMATION: Xaa = any amino acid

<400> SEQUENCE: 65

Cys Tyr Xaa Asn Xaa Xaa Xaa Cys
1               5

<210> SEQ ID NO 66
<211> LENGTH: 8
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(2)
<223> OTHER INFORMATION: Xaa = any amino acid
<221> NAME/KEY: MISC_FEATURE
<222> LOCATION: (4)..(4)
<223> OTHER INFORMATION: Xaa = any amino acid
<221> NAME/KEY: MISC_FEATURE
<222> LOCATION: (6)..(7)
<223> OTHER INFORMATION: Xaa = any amino acid

<400> SEQUENCE: 66

Cys Xaa Tyr Xaa Asn Xaa Xaa Cys
1               5

<210> SEQ ID NO 67
<211> LENGTH: 8
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(3)
<223> OTHER INFORMATION: Xaa = any amino acid
<221> NAME/KEY: MISC_FEATURE
<222> LOCATION: (5)..(5)
<223> OTHER INFORMATION: Xaa = any amino acid
<221> NAME/KEY: MISC_FEATURE
<222> LOCATION: (7)..(7)
<223> OTHER INFORMATION: Xaa = any amino acid

<400> SEQUENCE: 67

Cys Xaa Xaa Tyr Xaa Asn Xaa Cys
1               5

<210> SEQ ID NO 68
<211> LENGTH: 8
<212> TYPE: PRT
<213> ORGANISM: Artificial Sequence
<220> FEATURE:
<223> OTHER INFORMATION: One Embodiment of General Formula
```

```
<221> NAME/KEY: MISC_FEATURE
<222> LOCATION: (2)..(4)
<223> OTHER INFORMATION: Xaa = any amino acid
<221> NAME/KEY: MISC_FEATURE
<222> LOCATION: (6)..(6)
<223> OTHER INFORMATION: Xaa = any amino acid

<400> SEQUENCE: 68

Cys Xaa Xaa Xaa Tyr Xaa Asn Cys
1               5

<210> SEQ ID NO 69
<211> LENGTH: 9
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (3)..(3)
<223> OTHER INFORMATION: Xaa = any amino acid
<221> NAME/KEY: MISC_FEATURE
<222> LOCATION: (5)..(8)
<223> OTHER INFORMATION: Xaa = any amino acid

<400> SEQUENCE: 69

Cys Tyr Xaa Asn Xaa Xaa Xaa Xaa Cys
1               5

<210> SEQ ID NO 70
<211> LENGTH: 9
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(2)
<223> OTHER INFORMATION: Xaa = any amino acid
<221> NAME/KEY: MISC_FEATURE
<222> LOCATION: (4)..(4)
<223> OTHER INFORMATION: Xaa = any amino acid
<221> NAME/KEY: MISC_FEATURE
<222> LOCATION: (6)..(8)
<223> OTHER INFORMATION: Xaa = any amino acid

<400> SEQUENCE: 70

Cys Xaa Tyr Xaa Asn Xaa Xaa Xaa Cys
1               5

<210> SEQ ID NO 71
<211> LENGTH: 9
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(2)
<223> OTHER INFORMATION: Xaa = any amino acid
<221> NAME/KEY: MISC_FEATURE
<222> LOCATION: (3)..(3)
<223> OTHER INFORMATION: Xaa = any amino acid
<221> NAME/KEY: MISC_FEATURE
<222> LOCATION: (5)..(5)
<223> OTHER INFORMATION: Xaa = any amino acid
<221> NAME/KEY: MISC_FEATURE
<222> LOCATION: (7)..(8)
<223> OTHER INFORMATION: Xaa = any amino acid

<400> SEQUENCE: 71

Cys Xaa Xaa Tyr Xaa Asn Xaa Xaa Cys
1               5
```

```
<210> SEQ ID NO 72
<211> LENGTH: 9
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(4)
<223> OTHER INFORMATION: Xaa = any amino acid
<221> NAME/KEY: MISC_FEATURE
<222> LOCATION: (6)..(6)
<223> OTHER INFORMATION: Xaa = any amino acid
<221> NAME/KEY: MISC_FEATURE
<222> LOCATION: (8)..(8)
<223> OTHER INFORMATION: Xaa = any amino acid

<400> SEQUENCE: 72

Cys Xaa Xaa Xaa Tyr Xaa Asn Xaa Cys
1               5

<210> SEQ ID NO 73
<211> LENGTH: 9
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(4)
<223> OTHER INFORMATION: Xaa = any amino acid
<221> NAME/KEY: MISC_FEATURE
<222> LOCATION: (5)..(5)
<223> OTHER INFORMATION: Xaa = any amino acid
<221> NAME/KEY: MISC_FEATURE
<222> LOCATION: (7)..(7)
<223> OTHER INFORMATION: Xaa = any amino acid

<400> SEQUENCE: 73

Cys Xaa Xaa Xaa Xaa Tyr Xaa Asn Cys
1               5

<210> SEQ ID NO 74
<211> LENGTH: 10
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (3)..(3)
<223> OTHER INFORMATION: Xaa = any amino acid
<221> NAME/KEY: MISC_FEATURE
<222> LOCATION: (5)..(9)
<223> OTHER INFORMATION: Xaa = any amino acid

<400> SEQUENCE: 74

Cys Tyr Xaa Asn Xaa Xaa Xaa Xaa Xaa Cys
1               5                   10

<210> SEQ ID NO 75
<211> LENGTH: 10
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(2)
<223> OTHER INFORMATION: Xaa = any amino acid
<221> NAME/KEY: MISC_FEATURE
<222> LOCATION: (4)..(4)
<223> OTHER INFORMATION: Xaa = any amino acid
<221> NAME/KEY: MISC_FEATURE
<222> LOCATION: (6)..(9)
<223> OTHER INFORMATION: Xaa = any amino acid
```

```
<400> SEQUENCE: 75

Cys Xaa Tyr Xaa Asn Xaa Xaa Xaa Xaa Cys
1               5                   10

<210> SEQ ID NO 76
<211> LENGTH: 10
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(3)
<223> OTHER INFORMATION: Xaa = any amino acid
<221> NAME/KEY: MISC_FEATURE
<222> LOCATION: (5)..(5)
<223> OTHER INFORMATION: Xaa = any amino acid
<221> NAME/KEY: MISC_FEATURE
<222> LOCATION: (7)..(9)
<223> OTHER INFORMATION: Xaa = any amino acid

<400> SEQUENCE: 76

Cys Xaa Xaa Tyr Xaa Asn Xaa Xaa Xaa Cys
1               5                   10

<210> SEQ ID NO 77
<211> LENGTH: 10
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(4)
<223> OTHER INFORMATION: Xaa = any amino acid
<221> NAME/KEY: MISC_FEATURE
<222> LOCATION: (6)..(6)
<223> OTHER INFORMATION: Xaa = any amino acid
<221> NAME/KEY: MISC_FEATURE
<222> LOCATION: (8)..(9)
<223> OTHER INFORMATION: Xaa = any amino acid

<400> SEQUENCE: 77

Cys Xaa Xaa Xaa Tyr Xaa Asn Xaa Xaa Cys
1               5                   10

<210> SEQ ID NO 78
<211> LENGTH: 10
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(5)
<223> OTHER INFORMATION: Xaa = any amino acid
<221> NAME/KEY: MISC_FEATURE
<222> LOCATION: (7)..(7)
<223> OTHER INFORMATION: Xaa = any amino acid
<221> NAME/KEY: MISC_FEATURE
<222> LOCATION: (9)..(9)
<223> OTHER INFORMATION: Xaa = any amino acid

<400> SEQUENCE: 78

Cys Xaa Xaa Xaa Xaa Tyr Xaa Asn Xaa Cys
1               5                   10

<210> SEQ ID NO 79
<211> LENGTH: 10
<212> TYPE: PRT
<213> ORGANISM: Artificial Sequence
<220> FEATURE:
<223> OTHER INFORMATION: One Embodiment of General Formula
<221> NAME/KEY: MISC_FEATURE
```

```
<222> LOCATION: (2)..(6)
<223> OTHER INFORMATION: Xaa = any amino acid
<221> NAME/KEY: MISC_FEATURE
<222> LOCATION: (8)..(8)
<223> OTHER INFORMATION: Xaa = any amino acid

<400> SEQUENCE: 79

Cys Xaa Xaa Xaa Xaa Xaa Tyr Xaa Asn Cys
1               5                   10

<210> SEQ ID NO 80
<211> LENGTH: 11
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (3)..(3)
<223> OTHER INFORMATION: Xaa = any amino acid
<221> NAME/KEY: MISC_FEATURE
<222> LOCATION: (5)..(10)
<223> OTHER INFORMATION: Xaa = any amino acid

<400> SEQUENCE: 80

Cys Tyr Xaa Asn Xaa Xaa Xaa Xaa Xaa Xaa Cys
1               5                   10

<210> SEQ ID NO 81
<211> LENGTH: 11
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(2)
<223> OTHER INFORMATION: Xaa = any amino acid
<221> NAME/KEY: MISC_FEATURE
<222> LOCATION: (4)..(4)
<223> OTHER INFORMATION: Xaa = any amino acid
<221> NAME/KEY: MISC_FEATURE
<222> LOCATION: (6)..(10)
<223> OTHER INFORMATION: Xaa = any amino acid

<400> SEQUENCE: 81

Cys Xaa Tyr Xaa Asn Xaa Xaa Xaa Xaa Xaa Cys
1               5                   10

<210> SEQ ID NO 82
<211> LENGTH: 11
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(3)
<223> OTHER INFORMATION: Xaa = any amino acid
<221> NAME/KEY: MISC_FEATURE
<222> LOCATION: (5)..(5)
<223> OTHER INFORMATION: Xaa = any amino acid
<221> NAME/KEY: MISC_FEATURE
<222> LOCATION: (7)..(10)
<223> OTHER INFORMATION: Xaa = any amino acid

<400> SEQUENCE: 82

Cys Xaa Xaa Tyr Xaa Asn Xaa Xaa Xaa Xaa Cys
1               5                   10

<210> SEQ ID NO 83
<211> LENGTH: 11
<212> TYPE: PRT
<213> ORGANISM: Artificial Sequence
```

```
<220> FEATURE:
<223> OTHER INFORMATION: One Embodiment of General Formula
<221> NAME/KEY: MISC_FEATURE
<222> LOCATION: (2)..(4)
<223> OTHER INFORMATION: Xaa = any amino acid
<221> NAME/KEY: MISC_FEATURE
<222> LOCATION: (6)..(6)
<223> OTHER INFORMATION: Xaa = any amino acid
<221> NAME/KEY: MISC_FEATURE
<222> LOCATION: (8)..(10)
<223> OTHER INFORMATION: Xaa = any amino acid

<400> SEQUENCE: 83

Cys Xaa Xaa Xaa Tyr Xaa Asn Xaa Xaa Xaa Cys
1               5                   10

<210> SEQ ID NO 84
<211> LENGTH: 11
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(5)
<223> OTHER INFORMATION: Xaa = any amino acid
<221> NAME/KEY: MISC_FEATURE
<222> LOCATION: (7)..(7)
<223> OTHER INFORMATION: Xaa = any amino acid
<221> NAME/KEY: MISC_FEATURE
<222> LOCATION: (9)..(10)
<223> OTHER INFORMATION: Xaa = any amino acid

<400> SEQUENCE: 84

Cys Xaa Xaa Xaa Xaa Tyr Xaa Asn Xaa Xaa Cys
1               5                   10

<210> SEQ ID NO 85
<211> LENGTH: 11
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(6)
<223> OTHER INFORMATION: Xaa = any amino acid
<221> NAME/KEY: MISC_FEATURE
<222> LOCATION: (8)..(8)
<223> OTHER INFORMATION: Xaa = any amino acid
<221> NAME/KEY: MISC_FEATURE
<222> LOCATION: (10)..(10)
<223> OTHER INFORMATION: Xaa = any amino acid

<400> SEQUENCE: 85

Cys Xaa Xaa Xaa Xaa Xaa Tyr Xaa Asn Xaa Cys
1               5                   10

<210> SEQ ID NO 86
<211> LENGTH: 11
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(7)
<223> OTHER INFORMATION: Xaa = any amino acid
<221> NAME/KEY: MISC_FEATURE
<222> LOCATION: (9)..(9)
<223> OTHER INFORMATION: Xaa = any amino acid

<400> SEQUENCE: 86

Cys Xaa Xaa Xaa Xaa Xaa Xaa Tyr Xaa Asn Cys
1               5                   10
```

```
<210> SEQ ID NO 87
<211> LENGTH: 12
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (3)..(3)
<223> OTHER INFORMATION: Xaa = any amino acid
<221> NAME/KEY: MISC_FEATURE
<222> LOCATION: (5)..(11)
<223> OTHER INFORMATION: Xaa = any amino acid

<400> SEQUENCE: 87

Cys Tyr Xaa Asn Xaa Xaa Xaa Xaa Xaa Xaa Xaa Cys
1               5                   10

<210> SEQ ID NO 88
<211> LENGTH: 12
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(2)
<223> OTHER INFORMATION: Xaa = any amino acid
<221> NAME/KEY: MISC_FEATURE
<222> LOCATION: (4)..(4)
<223> OTHER INFORMATION: Xaa = any amino acid
<221> NAME/KEY: MISC_FEATURE
<222> LOCATION: (6)..(11)
<223> OTHER INFORMATION: Xaa = any amino acid

<400> SEQUENCE: 88

Cys Xaa Tyr Xaa Asn Xaa Xaa Xaa Xaa Xaa Xaa Cys
1               5                   10

<210> SEQ ID NO 89
<211> LENGTH: 12
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(3)
<223> OTHER INFORMATION: Xaa = any amino acid
<221> NAME/KEY: MISC_FEATURE
<222> LOCATION: (5)..(5)
<223> OTHER INFORMATION: Xaa = any amino acid
<221> NAME/KEY: MISC_FEATURE
<222> LOCATION: (7)..(11)
<223> OTHER INFORMATION: Xaa = any amino acid

<400> SEQUENCE: 89

Cys Xaa Xaa Tyr Xaa Asn Xaa Xaa Xaa Xaa Xaa Cys
1               5                   10

<210> SEQ ID NO 90
<211> LENGTH: 12
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(4)
<223> OTHER INFORMATION: Xaa = any amino acid
<221> NAME/KEY: MISC_FEATURE
<222> LOCATION: (6)..(6)
<223> OTHER INFORMATION: Xaa = any amino acid
<221> NAME/KEY: MISC_FEATURE
<222> LOCATION: (8)..(11)
```

<223> OTHER INFORMATION: Xaa = any amino acid

<400> SEQUENCE: 90

Cys Xaa Xaa Xaa Tyr Xaa Asn Xaa Xaa Xaa Xaa Cys
1               5                   10

<210> SEQ ID NO 91
<211> LENGTH: 12
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(5)
<223> OTHER INFORMATION: Xaa = any amino acid
<221> NAME/KEY: MISC_FEATURE
<222> LOCATION: (7)..(7)
<223> OTHER INFORMATION: Xaa = any amino acid
<221> NAME/KEY: MISC_FEATURE
<222> LOCATION: (9)..(11)
<223> OTHER INFORMATION: Xaa = any amino acid

<400> SEQUENCE: 91

Cys Xaa Xaa Xaa Xaa Tyr Xaa Asn Xaa Xaa Xaa Cys
1               5                   10

<210> SEQ ID NO 92
<211> LENGTH: 12
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(6)
<223> OTHER INFORMATION: Xaa = any amino acid
<221> NAME/KEY: MISC_FEATURE
<222> LOCATION: (8)..(8)
<223> OTHER INFORMATION: Xaa = any amino acid
<221> NAME/KEY: MISC_FEATURE
<222> LOCATION: (10)..(11)
<223> OTHER INFORMATION: Xaa = any amino acid

<400> SEQUENCE: 92

Cys Xaa Xaa Xaa Xaa Xaa Tyr Xaa Asn Xaa Xaa Cys
1               5                   10

<210> SEQ ID NO 93
<211> LENGTH: 12
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(7)
<223> OTHER INFORMATION: Xaa = any amino acid
<221> NAME/KEY: MISC_FEATURE
<222> LOCATION: (9)..(9)
<223> OTHER INFORMATION: Xaa = any amino acid
<221> NAME/KEY: MISC_FEATURE
<222> LOCATION: (11)..(11)
<223> OTHER INFORMATION: Xaa = any amino acid

<400> SEQUENCE: 93

Cys Xaa Xaa Xaa Xaa Xaa Xaa Tyr Xaa Asn Xaa Cys
1               5                   10

<210> SEQ ID NO 94
<211> LENGTH: 12
<212> TYPE: PRT
<213> ORGANISM: Artificial Sequence
<220> FEATURE:

```
<223> OTHER INFORMATION: One Embodiment of General Formula
<221> NAME/KEY: MISC_FEATURE
<222> LOCATION: (2)..(8)
<223> OTHER INFORMATION: Xaa = any amino acid
<221> NAME/KEY: MISC_FEATURE
<222> LOCATION: (10)..(10)
<223> OTHER INFORMATION: Xaa = any amino acid

<400> SEQUENCE: 94

Cys Xaa Xaa Xaa Xaa Xaa Xaa Xaa Tyr Xaa Asn Cys
1               5                   10

<210> SEQ ID NO 95
<211> LENGTH: 13
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (3)..(3)
<223> OTHER INFORMATION: Xaa = any amino acid
<221> NAME/KEY: MISC_FEATURE
<222> LOCATION: (5)..(12)
<223> OTHER INFORMATION: Xaa = any amino acid

<400> SEQUENCE: 95

Cys Tyr Xaa Asn Xaa Xaa Xaa Xaa Xaa Xaa Xaa Cys
1               5                   10

<210> SEQ ID NO 96
<211> LENGTH: 13
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(2)
<223> OTHER INFORMATION: Xaa = any amino acid
<221> NAME/KEY: MISC_FEATURE
<222> LOCATION: (4)..(4)
<223> OTHER INFORMATION: Xaa = any amino acid
<221> NAME/KEY: MISC_FEATURE
<222> LOCATION: (6)..(12)
<223> OTHER INFORMATION: Xaa = any amino acid

<400> SEQUENCE: 96

Cys Xaa Tyr Xaa Asn Xaa Xaa Xaa Xaa Xaa Xaa Cys
1               5                   10

<210> SEQ ID NO 97
<211> LENGTH: 13
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(3)
<223> OTHER INFORMATION: Xaa = any amino acid
<221> NAME/KEY: MISC_FEATURE
<222> LOCATION: (5)..(5)
<223> OTHER INFORMATION: Xaa = any amino acid
<221> NAME/KEY: MISC_FEATURE
<222> LOCATION: (7)..(12)
<223> OTHER INFORMATION: Xaa = any amino acid

<400> SEQUENCE: 97

Cys Xaa Xaa Tyr Xaa Asn Xaa Xaa Xaa Xaa Xaa Cys
1               5                   10

<210> SEQ ID NO 98
<211> LENGTH: 13
```

```
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(4)
<223> OTHER INFORMATION: Xaa = any amino acid
<221> NAME/KEY: MISC_FEATURE
<222> LOCATION: (6)..(6)
<223> OTHER INFORMATION: Xaa = any amino acid
<221> NAME/KEY: MISC_FEATURE
<222> LOCATION: (8)..(12)
<223> OTHER INFORMATION: Xaa = any amino acid

<400> SEQUENCE: 98

Cys Xaa Xaa Xaa Tyr Xaa Asn Xaa Xaa Xaa Xaa Xaa Cys
1               5                   10

<210> SEQ ID NO 99
<211> LENGTH: 13
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(5)
<223> OTHER INFORMATION: Xaa = any amino acid
<221> NAME/KEY: MISC_FEATURE
<222> LOCATION: (7)..(7)
<223> OTHER INFORMATION: Xaa = any amino acid
<221> NAME/KEY: MISC_FEATURE
<222> LOCATION: (9)..(12)
<223> OTHER INFORMATION: Xaa = any amino acid

<400> SEQUENCE: 99

Cys Xaa Xaa Xaa Xaa Tyr Xaa Asn Xaa Xaa Xaa Xaa Cys
1               5                   10

<210> SEQ ID NO 100
<211> LENGTH: 13
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(6)
<223> OTHER INFORMATION: Xaa = any amino acid
<221> NAME/KEY: MISC_FEATURE
<222> LOCATION: (8)..(8)
<223> OTHER INFORMATION: Xaa = any amino acid
<221> NAME/KEY: MISC_FEATURE
<222> LOCATION: (10)..(12)
<223> OTHER INFORMATION: Xaa = any amino acid

<400> SEQUENCE: 100

Cys Xaa Xaa Xaa Xaa Xaa Tyr Xaa Asn Xaa Xaa Xaa Cys
1               5                   10

<210> SEQ ID NO 101
<211> LENGTH: 13
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(7)
<223> OTHER INFORMATION: Xaa = any amino acid
<221> NAME/KEY: MISC_FEATURE
<222> LOCATION: (9)..(9)
<223> OTHER INFORMATION: Xaa = any amino acid
<221> NAME/KEY: MISC_FEATURE
<222> LOCATION: (10)..(12)
<223> OTHER INFORMATION: Xaa = any amino acid
```

```
<400> SEQUENCE: 101

Cys Xaa Xaa Xaa Xaa Xaa Xaa Tyr Xaa Asn Xaa Xaa Cys
1               5                   10

<210> SEQ ID NO 102
<211> LENGTH: 13
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(8)
<223> OTHER INFORMATION: Xaa = any amino acid
<221> NAME/KEY: MISC_FEATURE
<222> LOCATION: (10)..(10)
<223> OTHER INFORMATION: Xaa = any amino acid
<221> NAME/KEY: MISC_FEATURE
<222> LOCATION: (12)..(12)
<223> OTHER INFORMATION: Xaa = any amino acid

<400> SEQUENCE: 102

Cys Xaa Xaa Xaa Xaa Xaa Xaa Xaa Tyr Xaa Asn Xaa Cys
1               5                   10

<210> SEQ ID NO 103
<211> LENGTH: 13
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(9)
<223> OTHER INFORMATION: Xaa = any amino acid
<221> NAME/KEY: MISC_FEATURE
<222> LOCATION: (11)..(11)
<223> OTHER INFORMATION: Xaa = any amino acid

<400> SEQUENCE: 103

Cys Xaa Xaa Xaa Xaa Xaa Xaa Xaa Xaa Tyr Xaa Asn Cys
1               5                   10

<210> SEQ ID NO 104
<211> LENGTH: 14
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (3)..(3)
<223> OTHER INFORMATION: Xaa = any amino acid
<221> NAME/KEY: MISC_FEATURE
<222> LOCATION: (5)..(13)
<223> OTHER INFORMATION: Xaa = any amino acid

<400> SEQUENCE: 104

Cys Tyr Xaa Asn Xaa Xaa Xaa Xaa Xaa Xaa Xaa Xaa Cys
1               5                   10

<210> SEQ ID NO 105
<211> LENGTH: 14
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(2)
<223> OTHER INFORMATION: Xaa = any amino acid
<221> NAME/KEY: MISC_FEATURE
<222> LOCATION: (4)..(4)
<223> OTHER INFORMATION: Xaa = any amino acid
```

```
<221> NAME/KEY: MISC_FEATURE
<222> LOCATION: (6)..(13)
<223> OTHER INFORMATION: Xaa = any amino acid

<400> SEQUENCE: 105

Cys Xaa Tyr Xaa Asn Xaa Xaa Xaa Xaa Xaa Xaa Xaa Xaa Cys
1               5                   10

<210> SEQ ID NO 106
<211> LENGTH: 14
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(3)
<223> OTHER INFORMATION: Xaa = any amino acid
<221> NAME/KEY: MISC_FEATURE
<222> LOCATION: (5)..(5)
<223> OTHER INFORMATION: Xaa = any amino acid
<221> NAME/KEY: MISC_FEATURE
<222> LOCATION: (7)..(13)
<223> OTHER INFORMATION: Xaa = any amino acid

<400> SEQUENCE: 106

Cys Xaa Xaa Tyr Xaa Asn Xaa Xaa Xaa Xaa Xaa Xaa Xaa Cys
1               5                   10

<210> SEQ ID NO 107
<211> LENGTH: 14
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(4)
<223> OTHER INFORMATION: Xaa = any amino acid
<221> NAME/KEY: MISC_FEATURE
<222> LOCATION: (6)..(6)
<223> OTHER INFORMATION: Xaa = any amino acid
<221> NAME/KEY: MISC_FEATURE
<222> LOCATION: (8)..(13)
<223> OTHER INFORMATION: Xaa = any amino acid

<400> SEQUENCE: 107

Cys Xaa Xaa Xaa Tyr Xaa Asn Xaa Xaa Xaa Xaa Xaa Xaa Cys
1               5                   10

<210> SEQ ID NO 108
<211> LENGTH: 14
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(5)
<223> OTHER INFORMATION: Xaa = any amino acid
<221> NAME/KEY: MISC_FEATURE
<222> LOCATION: (7)..(7)
<223> OTHER INFORMATION: Xaa = any amino acid
<221> NAME/KEY: MISC_FEATURE
<222> LOCATION: (9)..(13)
<223> OTHER INFORMATION: Xaa = any amino acid

<400> SEQUENCE: 108

Cys Xaa Xaa Xaa Xaa Tyr Xaa Asn Xaa Xaa Xaa Xaa Xaa Cys
1               5                   10

<210> SEQ ID NO 109
<211> LENGTH: 14
<212> TYPE: PRT
```

```
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(6)
<223> OTHER INFORMATION: Xaa = any amino acid
<221> NAME/KEY: MISC_FEATURE
<222> LOCATION: (8)..(8)
<223> OTHER INFORMATION: Xaa = any amino acid
<221> NAME/KEY: MISC_FEATURE
<222> LOCATION: (10)..(13)
<223> OTHER INFORMATION: Xaa = any amino acid

<400> SEQUENCE: 109

Cys Xaa Xaa Xaa Xaa Xaa Tyr Xaa Asn Xaa Xaa Xaa Xaa Cys
 1               5                  10

<210> SEQ ID NO 110
<211> LENGTH: 14
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(7)
<223> OTHER INFORMATION: Xaa = any amino acid
<221> NAME/KEY: MISC_FEATURE
<222> LOCATION: (9)..(9)
<223> OTHER INFORMATION: Xaa = any amino acid
<221> NAME/KEY: MISC_FEATURE
<222> LOCATION: (11)..(13)
<223> OTHER INFORMATION: Xaa = any amino acid

<400> SEQUENCE: 110

Cys Xaa Xaa Xaa Xaa Xaa Xaa Tyr Xaa Asn Xaa Xaa Xaa Cys
 1               5                  10

<210> SEQ ID NO 111
<211> LENGTH: 14
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(8)
<223> OTHER INFORMATION: Xaa = any amino acid
<221> NAME/KEY: MISC_FEATURE
<222> LOCATION: (10)..(10)
<223> OTHER INFORMATION: Xaa = any amino acid
<221> NAME/KEY: MISC_FEATURE
<222> LOCATION: (12)..(13)
<223> OTHER INFORMATION: Xaa = any amino acid

<400> SEQUENCE: 111

Cys Xaa Xaa Xaa Xaa Xaa Xaa Xaa Tyr Xaa Asn Xaa Xaa Cys
 1               5                  10

<210> SEQ ID NO 112
<211> LENGTH: 14
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(9)
<223> OTHER INFORMATION: Xaa = any amino acid
<221> NAME/KEY: MISC_FEATURE
<222> LOCATION: (11)..(11)
<223> OTHER INFORMATION: Xaa = any amino acid
<221> NAME/KEY: MISC_FEATURE
<222> LOCATION: (13)..(13)
<223> OTHER INFORMATION: Xaa = any amino acid
```

```
<400> SEQUENCE: 112

Cys Xaa Xaa Xaa Xaa Xaa Xaa Xaa Xaa Tyr Xaa Asn Xaa Cys
1               5                   10

<210> SEQ ID NO 113
<211> LENGTH: 14
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(10)
<223> OTHER INFORMATION: Xaa = any amino acid
<221> NAME/KEY: MISC_FEATURE
<222> LOCATION: (12)..(12)
<223> OTHER INFORMATION: Xaa = any amino acid

<400> SEQUENCE: 113

Cys Xaa Xaa Xaa Xaa Xaa Xaa Xaa Xaa Xaa Tyr Xaa Asn Cys
1               5                   10

<210> SEQ ID NO 114
<211> LENGTH: 15
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (3)..(3)
<223> OTHER INFORMATION: Xaa = any amino acid
<221> NAME/KEY: MISC_FEATURE
<222> LOCATION: (5)..(14)
<223> OTHER INFORMATION: Xaa = any amino acid

<400> SEQUENCE: 114

Cys Tyr Xaa Asn Xaa Xaa Xaa Xaa Xaa Xaa Xaa Xaa Xaa Xaa Cys
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(2)
<223> OTHER INFORMATION: Xaa = any amino acid
<221> NAME/KEY: MISC_FEATURE
<222> LOCATION: (4)..(4)
<223> OTHER INFORMATION: Xaa = any amino acid
<221> NAME/KEY: MISC_FEATURE
<222> LOCATION: (6)..(14)
<223> OTHER INFORMATION: Xaa = any amino acid

<400> SEQUENCE: 115

Cys Xaa Tyr Xaa Asn Xaa Xaa Xaa Xaa Xaa Xaa Xaa Xaa Xaa Cys
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(3)
<223> OTHER INFORMATION: Xaa = any amino acid
<221> NAME/KEY: MISC_FEATURE
<222> LOCATION: (5)..(5)
<223> OTHER INFORMATION: Xaa = any amino acid
<221> NAME/KEY: MISC_FEATURE
```

<222> LOCATION: (7)..(14)
<223> OTHER INFORMATION: Xaa = any amino acid

<400> SEQUENCE: 116

Cys Xaa Xaa Tyr Xaa Asn Xaa Xaa Xaa Xaa Xaa Xaa Xaa Xaa Cys
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(4)
<223> OTHER INFORMATION: Xaa = any amino acid
<221> NAME/KEY: MISC_FEATURE
<222> LOCATION: (6)..(6)
<223> OTHER INFORMATION: Xaa = any amino acid
<221> NAME/KEY: MISC_FEATURE
<222> LOCATION: (8)..(14)
<223> OTHER INFORMATION: Xaa = any amino acid

<400> SEQUENCE: 117

Cys Xaa Xaa Xaa Tyr Xaa Asn Xaa Xaa Xaa Xaa Xaa Xaa Xaa Cys
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(5)
<223> OTHER INFORMATION: Xaa = any amino acid
<221> NAME/KEY: MISC_FEATURE
<222> LOCATION: (7)..(7)
<223> OTHER INFORMATION: Xaa = any amino acid
<221> NAME/KEY: MISC_FEATURE
<222> LOCATION: (9)..(14)
<223> OTHER INFORMATION: Xaa = any amino acid

<400> SEQUENCE: 118

Cys Xaa Xaa Xaa Xaa Tyr Xaa Asn Xaa Xaa Xaa Xaa Xaa Xaa Cys
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(6)
<223> OTHER INFORMATION: Xaa = any amino acid
<221> NAME/KEY: MISC_FEATURE
<222> LOCATION: (8)..(8)
<223> OTHER INFORMATION: Xaa = any amino acid
<221> NAME/KEY: MISC_FEATURE
<222> LOCATION: (10)..(14)
<223> OTHER INFORMATION: Xaa = any amino acid

<400> SEQUENCE: 119

Cys Xaa Xaa Xaa Xaa Xaa Tyr Xaa Asn Xaa Xaa Xaa Xaa Xaa Cys
1               5                   10                  15

<210> SEQ ID NO 120
<211> LENGTH: 15
<212> TYPE: PRT
<213> ORGANISM: Artificial Sequence

```
<220> FEATURE:
<223> OTHER INFORMATION: One Embodiment of General Formula
<221> NAME/KEY: MISC_FEATURE
<222> LOCATION: (2)..(7)
<223> OTHER INFORMATION: Xaa = any amino acid
<221> NAME/KEY: MISC_FEATURE
<222> LOCATION: (9)..(9)
<223> OTHER INFORMATION: Xaa = any amino acid
<221> NAME/KEY: MISC_FEATURE
<222> LOCATION: (11)..(14)
<223> OTHER INFORMATION: Xaa = any amino acid

<400> SEQUENCE: 120

Cys Xaa Xaa Xaa Xaa Xaa Xaa Tyr Xaa Asn Xaa Xaa Xaa Xaa Cys
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(8)
<223> OTHER INFORMATION: Xaa = any amino acid
<221> NAME/KEY: MISC_FEATURE
<222> LOCATION: (10)..(10)
<223> OTHER INFORMATION: Xaa = any amino acid
<221> NAME/KEY: MISC_FEATURE
<222> LOCATION: (12)..(14)
<223> OTHER INFORMATION: Xaa = any amino acid

<400> SEQUENCE: 121

Cys Xaa Xaa Xaa Xaa Xaa Xaa Xaa Tyr Xaa Asn Xaa Xaa Xaa Cys
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(9)
<223> OTHER INFORMATION: Xaa = any amino acid
<221> NAME/KEY: MISC_FEATURE
<222> LOCATION: (11)..(11)
<223> OTHER INFORMATION: Xaa = any amino acid
<221> NAME/KEY: MISC_FEATURE
<222> LOCATION: (13)..(14)
<223> OTHER INFORMATION: Xaa = any amino acid

<400> SEQUENCE: 122

Cys Xaa Xaa Xaa Xaa Xaa Xaa Xaa Xaa Tyr Xaa Asn Xaa Xaa Cys
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(10)
<223> OTHER INFORMATION: Xaa = any amino acid
<221> NAME/KEY: MISC_FEATURE
<222> LOCATION: (12)..(12)
<223> OTHER INFORMATION: Xaa = any amino acid
<221> NAME/KEY: MISC_FEATURE
<222> LOCATION: (14)..(14)
<223> OTHER INFORMATION: Xaa = any amino acid

<400> SEQUENCE: 123
```

```
Cys Xaa Xaa Xaa Xaa Xaa Xaa Xaa Xaa Tyr Xaa Asn Xaa Cys
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(11)
<223> OTHER INFORMATION: Xaa = any amino acid
<221> NAME/KEY: MISC_FEATURE
<222> LOCATION: (13)..(13)
<223> OTHER INFORMATION: Xaa = any amino acid

<400> SEQUENCE: 124

Cys Xaa Xaa Xaa Xaa Xaa Xaa Xaa Xaa Xaa Xaa Tyr Xaa Asn Cys
1               5                   10                  15

<210> SEQ ID NO 125
<211> LENGTH: 16
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (3)..(3)
<223> OTHER INFORMATION: Xaa = any amino acid
<221> NAME/KEY: MISC_FEATURE
<222> LOCATION: (5)..(15)
<223> OTHER INFORMATION: Xaa = any amino acid

<400> SEQUENCE: 125

Cys Tyr Xaa Asn Xaa Xaa Xaa Xaa Xaa Xaa Xaa Xaa Xaa Xaa Xaa Cys
1               5                   10                  15

<210> SEQ ID NO 126
<211> LENGTH: 16
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(2)
<223> OTHER INFORMATION: Xaa = any amino acid
<221> NAME/KEY: MISC_FEATURE
<222> LOCATION: (4)..(4)
<223> OTHER INFORMATION: Xaa = any amino acid
<221> NAME/KEY: MISC_FEATURE
<222> LOCATION: (6)..(15)
<223> OTHER INFORMATION: Xaa = any amino acid

<400> SEQUENCE: 126

Cys Xaa Tyr Xaa Asn Xaa Xaa Xaa Xaa Xaa Xaa Xaa Xaa Xaa Xaa Cys
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(3)
<223> OTHER INFORMATION: Xaa = any amino acid
<221> NAME/KEY: MISC_FEATURE
<222> LOCATION: (5)..(5)
<223> OTHER INFORMATION: Xaa = any amino acid
<221> NAME/KEY: MISC_FEATURE
<222> LOCATION: (7)..(15)
```

<223> OTHER INFORMATION: Xaa = any amino acid

<400> SEQUENCE: 127

Cys Xaa Xaa Tyr Xaa Asn Xaa Xaa Xaa Xaa Xaa Xaa Xaa Xaa Xaa Cys
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(4)
<223> OTHER INFORMATION: Xaa = any amino acid
<221> NAME/KEY: MISC_FEATURE
<222> LOCATION: (6)..(6)
<223> OTHER INFORMATION: Xaa = any amino acid
<221> NAME/KEY: MISC_FEATURE
<222> LOCATION: (8)..(15)
<223> OTHER INFORMATION: Xaa = any amino acid

<400> SEQUENCE: 128

Cys Xaa Xaa Xaa Tyr Xaa Asn Xaa Xaa Xaa Xaa Xaa Xaa Xaa Xaa Cys
1               5                   10                  15

<210> SEQ ID NO 129
<211> LENGTH: 16
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(5)
<223> OTHER INFORMATION: Xaa = any amino acid
<221> NAME/KEY: MISC_FEATURE
<222> LOCATION: (7)..(7)
<223> OTHER INFORMATION: Xaa = any amino acid
<221> NAME/KEY: MISC_FEATURE
<222> LOCATION: (9)..(15)
<223> OTHER INFORMATION: Xaa = any amino acid

<400> SEQUENCE: 129

Cys Xaa Xaa Xaa Xaa Tyr Xaa Asn Xaa Xaa Xaa Xaa Xaa Xaa Xaa Cys
1               5                   10                  15

<210> SEQ ID NO 130
<211> LENGTH: 16
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(6)
<223> OTHER INFORMATION: Xaa = any amino acid
<221> NAME/KEY: MISC_FEATURE
<222> LOCATION: (8)..(8)
<223> OTHER INFORMATION: Xaa = any amino acid
<221> NAME/KEY: MISC_FEATURE
<222> LOCATION: (10)..(15)
<223> OTHER INFORMATION: Xaa = any amino acid

<400> SEQUENCE: 130

Cys Xaa Xaa Xaa Xaa Xaa Tyr Xaa Asn Xaa Xaa Xaa Xaa Xaa Xaa Cys
1               5                   10                  15

<210> SEQ ID NO 131
<211> LENGTH: 16
<212> TYPE: PRT
<213> ORGANISM: Artificial Sequence
<220> FEATURE:

```
<223> OTHER INFORMATION: One Embodiment of General Formula
<221> NAME/KEY: MISC_FEATURE
<222> LOCATION: (2)..(7)
<223> OTHER INFORMATION: Xaa = any amino acid
<221> NAME/KEY: MISC_FEATURE
<222> LOCATION: (9)..(9)
<223> OTHER INFORMATION: Xaa = any amino acid
<221> NAME/KEY: MISC_FEATURE
<222> LOCATION: (11)..(15)
<223> OTHER INFORMATION: Xaa = any amino acid

<400> SEQUENCE: 131

Cys Xaa Xaa Xaa Xaa Xaa Xaa Tyr Xaa Asn Xaa Xaa Xaa Xaa Xaa Cys
1               5                   10                  15

<210> SEQ ID NO 132
<211> LENGTH: 16
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(8)
<223> OTHER INFORMATION: Xaa = any amino acid
<221> NAME/KEY: MISC_FEATURE
<222> LOCATION: (10)..(10)
<223> OTHER INFORMATION: Xaa = any amino acid
<221> NAME/KEY: MISC_FEATURE
<222> LOCATION: (12)..(15)
<223> OTHER INFORMATION: Xaa = any amino acid

<400> SEQUENCE: 132

Cys Xaa Xaa Xaa Xaa Xaa Xaa Xaa Tyr Xaa Asn Xaa Xaa Xaa Xaa Cys
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(9)
<223> OTHER INFORMATION: Xaa = any amino acid
<221> NAME/KEY: MISC_FEATURE
<222> LOCATION: (11)..(11)
<223> OTHER INFORMATION: Xaa = any amino acid
<221> NAME/KEY: MISC_FEATURE
<222> LOCATION: (13)..(15)
<223> OTHER INFORMATION: Xaa = any amino acid

<400> SEQUENCE: 133

Cys Xaa Xaa Xaa Xaa Xaa Xaa Xaa Xaa Tyr Xaa Asn Xaa Xaa Xaa Cys
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(10)
<223> OTHER INFORMATION: Xaa = any amino acid
<221> NAME/KEY: MISC_FEATURE
<222> LOCATION: (12)..(12)
<223> OTHER INFORMATION: Xaa = any amino acid
<221> NAME/KEY: MISC_FEATURE
<222> LOCATION: (14)..(15)
<223> OTHER INFORMATION: Xaa = any amino acid

<400> SEQUENCE: 134
```

```
Cys Xaa Xaa Xaa Xaa Xaa Xaa Xaa Xaa Tyr Xaa Asn Xaa Xaa Cys
1               5                   10                  15
```

<210> SEQ ID NO 135
<211> LENGTH: 16
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(11)
<223> OTHER INFORMATION: Xaa = any amino acid
<221> NAME/KEY: MISC_FEATURE
<222> LOCATION: (13)..(13)
<223> OTHER INFORMATION: Xaa = any amino acid
<221> NAME/KEY: MISC_FEATURE
<222> LOCATION: (15)..(15)
<223> OTHER INFORMATION: Xaa = any amino acid

<400> SEQUENCE: 135

```
Cys Xaa Xaa Xaa Xaa Xaa Xaa Xaa Xaa Xaa Xaa Tyr Xaa Asn Xaa Cys
1               5                   10                  15
```

<210> SEQ ID NO 136
<211> LENGTH: 16
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(12)
<223> OTHER INFORMATION: Xaa = any amino acid
<221> NAME/KEY: MISC_FEATURE
<222> LOCATION: (14)..(14)
<223> OTHER INFORMATION: Xaa = any amino acid

<400> SEQUENCE: 136

```
Cys Xaa Xaa Xaa Xaa Xaa Xaa Xaa Xaa Xaa Xaa Xaa Tyr Xaa Asn Cys
1               5                   10                  15
```

<210> SEQ ID NO 137
<211> LENGTH: 17
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (3)..(3)
<223> OTHER INFORMATION: Xaa = any amino acid
<221> NAME/KEY: MISC_FEATURE
<222> LOCATION: (5)..(16)
<223> OTHER INFORMATION: Xaa = any amino acid

<400> SEQUENCE: 137

```
Cys Tyr Xaa Asn Xaa Xaa Xaa Xaa Xaa Xaa Xaa Xaa Xaa Xaa Xaa Xaa
1               5                   10                  15

Cys
```

<210> SEQ ID NO 138
<211> LENGTH: 17
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(2)
<223> OTHER INFORMATION: Xaa = any amino acid
<221> NAME/KEY: MISC_FEATURE
<222> LOCATION: (4)..(4)
<223> OTHER INFORMATION: Xaa = any amino acid
<221> NAME/KEY: MISC_FEATURE

```
<222> LOCATION: (6)..(16)
<223> OTHER INFORMATION: Xaa = any amino acid

<400> SEQUENCE: 138

Cys Xaa Tyr Xaa Asn Xaa Xaa Xaa Xaa Xaa Xaa Xaa Xaa Xaa Xaa
1               5                   10                  15

Cys

<210> SEQ ID NO 139
<211> LENGTH: 17
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(3)
<223> OTHER INFORMATION: Xaa = any amino acid
<221> NAME/KEY: MISC_FEATURE
<222> LOCATION: (5)..(5)
<223> OTHER INFORMATION: Xaa = any amino acid
<221> NAME/KEY: MISC_FEATURE
<222> LOCATION: (7)..(16)
<223> OTHER INFORMATION: Xaa = any amino acid

<400> SEQUENCE: 139

Cys Xaa Xaa Tyr Xaa Asn Xaa Xaa Xaa Xaa Xaa Xaa Xaa Xaa Xaa
1               5                   10                  15

Cys

<210> SEQ ID NO 140
<211> LENGTH: 17
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(4)
<223> OTHER INFORMATION: Xaa = any amino acid
<221> NAME/KEY: MISC_FEATURE
<222> LOCATION: (6)..(6)
<223> OTHER INFORMATION: Xaa = any amino acid
<221> NAME/KEY: MISC_FEATURE
<222> LOCATION: (8)..(16)
<223> OTHER INFORMATION: Xaa = any amino acid

<400> SEQUENCE: 140

Cys Xaa Xaa Xaa Tyr Xaa Asn Xaa Xaa Xaa Xaa Xaa Xaa Xaa Xaa
1               5                   10                  15

Cys

<210> SEQ ID NO 141
<211> LENGTH: 17
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(5)
<223> OTHER INFORMATION: Xaa = any amino acid
<221> NAME/KEY: MISC_FEATURE
<222> LOCATION: (7)..(7)
<223> OTHER INFORMATION: Xaa = any amino acid
<221> NAME/KEY: MISC_FEATURE
<222> LOCATION: (9)..(16)
<223> OTHER INFORMATION: Xaa = any amino acid

<400> SEQUENCE: 141

Cys Xaa Xaa Xaa Xaa Tyr Xaa Asn Xaa Xaa Xaa Xaa Xaa Xaa Xaa
1               5                   10                  15
```

Cys

<210> SEQ ID NO 142
<211> LENGTH: 17
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(6)
<223> OTHER INFORMATION: Xaa = any amino acid
<221> NAME/KEY: MISC_FEATURE
<222> LOCATION: (8)..(8)
<223> OTHER INFORMATION: Xaa = any amino acid
<221> NAME/KEY: MISC_FEATURE
<222> LOCATION: (10)..(16)
<223> OTHER INFORMATION: Xaa = any amino acid

<400> SEQUENCE: 142

Cys Xaa Xaa Xaa Xaa Xaa Tyr Xaa Asn Xaa Xaa Xaa Xaa Xaa Xaa
1               5                   10                  15

Cys

<210> SEQ ID NO 143
<211> LENGTH: 17
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(7)
<223> OTHER INFORMATION: Xaa = any amino acid
<221> NAME/KEY: MISC_FEATURE
<222> LOCATION: (9)..(9)
<223> OTHER INFORMATION: Xaa = any amino acid
<221> NAME/KEY: MISC_FEATURE
<222> LOCATION: (11)..(16)
<223> OTHER INFORMATION: Xaa = any amino acid

<400> SEQUENCE: 143

Cys Xaa Xaa Xaa Xaa Xaa Xaa Tyr Xaa Asn Xaa Xaa Xaa Xaa Xaa Xaa
1               5                   10                  15

Cys

<210> SEQ ID NO 144
<211> LENGTH: 17
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(7)
<223> OTHER INFORMATION: Xaa = any amino acid
<221> NAME/KEY: MISC_FEATURE
<222> LOCATION: (8)..(8)
<223> OTHER INFORMATION: Xaa = any amino acid
<221> NAME/KEY: MISC_FEATURE
<222> LOCATION: (10)..(16)
<223> OTHER INFORMATION: Xaa = any amino acid

<400> SEQUENCE: 144

Cys Xaa Xaa Xaa Xaa Xaa Xaa Xaa Tyr Xaa Asn Xaa Xaa Xaa Xaa Xaa
1               5                   10                  15

Cys

<210> SEQ ID NO 145
<211> LENGTH: 17
<212> TYPE: PRT

```
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(9)
<223> OTHER INFORMATION: Xaa = any amino acid
<221> NAME/KEY: MISC_FEATURE
<222> LOCATION: (11)..(11)
<223> OTHER INFORMATION: Xaa = any amino acid
<221> NAME/KEY: MISC_FEATURE
<222> LOCATION: (13)..(16)
<223> OTHER INFORMATION: Xaa = any amino acid

<400> SEQUENCE: 145

Cys Xaa Xaa Xaa Xaa Xaa Xaa Xaa Xaa Tyr Xaa Asn Xaa Xaa Xaa Xaa
1               5                   10                  15

Cys

<210> SEQ ID NO 146
<211> LENGTH: 17
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(10)
<223> OTHER INFORMATION: Xaa = any amino acid
<221> NAME/KEY: MISC_FEATURE
<222> LOCATION: (12)..(12)
<223> OTHER INFORMATION: Xaa = any amino acid
<221> NAME/KEY: MISC_FEATURE
<222> LOCATION: (14)..(16)
<223> OTHER INFORMATION: Xaa = any amino acid

<400> SEQUENCE: 146

Cys Xaa Xaa Xaa Xaa Xaa Xaa Xaa Xaa Xaa Tyr Xaa Asn Xaa Xaa Xaa
1               5                   10                  15

Cys

<210> SEQ ID NO 147
<211> LENGTH: 17
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(11)
<223> OTHER INFORMATION: Xaa = any amino acid
<221> NAME/KEY: MISC_FEATURE
<222> LOCATION: (13)..(13)
<223> OTHER INFORMATION: Xaa = any amino acid
<221> NAME/KEY: MISC_FEATURE
<222> LOCATION: (15)..(16)
<223> OTHER INFORMATION: Xaa = any amino acid

<400> SEQUENCE: 147

Cys Xaa Xaa Xaa Xaa Xaa Xaa Xaa Xaa Xaa Xaa Tyr Xaa Asn Xaa Xaa
1               5                   10                  15

Cys

<210> SEQ ID NO 148
<211> LENGTH: 17
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(12)
<223> OTHER INFORMATION: Xaa = any amino acid
<221> NAME/KEY: MISC_FEATURE
```

```
<222> LOCATION: (14)..(14)
<223> OTHER INFORMATION: Xaa = any amino acid
<221> NAME/KEY: MISC_FEATURE
<222> LOCATION: (16)..(16)
<223> OTHER INFORMATION: Xaa = any amino acid

<400> SEQUENCE: 148

Cys Xaa Xaa Xaa Xaa Xaa Xaa Xaa Xaa Xaa Xaa Xaa Tyr Xaa Asn Xaa
1               5                   10                  15

Cys

<210> SEQ ID NO 149
<211> LENGTH: 17
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(13)
<223> OTHER INFORMATION: Xaa = any amino acid
<221> NAME/KEY: MISC_FEATURE
<222> LOCATION: (15)..(15)
<223> OTHER INFORMATION: Xaa = any amino acid

<400> SEQUENCE: 149

Cys Xaa Xaa Xaa Xaa Xaa Xaa Xaa Xaa Xaa Xaa Xaa Xaa Tyr Xaa Asn
1               5                   10                  15

Cys

<210> SEQ ID NO 150
<211> LENGTH: 18
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (3)..(3)
<223> OTHER INFORMATION: Xaa = any amino acid
<221> NAME/KEY: MISC_FEATURE
<222> LOCATION: (5)..(17)
<223> OTHER INFORMATION: Xaa = any amino acid

<400> SEQUENCE: 150

Cys Tyr Xaa Asn Xaa Xaa Xaa Xaa Xaa Xaa Xaa Xaa Xaa Xaa Xaa
1               5                   10                  15

Xaa Cys

<210> SEQ ID NO 151
<211> LENGTH: 18
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(2)
<223> OTHER INFORMATION: Xaa = any amino acid
<221> NAME/KEY: MISC_FEATURE
<222> LOCATION: (4)..(4)
<223> OTHER INFORMATION: Xaa = any amino acid
<221> NAME/KEY: MISC_FEATURE
<222> LOCATION: (6)..(17)
<223> OTHER INFORMATION: Xaa = any amino acid

<400> SEQUENCE: 151

Cys Xaa Tyr Xaa Asn Xaa Xaa Xaa Xaa Xaa Xaa Xaa Xaa Xaa Xaa
1               5                   10                  15

Xaa Cys
```

```
<210> SEQ ID NO 152
<211> LENGTH: 18
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(3)
<223> OTHER INFORMATION: Xaa = any amino acid
<221> NAME/KEY: MISC_FEATURE
<222> LOCATION: (5)..(5)
<223> OTHER INFORMATION: Xaa = any amino acid
<221> NAME/KEY: MISC_FEATURE
<222> LOCATION: (7)..(17)
<223> OTHER INFORMATION: Xaa = any amino acid

<400> SEQUENCE: 152

Cys Xaa Xaa Tyr Xaa Asn Xaa Xaa Xaa Xaa Xaa Xaa Xaa Xaa Xaa
1               5                   10                  15

Xaa Cys

<210> SEQ ID NO 153
<211> LENGTH: 18
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(4)
<223> OTHER INFORMATION: Xaa = any amino acid
<221> NAME/KEY: MISC_FEATURE
<222> LOCATION: (6)..(6)
<223> OTHER INFORMATION: Xaa = any amino acid
<221> NAME/KEY: MISC_FEATURE
<222> LOCATION: (8)..(17)
<223> OTHER INFORMATION: Xaa = any amino acid

<400> SEQUENCE: 153

Cys Xaa Xaa Xaa Tyr Xaa Asn Xaa Xaa Xaa Xaa Xaa Xaa Xaa Xaa
1               5                   10                  15

Xaa Cys

<210> SEQ ID NO 154
<211> LENGTH: 18
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(5)
<223> OTHER INFORMATION: Xaa = any amino acid
<221> NAME/KEY: MISC_FEATURE
<222> LOCATION: (7)..(7)
<223> OTHER INFORMATION: Xaa = any amino acid
<221> NAME/KEY: MISC_FEATURE
<222> LOCATION: (9)..(17)
<223> OTHER INFORMATION: Xaa = any amino acid

<400> SEQUENCE: 154

Cys Xaa Xaa Xaa Xaa Tyr Xaa Asn Xaa Xaa Xaa Xaa Xaa Xaa Xaa
1               5                   10                  15

Xaa Cys

<210> SEQ ID NO 155
<211> LENGTH: 18
<212> TYPE: PRT
<213> ORGANISM: Artificial Sequence
<220> FEATURE:
<223> OTHER INFORMATION: One Embodiment of General Formula
```

```
<221> NAME/KEY: MISC_FEATURE
<222> LOCATION: (2)..(6)
<223> OTHER INFORMATION: Xaa = any amino acid
<221> NAME/KEY: MISC_FEATURE
<222> LOCATION: (8)..(8)
<223> OTHER INFORMATION: Xaa = any amino acid
<221> NAME/KEY: MISC_FEATURE
<222> LOCATION: (10)..(17)
<223> OTHER INFORMATION: Xaa = any amino acid

<400> SEQUENCE: 155

Cys Xaa Xaa Xaa Xaa Xaa Tyr Xaa Asn Xaa Xaa Xaa Xaa Xaa Xaa
1               5                   10                  15

Xaa Cys

<210> SEQ ID NO 156
<211> LENGTH: 18
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(7)
<223> OTHER INFORMATION: Xaa = any amino acid
<221> NAME/KEY: MISC_FEATURE
<222> LOCATION: (9)..(9)
<223> OTHER INFORMATION: Xaa = any amino acid
<221> NAME/KEY: MISC_FEATURE
<222> LOCATION: (11)..(17)
<223> OTHER INFORMATION: Xaa = any amino acid

<400> SEQUENCE: 156

Cys Xaa Xaa Xaa Xaa Xaa Xaa Tyr Xaa Asn Xaa Xaa Xaa Xaa Xaa
1               5                   10                  15

Xaa Cys

<210> SEQ ID NO 157
<211> LENGTH: 18
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(8)
<223> OTHER INFORMATION: Xaa = any amino acid
<221> NAME/KEY: MISC_FEATURE
<222> LOCATION: (10)..(10)
<223> OTHER INFORMATION: Xaa = any amino acid
<221> NAME/KEY: MISC_FEATURE
<222> LOCATION: (12)..(17)
<223> OTHER INFORMATION: Xaa = any amino acid

<400> SEQUENCE: 157

Cys Xaa Xaa Xaa Xaa Xaa Xaa Xaa Tyr Xaa Asn Xaa Xaa Xaa Xaa
1               5                   10                  15

Xaa Cys

<210> SEQ ID NO 158
<211> LENGTH: 18
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(9)
<223> OTHER INFORMATION: Xaa = any amino acid
<221> NAME/KEY: MISC_FEATURE
<222> LOCATION: (11)..(11)
<223> OTHER INFORMATION: Xaa = any amino acid
<221> NAME/KEY: MISC_FEATURE
```

```
<222> LOCATION: (13)..(17)
<223> OTHER INFORMATION: Xaa = any amino acid

<400> SEQUENCE: 158

Cys Xaa Xaa Xaa Xaa Xaa Xaa Xaa Xaa Tyr Xaa Asn Xaa Xaa Xaa Xaa
1               5                   10                  15

Xaa Cys

<210> SEQ ID NO 159
<211> LENGTH: 18
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(10)
<223> OTHER INFORMATION: Xaa = any amino acid
<221> NAME/KEY: MISC_FEATURE
<222> LOCATION: (12)..(12)
<223> OTHER INFORMATION: Xaa = any amino acid
<221> NAME/KEY: MISC_FEATURE
<222> LOCATION: (14)..(17)
<223> OTHER INFORMATION: Xaa = any amino acid

<400> SEQUENCE: 159

Cys Xaa Xaa Xaa Xaa Xaa Xaa Xaa Xaa Xaa Tyr Xaa Asn Xaa Xaa Xaa
1               5                   10                  15

Xaa Cys

<210> SEQ ID NO 160
<211> LENGTH: 18
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(11)
<223> OTHER INFORMATION: Xaa = any amino acid
<221> NAME/KEY: MISC_FEATURE
<222> LOCATION: (13)..(13)
<223> OTHER INFORMATION: Xaa = any amino acid
<221> NAME/KEY: MISC_FEATURE
<222> LOCATION: (15)..(17)
<223> OTHER INFORMATION: Xaa = any amino acid

<400> SEQUENCE: 160

Cys Xaa Xaa Xaa Xaa Xaa Xaa Xaa Xaa Xaa Xaa Tyr Xaa Asn Xaa Xaa
1               5                   10                  15

Xaa Cys

<210> SEQ ID NO 161
<211> LENGTH: 18
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(12)
<223> OTHER INFORMATION: Xaa = any amino acid
<221> NAME/KEY: MISC_FEATURE
<222> LOCATION: (14)..(14)
<223> OTHER INFORMATION: Xaa = any amino acid
<221> NAME/KEY: MISC_FEATURE
<222> LOCATION: (16)..(17)
<223> OTHER INFORMATION: Xaa = any amino acid

<400> SEQUENCE: 161

Cys Xaa Xaa Xaa Xaa Xaa Xaa Xaa Xaa Xaa Xaa Xaa Tyr Xaa Asn Xaa
1               5                   10                  15
```

Xaa Cys

<210> SEQ ID NO 162
<211> LENGTH: 18
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(13)
<223> OTHER INFORMATION: Xaa = any amino acid
<221> NAME/KEY: MISC_FEATURE
<222> LOCATION: (15)..(15)
<223> OTHER INFORMATION: Xaa = any amino acid
<221> NAME/KEY: MISC_FEATURE
<222> LOCATION: (17)..(17)
<223> OTHER INFORMATION: Xaa = any amino acid

<400> SEQUENCE: 162

Cys Xaa Xaa Xaa Xaa Xaa Xaa Xaa Xaa Xaa Xaa Xaa Xaa Tyr Xaa Asn
1               5                   10                  15

Xaa Cys

<210> SEQ ID NO 163
<211> LENGTH: 18
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(14)
<223> OTHER INFORMATION: Xaa = any amino acid
<221> NAME/KEY: MISC_FEATURE
<222> LOCATION: (16)..(16)
<223> OTHER INFORMATION: Xaa = any amino acid

<400> SEQUENCE: 163

Cys Xaa Xaa Xaa Xaa Xaa Xaa Xaa Xaa Xaa Xaa Xaa Xaa Xaa Tyr Xaa
1               5                   10                  15

Asn Cys

<210> SEQ ID NO 164
<211> LENGTH: 19
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (3)..(3)
<223> OTHER INFORMATION: Xaa = any amino acid
<221> NAME/KEY: MISC_FEATURE
<222> LOCATION: (5)..(18)
<223> OTHER INFORMATION: Xaa = any amino acid

<400> SEQUENCE: 164

Cys Tyr Xaa Asn Xaa Xaa Xaa Xaa Xaa Xaa Xaa Xaa Xaa Xaa Xaa Xaa
1               5                   10                  15

Xaa Xaa Cys

<210> SEQ ID NO 165
<211> LENGTH: 19
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(2)
<223> OTHER INFORMATION: Xaa = any amino acid

```
<221> NAME/KEY: MISC_FEATURE
<222> LOCATION: (4)..(4)
<223> OTHER INFORMATION: Xaa = any amino acid
<221> NAME/KEY: MISC_FEATURE
<222> LOCATION: (6)..(18)
<223> OTHER INFORMATION: Xaa = any amino acid

<400> SEQUENCE: 165

Cys Xaa Tyr Xaa Asn Xaa Xaa Xaa Xaa Xaa Xaa Xaa Xaa Xaa Xaa
1               5                   10                  15

Xaa Xaa Cys

<210> SEQ ID NO 166
<211> LENGTH: 19
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(3)
<223> OTHER INFORMATION: Xaa = any amino acid
<221> NAME/KEY: MISC_FEATURE
<222> LOCATION: (5)..(5)
<223> OTHER INFORMATION: Xaa = any amino acid
<221> NAME/KEY: MISC_FEATURE
<222> LOCATION: (7)..(18)
<223> OTHER INFORMATION: Xaa = any amino acid

<400> SEQUENCE: 166

Cys Xaa Xaa Tyr Xaa Asn Xaa Xaa Xaa Xaa Xaa Xaa Xaa Xaa Xaa
1               5                   10                  15

Xaa Xaa Cys

<210> SEQ ID NO 167
<211> LENGTH: 19
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(4)
<223> OTHER INFORMATION: Xaa = any amino acid
<221> NAME/KEY: MISC_FEATURE
<222> LOCATION: (6)..(6)
<223> OTHER INFORMATION: Xaa = any amino acid
<221> NAME/KEY: MISC_FEATURE
<222> LOCATION: (8)..(18)
<223> OTHER INFORMATION: Xaa = any amino acid

<400> SEQUENCE: 167

Cys Xaa Xaa Xaa Tyr Xaa Asn Xaa Xaa Xaa Xaa Xaa Xaa Xaa Xaa
1               5                   10                  15

Xaa Xaa Cys

<210> SEQ ID NO 168
<211> LENGTH: 19
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(5)
<223> OTHER INFORMATION: Xaa = any amino acid
<221> NAME/KEY: MISC_FEATURE
<222> LOCATION: (7)..(7)
<223> OTHER INFORMATION: Xaa = any amino acid
<221> NAME/KEY: MISC_FEATURE
<222> LOCATION: (9)..(18)
<223> OTHER INFORMATION: Xaa = any amino acid
```

-continued

<400> SEQUENCE: 168

Cys Xaa Xaa Xaa Xaa Tyr Xaa Asn Xaa Xaa Xaa Xaa Xaa Xaa Xaa
1               5                   10                  15

Xaa Xaa Cys

<210> SEQ ID NO 169
<211> LENGTH: 19
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(6)
<223> OTHER INFORMATION: Xaa = any amino acid
<221> NAME/KEY: MISC_FEATURE
<222> LOCATION: (8)..(8)
<223> OTHER INFORMATION: Xaa = any amino acid
<221> NAME/KEY: MISC_FEATURE
<222> LOCATION: (10)..(18)
<223> OTHER INFORMATION: Xaa = any amino acid

<400> SEQUENCE: 169

Cys Xaa Xaa Xaa Xaa Xaa Tyr Xaa Asn Xaa Xaa Xaa Xaa Xaa Xaa
1               5                   10                  15

Xaa Xaa Cys

<210> SEQ ID NO 170
<211> LENGTH: 19
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(7)
<223> OTHER INFORMATION: Xaa = any amino acid
<221> NAME/KEY: MISC_FEATURE
<222> LOCATION: (9)..(9)
<223> OTHER INFORMATION: Xaa = any amino acid
<221> NAME/KEY: MISC_FEATURE
<222> LOCATION: (11)..(18)
<223> OTHER INFORMATION: Xaa = any amino acid

<400> SEQUENCE: 170

Cys Xaa Xaa Xaa Xaa Xaa Xaa Tyr Xaa Asn Xaa Xaa Xaa Xaa Xaa
1               5                   10                  15

Xaa Xaa Cys

<210> SEQ ID NO 171
<211> LENGTH: 19
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(8)
<223> OTHER INFORMATION: Xaa = any amino acid
<221> NAME/KEY: MISC_FEATURE
<222> LOCATION: (10)..(10)
<223> OTHER INFORMATION: Xaa = any amino acid
<221> NAME/KEY: MISC_FEATURE
<222> LOCATION: (12)..(18)
<223> OTHER INFORMATION: Xaa = any amino acid

<400> SEQUENCE: 171

Cys Xaa Xaa Xaa Xaa Xaa Xaa Xaa Tyr Xaa Asn Xaa Xaa Xaa Xaa
1               5                   10                  15

Xaa Xaa Cys

```
<210> SEQ ID NO 172
<211> LENGTH: 19
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(9)
<223> OTHER INFORMATION: Xaa = any amino acid
<221> NAME/KEY: MISC_FEATURE
<222> LOCATION: (11)..(11)
<223> OTHER INFORMATION: Xaa = any amino acid
<221> NAME/KEY: MISC_FEATURE
<222> LOCATION: (13)..(18)
<223> OTHER INFORMATION: Xaa = any amino acid

<400> SEQUENCE: 172

Cys Xaa Xaa Xaa Xaa Xaa Xaa Xaa Xaa Tyr Xaa Asn Xaa Xaa Xaa Xaa
 1               5                  10                  15

Xaa Xaa Cys

<210> SEQ ID NO 173
<211> LENGTH: 19
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(10)
<223> OTHER INFORMATION: Xaa = any amino acid
<221> NAME/KEY: MISC_FEATURE
<222> LOCATION: (12)..(12)
<223> OTHER INFORMATION: Xaa = any amino acid
<221> NAME/KEY: MISC_FEATURE
<222> LOCATION: (14)..(18)
<223> OTHER INFORMATION: Xaa = any amino acid

<400> SEQUENCE: 173

Cys Xaa Xaa Xaa Xaa Xaa Xaa Xaa Xaa Xaa Tyr Xaa Asn Xaa Xaa Xaa
 1               5                  10                  15

Xaa Xaa Cys

<210> SEQ ID NO 174
<211> LENGTH: 19
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(11)
<223> OTHER INFORMATION: Xaa = any amino acid
<221> NAME/KEY: MISC_FEATURE
<222> LOCATION: (13)..(13)
<223> OTHER INFORMATION: Xaa = any amino acid
<221> NAME/KEY: MISC_FEATURE
<222> LOCATION: (15)..(18)
<223> OTHER INFORMATION: Xaa = any amino acid

<400> SEQUENCE: 174

Cys Xaa Xaa Xaa Xaa Xaa Xaa Xaa Xaa Xaa Xaa Tyr Xaa Asn Xaa Xaa
 1               5                  10                  15

Xaa Xaa Cys

<210> SEQ ID NO 175
<211> LENGTH: 19
<212> TYPE: PRT
<213> ORGANISM: Artificial Sequence
<220> FEATURE:
<223> OTHER INFORMATION: One Embodiment of General Formula
```

```
<221> NAME/KEY: MISC_FEATURE
<222> LOCATION: (2)..(12)
<223> OTHER INFORMATION: Xaa = any amino acid
<221> NAME/KEY: MISC_FEATURE
<222> LOCATION: (14)..(14)
<223> OTHER INFORMATION: Xaa = any amino acid
<221> NAME/KEY: MISC_FEATURE
<222> LOCATION: (16)..(18)
<223> OTHER INFORMATION: Xaa = any amino acid

<400> SEQUENCE: 175

Cys Xaa Xaa Xaa Xaa Xaa Xaa Xaa Xaa Xaa Xaa Xaa Tyr Xaa Asn Xaa
1               5                   10                  15

Xaa Xaa Cys

<210> SEQ ID NO 176
<211> LENGTH: 19
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(13)
<223> OTHER INFORMATION: Xaa = any amino acid
<221> NAME/KEY: MISC_FEATURE
<222> LOCATION: (15)..(15)
<223> OTHER INFORMATION: Xaa = any amino acid
<221> NAME/KEY: MISC_FEATURE
<222> LOCATION: (17)..(18)
<223> OTHER INFORMATION: Xaa = any amino acid

<400> SEQUENCE: 176

Cys Xaa Xaa Xaa Xaa Xaa Xaa Xaa Xaa Xaa Xaa Xaa Xaa Tyr Xaa Asn
1               5                   10                  15

Xaa Xaa Cys

<210> SEQ ID NO 177
<211> LENGTH: 19
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(14)
<223> OTHER INFORMATION: Xaa = any amino acid
<221> NAME/KEY: MISC_FEATURE
<222> LOCATION: (16)..(16)
<223> OTHER INFORMATION: Xaa = any amino acid
<221> NAME/KEY: MISC_FEATURE
<222> LOCATION: (18)..(18)
<223> OTHER INFORMATION: Xaa = any amino acid

<400> SEQUENCE: 177

Cys Xaa Xaa Xaa Xaa Xaa Xaa Xaa Xaa Xaa Xaa Xaa Xaa Xaa Tyr Xaa
1               5                   10                  15

Asn Xaa Cys

<210> SEQ ID NO 178
<211> LENGTH: 19
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(15)
<223> OTHER INFORMATION: Xaa = any amino acid
<221> NAME/KEY: MISC_FEATURE
<222> LOCATION: (17)..(17)
<223> OTHER INFORMATION: Xaa = any amino acid
```

```
<400> SEQUENCE: 178

Cys Xaa Xaa Xaa Xaa Xaa Xaa Xaa Xaa Xaa Xaa Xaa Xaa Xaa Tyr
1               5                   10                  15

Xaa Asn Cys

<210> SEQ ID NO 179
<211> LENGTH: 20
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (3)..(3)
<223> OTHER INFORMATION: Xaa = any amino acid
<221> NAME/KEY: MISC_FEATURE
<222> LOCATION: (5)..(19)
<223> OTHER INFORMATION: Xaa = any amino acid

<400> SEQUENCE: 179

Cys Tyr Xaa Asn Xaa Xaa Xaa Xaa Xaa Xaa Xaa Xaa Xaa Xaa Xaa
1               5                   10                  15

Xaa Xaa Xaa Cys
            20

<210> SEQ ID NO 180
<211> LENGTH: 20
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(2)
<223> OTHER INFORMATION: Xaa = any amino acid
<221> NAME/KEY: MISC_FEATURE
<222> LOCATION: (4)..(4)
<223> OTHER INFORMATION: Xaa = any amino acid
<221> NAME/KEY: MISC_FEATURE
<222> LOCATION: (6)..(19)
<223> OTHER INFORMATION: Xaa = any amino acid

<400> SEQUENCE: 180

Cys Xaa Tyr Xaa Asn Xaa Xaa Xaa Xaa Xaa Xaa Xaa Xaa Xaa Xaa
1               5                   10                  15

Xaa Xaa Xaa Cys
            20

<210> SEQ ID NO 181
<211> LENGTH: 20
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(3)
<223> OTHER INFORMATION: Xaa = any amino acid
<221> NAME/KEY: MISC_FEATURE
<222> LOCATION: (5)..(5)
<223> OTHER INFORMATION: Xaa = any amino acid
<221> NAME/KEY: MISC_FEATURE
<222> LOCATION: (7)..(19)
<223> OTHER INFORMATION: Xaa = any amino acid

<400> SEQUENCE: 181

Cys Xaa Xaa Tyr Xaa Asn Xaa Xaa Xaa Xaa Xaa Xaa Xaa Xaa Xaa
1               5                   10                  15

Xaa Xaa Xaa Cys
            20
```

```
<210> SEQ ID NO 182
<211> LENGTH: 20
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(4)
<223> OTHER INFORMATION: Xaa = any amino acid
<221> NAME/KEY: MISC_FEATURE
<222> LOCATION: (6)..(6)
<223> OTHER INFORMATION: Xaa = any amino acid
<221> NAME/KEY: MISC_FEATURE
<222> LOCATION: (8)..(19)
<223> OTHER INFORMATION: Xaa = any amino acid

<400> SEQUENCE: 182

Cys Xaa Xaa Xaa Tyr Xaa Asn Xaa Xaa Xaa Xaa Xaa Xaa Xaa Xaa
 1               5                  10                  15

Xaa Xaa Xaa Cys
            20

<210> SEQ ID NO 183
<211> LENGTH: 20
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(5)
<223> OTHER INFORMATION: Xaa = any amino acid
<221> NAME/KEY: MISC_FEATURE
<222> LOCATION: (7)..(7)
<223> OTHER INFORMATION: Xaa = any amino acid
<221> NAME/KEY: MISC_FEATURE
<222> LOCATION: (9)..(19)
<223> OTHER INFORMATION: Xaa = any amino acid

<400> SEQUENCE: 183

Cys Xaa Xaa Xaa Xaa Tyr Xaa Asn Xaa Xaa Xaa Xaa Xaa Xaa Xaa
 1               5                  10                  15

Xaa Xaa Xaa Cys
            20

<210> SEQ ID NO 184
<211> LENGTH: 20
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(6)
<223> OTHER INFORMATION: Xaa = any amino acid
<221> NAME/KEY: MISC_FEATURE
<222> LOCATION: (8)..(8)
<223> OTHER INFORMATION: Xaa = any amino acid
<221> NAME/KEY: MISC_FEATURE
<222> LOCATION: (10)..(19)
<223> OTHER INFORMATION: Xaa = any amino acid

<400> SEQUENCE: 184

Cys Xaa Xaa Xaa Xaa Xaa Tyr Xaa Asn Xaa Xaa Xaa Xaa Xaa Xaa
 1               5                  10                  15

Xaa Xaa Xaa Cys
            20

<210> SEQ ID NO 185
<211> LENGTH: 20
<212> TYPE: PRT
```

```
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(7)
<223> OTHER INFORMATION: Xaa = any amino acid
<221> NAME/KEY: MISC_FEATURE
<222> LOCATION: (9)..(9)
<223> OTHER INFORMATION: Xaa = any amino acid
<221> NAME/KEY: MISC_FEATURE
<222> LOCATION: (11)..(19)
<223> OTHER INFORMATION: Xaa = any amino acid

<400> SEQUENCE: 185

Cys Xaa Xaa Xaa Xaa Xaa Xaa Tyr Xaa Asn Xaa Xaa Xaa Xaa Xaa
1               5                   10                  15

Xaa Xaa Xaa Cys
            20

<210> SEQ ID NO 186
<211> LENGTH: 20
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(8)
<223> OTHER INFORMATION: Xaa = any amino acid
<221> NAME/KEY: MISC_FEATURE
<222> LOCATION: (10)..(10)
<223> OTHER INFORMATION: Xaa = any amino acid
<221> NAME/KEY: MISC_FEATURE
<222> LOCATION: (12)..(19)
<223> OTHER INFORMATION: Xaa = any amino acid

<400> SEQUENCE: 186

Cys Xaa Xaa Xaa Xaa Xaa Xaa Xaa Tyr Xaa Asn Xaa Xaa Xaa Xaa
1               5                   10                  15

Xaa Xaa Xaa Cys
            20

<210> SEQ ID NO 187
<211> LENGTH: 20
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(9)
<223> OTHER INFORMATION: Xaa = any amino acid
<221> NAME/KEY: MISC_FEATURE
<222> LOCATION: (11)..(11)
<223> OTHER INFORMATION: Xaa = any amino acid
<221> NAME/KEY: MISC_FEATURE
<222> LOCATION: (13)..(19)
<223> OTHER INFORMATION: Xaa = any amino acid

<400> SEQUENCE: 187

Cys Xaa Xaa Xaa Xaa Xaa Xaa Xaa Xaa Tyr Xaa Asn Xaa Xaa Xaa
1               5                   10                  15

Xaa Xaa Xaa Cys
            20

<210> SEQ ID NO 188
<211> LENGTH: 20
<212> TYPE: PRT
<213> ORGANISM: Artificial Sequence
<220> FEATURE:
<223> OTHER INFORMATION: One Embodiment of General Formula
<221> NAME/KEY: MISC_FEATURE
```

<222> LOCATION: (2)..(10)
<223> OTHER INFORMATION: Xaa = any amino acid
<221> NAME/KEY: MISC_FEATURE
<222> LOCATION: (12)..(12)
<223> OTHER INFORMATION: Xaa = any amino acid
<221> NAME/KEY: MISC_FEATURE
<222> LOCATION: (14)..(19)
<223> OTHER INFORMATION: Xaa = any amino acid

<400> SEQUENCE: 188

Cys Xaa Xaa Xaa Xaa Xaa Xaa Xaa Xaa Xaa Tyr Xaa Asn Xaa Xaa Xaa
1               5                   10                  15

Xaa Xaa Xaa Cys
        20

<210> SEQ ID NO 189
<211> LENGTH: 20
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(11)
<223> OTHER INFORMATION: Xaa = any amino acid
<221> NAME/KEY: MISC_FEATURE
<222> LOCATION: (13)..(13)
<223> OTHER INFORMATION: Xaa = any amino acid
<221> NAME/KEY: MISC_FEATURE
<222> LOCATION: (15)..(19)
<223> OTHER INFORMATION: Xaa = any amino acid

<400> SEQUENCE: 189

Cys Xaa Xaa Xaa Xaa Xaa Xaa Xaa Xaa Xaa Xaa Tyr Xaa Asn Xaa Xaa
1               5                   10                  15

Xaa Xaa Xaa Cys
        20

<210> SEQ ID NO 190
<211> LENGTH: 20
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(12)
<223> OTHER INFORMATION: Xaa = any amino acid
<221> NAME/KEY: MISC_FEATURE
<222> LOCATION: (14)..(14)
<223> OTHER INFORMATION: Xaa = any amino acid
<221> NAME/KEY: MISC_FEATURE
<222> LOCATION: (16)..(19)
<223> OTHER INFORMATION: Xaa = any amino acid

<400> SEQUENCE: 190

Cys Xaa Xaa Xaa Xaa Xaa Xaa Xaa Xaa Xaa Xaa Xaa Tyr Xaa Asn Xaa
1               5                   10                  15

Xaa Xaa Xaa Cys
        20

<210> SEQ ID NO 191
<211> LENGTH: 20
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(13)
<223> OTHER INFORMATION: Xaa = any amino acid
<221> NAME/KEY: MISC_FEATURE
<222> LOCATION: (15)..(15)

```
<223> OTHER INFORMATION: Xaa = any amino acid
<221> NAME/KEY: MISC_FEATURE
<222> LOCATION: (17)..(19)
<223> OTHER INFORMATION: Xaa = any amino acid

<400> SEQUENCE: 191

Cys Xaa Xaa Xaa Xaa Xaa Xaa Xaa Xaa Xaa Xaa Xaa Xaa Tyr Xaa Asn
1               5                   10                  15

Xaa Xaa Xaa Cys
            20

<210> SEQ ID NO 192
<211> LENGTH: 20
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(14)
<223> OTHER INFORMATION: Xaa = any amino acid
<221> NAME/KEY: MISC_FEATURE
<222> LOCATION: (16)..(16)
<223> OTHER INFORMATION: Xaa = any amino acid
<221> NAME/KEY: MISC_FEATURE
<222> LOCATION: (18)..(19)
<223> OTHER INFORMATION: Xaa = any amino acid

<400> SEQUENCE: 192

Cys Xaa Xaa Xaa Xaa Xaa Xaa Xaa Xaa Xaa Xaa Xaa Xaa Xaa Tyr Xaa
1               5                   10                  15

Asn Xaa Xaa Cys
            20

<210> SEQ ID NO 193
<211> LENGTH: 20
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(15)
<223> OTHER INFORMATION: Xaa = any amino acid
<221> NAME/KEY: MISC_FEATURE
<222> LOCATION: (17)..(17)
<223> OTHER INFORMATION: Xaa = any amino acid
<221> NAME/KEY: MISC_FEATURE
<222> LOCATION: (19)..(19)
<223> OTHER INFORMATION: Xaa = any amino acid

<400> SEQUENCE: 193

Cys Xaa Xaa Xaa Xaa Xaa Xaa Xaa Xaa Xaa Xaa Xaa Xaa Xaa Xaa Tyr
1               5                   10                  15

Xaa Asn Xaa Cys
            20

<210> SEQ ID NO 194
<211> LENGTH: 20
<212> TYPE: PRT
<213> ORGANISM: Artificial Sequence
<220> FEATURE:
<223> OTHER INFORMATION: One Embodiment of General Formula
<221> NAME/KEY: MISC_FEATURE
<222> LOCATION: (2)..(16)
<223> OTHER INFORMATION: Xaa = any amino acid
<221> NAME/KEY: MISC_FEATURE
<222> LOCATION: (18)..(18)
<223> OTHER INFORMATION: Xaa = any amino acid
```

```
-continued

<400> SEQUENCE: 194

Cys Xaa Xaa Xaa Xaa Xaa Xaa Xaa Xaa Xaa Xaa Xaa Xaa Xaa Xaa Xaa
1               5                   10                  15

Tyr Xaa Asn Cys
        20
```